(12) United States Patent
Bee et al.

(10) Patent No.: US 10,928,553 B2
(45) Date of Patent: Feb. 23, 2021

(54) STRUCTURALLY-COLORED ARTICLES AND METHODS FOR MAKING AND USING STRUCTURALLY-COLORED ARTICLES

(71) Applicant: NIKE, Inc., Beaverton, OR (US)

(72) Inventors: Jennifer Bee, Portland, OR (US); Jeremy Gantz, Lake Oswego, OR (US); Kim Kovel, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 61 days.

(21) Appl. No.: 16/146,560

(22) Filed: Sep. 28, 2018

(65) Prior Publication Data

US 2019/0099968 A1 Apr. 4, 2019

Related U.S. Application Data

(60) Provisional application No. 62/565,299, filed on Sep. 29, 2017, provisional application No. 62/633,666, (Continued)

(51) Int. Cl.
*G02B 1/00* (2006.01)
*G02B 5/00* (2006.01)
(Continued)

(52) U.S. Cl.
CPC .............. *G02B 1/04* (2013.01); *A41D 27/08* (2013.01); *A43B 1/0027* (2013.01);
(Continued)

(58) Field of Classification Search
CPC ... G02B 1/00; G02B 1/04; G02B 1/10; G02B 5/00; G02B 5/08; G02B 5/081; (Continued)

(56) References Cited

U.S. PATENT DOCUMENTS 2,345,533 A 3/1944 Graves
2,607,130 A 8/1952 Pearson
(Continued)

FOREIGN PATENT DOCUMENTS

AU 2007200128 A1 1/2007
CH 702116 B1 5/2011
(Continued)

OTHER PUBLICATIONS

Masanori Iwata et al., Bio-Inspired Bright Structurally Colored Colloidal Amorphous Array Enhanced by Controlling Thickness and Black Background, Advanced Materials, Feb. 21, 2017, 1-8, 1605050, Germany.
(Continued)

*Primary Examiner* — Jacob T Minskey
*Assistant Examiner* — Matthew Hoover
(74) *Attorney, Agent, or Firm* — Thomas|Horstemeyer, LLP

(57) ABSTRACT

One or more aspects of the present disclosure provide optical element transfer structures that include an optical element releasably coupled with a transfer medium and methods of making and using the optical element transfer structures. The optical element transfer structures can be used to dispose an optical element onto an article, whereby the optical element imparts a structural color to the article.

20 Claims, 2 Drawing Sheets

Related U.S. Application Data filed on Feb. 22, 2018, provisional application No. 62/565,306, filed on Sep. 29, 2017, provisional application No. 62/565,313, filed on Sep. 29, 2017, provisional application No. 62/565,310, filed on Sep. 29, 2017.

(51) Int. Cl.

| | | |
|---|---|---|
| *C09D 7/00* | (2018.01) | |
| *B32B 7/00* | (2019.01) | |
| *A41D 27/00* | (2006.01) | |
| *A43B 1/00* | (2006.01) | |
| *A43B 13/00* | (2006.01) | |
| *A43B 21/00* | (2006.01) | |
| *A43B 23/00* | (2006.01) | |
| *B29D 11/00* | (2006.01) | |
| *B32B 3/00* | (2006.01) | |
| *B32B 5/00* | (2006.01) | |
| *B32B 15/00* | (2006.01) | |
| *B32B 27/00* | (2006.01) | |
| *B32B 33/00* | (2006.01) | |
| *B32B 37/00* | (2006.01) | |
| *B32B 38/00* | (2006.01) | |
| *C09D 5/00* | (2006.01) | |
| *G02B 1/04* | (2006.01) | |
| *B32B 5/02* | (2006.01) | |
| *A43B 21/28* | (2006.01) | |
| *B32B 7/023* | (2019.01) | |
| *A43B 13/18* | (2006.01) | |
| *B32B 38/06* | (2006.01) | |
| *A41D 27/08* | (2006.01) | |
| *A43B 13/14* | (2006.01) | |
| *A43B 23/24* | (2006.01) | |
| *G02B 5/08* | (2006.01) | |
| *G02B 5/28* | (2006.01) | |
| *A43B 1/14* | (2006.01) | |
| *A43B 13/04* | (2006.01) | |
| *A43B 13/12* | (2006.01) | |
| *A43B 13/20* | (2006.01) | |
| *A43B 13/22* | (2006.01) | |
| *A43B 23/02* | (2006.01) | |
| *B32B 3/30* | (2006.01) | |
| *B32B 27/08* | (2006.01) | |
| *B32B 27/12* | (2006.01) | |
| *B32B 27/34* | (2006.01) | |
| *B32B 27/40* | (2006.01) | |
| *C09D 7/61* | (2018.01) | |
| *B32B 15/095* | (2006.01) | |
| *G02B 1/10* | (2015.01) | |
| *G02B 5/26* | (2006.01) | |
| *A41D 1/089* | (2018.01) | |
| *A41B 1/08* | (2006.01) | |
| *A41B 11/00* | (2006.01) | |
| *A41D 1/04* | (2006.01) | |
| *A42B 1/004* | (2021.01) | |
| *A45F 3/04* | (2006.01) | |
| *A63B 41/08* | (2006.01) | |
| *A63B 71/14* | (2006.01) | |
| *A41D 13/01* | (2006.01) | |
| *A43B 5/00* | (2006.01) | |
| *C08K 3/28* | (2006.01) | |

(52) U.S. Cl.
CPC .............. *A43B 1/0072* (2013.01); *A43B 1/14* (2013.01); *A43B 13/04* (2013.01); *A43B 13/122* (2013.01); *A43B 13/14* (2013.01); *A43B 13/188* (2013.01); *A43B 13/20* (2013.01); *A43B 13/22* (2013.01); *A43B 21/28* (2013.01); *A43B 23/026* (2013.01); *A43B 23/24* (2013.01); *B29D 11/0074* (2013.01); *B29D 11/00865* (2013.01); *B32B 3/30* (2013.01); *B32B 5/02* (2013.01); *B32B 5/022* (2013.01); *B32B 5/024* (2013.01); *B32B 7/023* (2019.01); *B32B 15/095* (2013.01); *B32B 27/08* (2013.01); *B32B 27/12* (2013.01); *B32B 27/34* (2013.01); *B32B 27/40* (2013.01); *B32B 33/00* (2013.01); *B32B 37/025* (2013.01); *B32B 38/06* (2013.01); *C09D 5/002* (2013.01); *C09D 7/61* (2018.01); *G02B 1/10* (2013.01); *G02B 5/0816* (2013.01); *G02B 5/26* (2013.01); *G02B 5/28* (2013.01); *G02B 5/285* (2013.01); *A41B 1/08* (2013.01); *A41B 11/001* (2013.01); *A41D 1/04* (2013.01); *A41D 1/089* (2018.01); *A41D 13/01* (2013.01); *A42B 1/004* (2013.01); *A43B 5/00* (2013.01); *A45F 3/04* (2013.01); *A63B 41/08* (2013.01); *A63B 71/143* (2013.01); *B32B 2255/10* (2013.01); *B32B 2255/26* (2013.01); *B32B 2274/00* (2013.01); *B32B 2305/188* (2013.01); *B32B 2307/402* (2013.01); *B32B 2307/409* (2013.01); *B32B 2307/416* (2013.01); *B32B 2367/00* (2013.01); *B32B 2437/02* (2013.01); *C08K 3/28* (2013.01)

(58) Field of Classification Search
CPC .......... G02B 5/0816; G02B 5/20; G02B 5/26; G02B 5/28; G02B 5/285; C09D 5/00; C09D 5/002; C09D 7/00; C09D 7/60; C09D 7/61; B32B 3/00; B32B 3/30; B32B 5/00; B32B 5/02; B32B 5/022; B32B 7/00; B32B 7/02; B32B 7/023; B32B 15/00; B32B 15/09; B32B 15/095; B32B 27/00; B32B 27/08; B32B 27/10; B32B 27/12; B32B 27/30; B32B 27/34; B32B 27/40; B32B 33/00; B32B 37/00; B32B 37/02; B32B 37/025; B32B 38/00; B32B 38/06; A41D 27/00; A41D 27/08; A43B 1/00; A43B 1/002; A43B 1/0027; A43B 1/007; A43B 1/0072; A43B 1/10; A43B 1/14; A43B 13/00; A43B 13/04; A43B 13/10; A43B 13/12; A43B 13/122; A43B 13/14; A43B 13/18; A43B 13/188; A43B 13/20; A43B 13/22; A43B 21/00; A43B 21/20; A43B 21/28; A43B 23/00; A43B 23/02; A43B 23/026; A43B 23/20; A43B 23/24; B29D 11/00; B29D 11/007; B29D 11/0074; B29D 11/008; B29D 11/0086; B29D 11/00865

See application file for complete search history.

(56) References Cited

U.S. PATENT DOCUMENTS

| | | |
|---|---|---|
| 2,929,803 A | 3/1960 | Frazer |
| 4,231,369 A | 11/1980 | Sorensen et al. |
| 4,705,356 A | 11/1987 | Berning |
| 5,572,817 A | 11/1996 | Chien |
| 5,722,322 A | 3/1998 | Watanabe |
| 5,813,148 A | 9/1998 | Guerra |
| 5,815,950 A | 10/1998 | Wang |
| 5,930,921 A | 8/1999 | Sorofman et al. |
| 5,979,078 A | 11/1999 | McLaughlin |
| 6,127,026 A * | 10/2000 | Bonk .................... A43B 13/20 |
| | | 428/213 |

(56) References Cited

U.S. PATENT DOCUMENTS

| | | |
|---|---|---|
| 6,402,879 B1 | 6/2002 | Tawney et al. |
| 6,761,959 B1 | 7/2004 | Bonkowski et al. |
| 7,006,294 B2 | 2/2006 | Steenblik et al. |
| 7,800,814 B2 | 9/2010 | Nishimura et al. |
| 7,848,008 B2 | 12/2010 | Nishimura et al. |
| 7,903,339 B2 | 3/2011 | Banerjee et al. |
| 7,955,695 B2 | 6/2011 | Argoitia |
| 8,264,637 B2 | 9/2012 | Cho et al. |
| 8,322,636 B2 | 12/2012 | Wu et al. |
| 8,339,597 B2 | 12/2012 | Dal Negro et al. |
| 8,408,470 B2 | 4/2013 | Komatsu et al. |
| 8,486,494 B2 | 7/2013 | Fukazawa et al. |
| 8,558,137 B2 | 10/2013 | Yuasa et al. |
| 8,685,185 B2 | 4/2014 | Guo et al. |
| 8,889,234 B2 | 11/2014 | Kwon et al. |
| 9,102,195 B2 | 8/2015 | Raksha et al. |
| 9,134,468 B2 | 9/2015 | Noizet et al. |
| 9,220,951 B1 | 12/2015 | Comeau |
| 9,279,771 B2 | 3/2016 | Aizenberg et al. |
| 9,527,340 B2 | 12/2016 | Szumski et al. |
| 9,557,457 B2 | 1/2017 | Gocho et al. |
| 2001/0042321 A1 | 11/2001 | Tawney et al. |
| 2001/0053454 A1 | 12/2001 | Higashi |
| 2002/0183133 A1 | 12/2002 | Sano |
| 2003/0074808 A1 | 4/2003 | Weaver et al. |
| 2004/0112252 A1 | 6/2004 | Zimmerman |
| 2004/0169928 A1 | 9/2004 | Nilsen et al. |
| 2004/0172855 A1 | 9/2004 | Aslanides |
| 2005/0031816 A1 | 2/2005 | Chang et al. |
| 2005/0211114 A1 | 9/2005 | Fahrenbach et al. |
| 2005/0260369 A1 | 11/2005 | Graf et al. |
| 2006/0023327 A1 | 2/2006 | Coombs |
| 2006/0128823 A1 | 6/2006 | Tsuchimura et al. |
| 2006/0270553 A1 | 11/2006 | Mori |
| 2007/0008439 A1 | 1/2007 | Nakayama et al. |
| 2007/0058260 A1 | 3/2007 | Steenblik et al. |
| 2007/0076069 A1 | 4/2007 | Edwards et al. |
| 2008/0066347 A1 | 3/2008 | Suzuki |
| 2008/0248281 A1 | 10/2008 | Nakaguma et al. |
| 2009/0174944 A1 | 7/2009 | Yuasa et al. |
| 2009/0301649 A1 | 12/2009 | Augsberg et al. |
| 2010/0104810 A1 | 4/2010 | Fukazawa et al. |
| 2010/0152065 A1 | 6/2010 | Nishimura et al. |
| 2010/0199406 A1 | 8/2010 | Dua et al. |
| 2010/0199520 A1 | 8/2010 | Dua et al. |
| 2010/0245978 A1 | 9/2010 | Baumberg et al. |
| 2010/0266946 A1 | 10/2010 | Shirai et al. |
| 2010/0291358 A1 | 11/2010 | Takahashi et al. |
| 2011/0026208 A1 | 2/2011 | Utsuro et al. |
| 2011/0033670 A1 | 2/2011 | Nishikawa et al. |
| 2011/0043911 A1 | 2/2011 | Kaneiwa et al. |
| 2011/0090564 A1 | 4/2011 | Utsuro et al. |
| 2011/0123754 A1* | 5/2011 | Shirai ............... B32B 27/08 428/41.8 |
| 2011/0171440 A1 | 7/2011 | Cheng et al. |
| 2011/0183111 A1 | 7/2011 | Yuasa et al. |
| 2011/0234953 A1 | 9/2011 | Amimori et al. |
| 2011/0234969 A1 | 9/2011 | Amimori et al. |
| 2011/0253288 A1 | 10/2011 | Xie et al. |
| 2011/0262675 A1 | 10/2011 | Inamiya et al. |
| 2012/0015118 A1 | 1/2012 | Zheludev et al. |
| 2012/0015145 A1 | 1/2012 | Depres |
| 2012/0034291 A1 | 2/2012 | Amsden et al. |
| 2012/0121820 A1 | 5/2012 | Kaplan et al. |
| 2012/0133672 A1 | 5/2012 | Joo |
| 2012/0139230 A1 | 6/2012 | Whiteman et al. |
| 2012/0231489 A1 | 9/2012 | Lenhert |
| 2012/0236415 A1 | 9/2012 | Nagano et al. |
| 2012/0249718 A1 | 10/2012 | Sohn et al. |
| 2012/0255201 A1 | 10/2012 | Little |
| 2012/0255452 A1 | 10/2012 | Bower et al. |
| 2012/0276332 A1 | 11/2012 | Conolly |
| 2013/0004721 A1 | 1/2013 | Hara et al. |
| 2013/0004722 A1 | 1/2013 | Hara et al. |
| 2013/0004731 A1 | 1/2013 | Hara et al. |
| 2013/0004754 A1 | 1/2013 | Hara et al. |
| 2013/0183487 A1 | 7/2013 | Henze et al. |
| 2013/0243693 A1 | 9/2013 | Omenetto et al. |
| 2013/0330710 A1 | 12/2013 | Omenetto et al. |
| 2014/0016177 A1 | 1/2014 | Aizenberg et al. |
| 2014/0050899 A1 | 2/2014 | Kukoff |
| 2014/0104686 A1 | 4/2014 | Yuasa et al. |
| 2014/0106139 A1* | 4/2014 | Abrams ............... C09J 7/35 428/200 |
| 2014/0161974 A1 | 6/2014 | Erho et al. |
| 2014/0250734 A1 | 9/2014 | Zheng |
| 2014/0254017 A1 | 9/2014 | Manoharan et al. |
| 2015/0035269 A1 | 2/2015 | Hooper et al. |
| 2015/0076808 A1 | 3/2015 | Kim et al. |
| 2015/0109657 A1 | 4/2015 | Baumberg et al. |
| 2015/0118124 A1 | 4/2015 | Khorasaninejad et al. |
| 2015/0146280 A1 | 5/2015 | Degott et al. |
| 2015/0192897 A1 | 7/2015 | Schilling et al. |
| 2015/0202834 A1* | 7/2015 | Free ............... G02B 1/02 428/141 |
| 2015/0250263 A1 | 9/2015 | Robinson, Jr. |
| 2015/0283743 A1 | 10/2015 | Park et al. |
| 2015/0309232 A1 | 10/2015 | Banerjee |
| 2015/0352883 A1 | 12/2015 | Schmid et al. |
| 2015/0352888 A1 | 12/2015 | Schmid et al. |
| 2016/0064696 A1 | 3/2016 | Collier et al. |
| 2016/0116645 A1 | 4/2016 | Parker |
| 2016/0128433 A1 | 5/2016 | Downing et al. |
| 2016/0131808 A1 | 5/2016 | Kristensen et al. |
| 2016/0146984 A1 | 5/2016 | Jiang et al. |
| 2016/0168386 A1 | 6/2016 | Aizenberg et al. |
| 2016/0176223 A1 | 6/2016 | Degott et al. |
| 2016/0178493 A1 | 6/2016 | Kawanaka et al. |
| 2016/0202394 A1 | 7/2016 | Clausen et al. |
| 2016/0202401 A1 | 7/2016 | Christiansen et al. |
| 2016/0209642 A1 | 7/2016 | Aizenberg et al. |
| 2016/0282527 A1 | 9/2016 | Saito et al. |
| 2016/0325310 A1 | 11/2016 | Schmid et al. |
| 2017/0023711 A1 | 1/2017 | Jiang et al. |
| 2017/0081535 A1 | 3/2017 | Kohri et al. |
| 2017/0087691 A1 | 3/2017 | Yokoyama et al. |
| 2017/0090084 A1 | 3/2017 | Wilson et al. |
| 2017/0129200 A1 | 5/2017 | Adami et al. |
| 2017/0157653 A1 | 6/2017 | Parker |
| 2017/0248746 A1 | 8/2017 | Banerjee |
| 2019/0099967 A1 | 4/2019 | Bee |

FOREIGN PATENT DOCUMENTS

| | | |
|---|---|---|
| CN | 1324222 A | 11/2001 |
| CN | 101381903 A | 3/2009 |
| CN | 101633786 A | 1/2010 |
| CN | 101666886 A | 3/2010 |
| CN | 102548752 A | 7/2012 |
| CN | 102691202 A | 9/2012 |
| CN | 103173039 A | 6/2013 |
| CN | 103965699 A | 8/2014 |
| CN | 104592971 A | 5/2015 |
| CN | 105271796 A | 1/2016 |
| CN | 105862000 A | 8/2016 |
| CN | 106080001 A | 11/2016 |
| DE | 20200346 U1 | 4/2002 |
| DE | 102010025159 A1 | 12/2011 |
| EP | 0905530 A2 | 3/1999 |
| EP | 1624026 A1 | 2/2003 |
| EP | 1653256 A1 | 5/2006 |
| EP | 2012148 A1 | 1/2009 |
| EP | 3151042 A1 | 4/2017 |
| EP | 3278150 A2 | 2/2018 |
| GB | 2481697 A | 1/2012 |
| GB | 2525020 A | 10/2015 |
| JP | 2005226196 A | 8/2005 |
| JP | 2010111974 A | 5/2010 |
| JP | 2011085779 A | 4/2011 |
| JP | 2011104931 A | 6/2011 |
| JP | 2013029805 A | 2/2013 |
| JP | 2013080049 A | 5/2013 |
| JP | 2014189719 A | 10/2014 |
| JP | 2015069076 A | 4/2015 |

(56) References Cited

FOREIGN PATENT DOCUMENTS

| | | |
|---|---|---|
| JP | 2016502470 A | 1/2016 |
| JP | 2017032409 A | 2/2017 |
| WO | 9701972 A1 | 1/1997 |
| WO | 03046039 A1 | 6/2003 |
| WO | 03/06825 A1 | 8/2003 |
| WO | 2007/038097 A1 | 4/2007 |
| WO | 2007037393 A1 | 4/2007 |
| WO | 2008076339 A2 | 6/2008 |
| WO | 2007037393 A1 | 4/2009 |
| WO | 2010119248 A2 | 10/2010 |
| WO | 2011161482 A1 | 12/2011 |
| WO | 2010047322 A1 | 3/2012 |
| WO | 2019067969 A1 | 4/2012 |
| WO | 2012055105 A1 | 5/2012 |
| WO | 2013151547 A1 | 10/2013 |
| WO | 2014/022049 A1 | 2/2014 |
| WO | 2014059424 A2 | 4/2014 |
| WO | 2014/117673 A1 | 8/2014 |
| WO | 2014133514 A1 | 9/2014 |
| WO | 2015051367 A1 | 4/2015 |
| WO | 2015151479 A1 | 10/2015 |
| WO | 2015170120 A1 | 11/2015 |
| WO | 2016015973 A1 | 2/2016 |
| WO | 2016092014 A1 | 6/2016 |
| WO | 2016103980 A1 | 6/2016 |
| WO | 2016140779 A1 | 9/2016 |
| WO | 2016156863 A2 | 10/2016 |
| WO | 2016164551 A1 | 10/2016 |
| WO | 2016193252 A1 | 12/2016 |
| WO | 2017006314 A1 | 1/2017 |
| WO | 2017032928 A1 | 3/2017 |
| WO | 2017041085 A1 | 3/2017 |
| WO | 2018130856 A1 | 7/2018 |
| WO | 2018/160866 A1 | 9/2018 |

OTHER PUBLICATIONS

International Search Report and Written Opinion for PCT/US2018/053478 dated Jun. 4, 2019.
International Search Report and Written Opinion for PCT/US2018/053516 dated May 31, 2019.
International Search Report and Written Opinion for PCT/US2018/053502 dated May 28, 2019.
International Search Report and Written Opinion for PCT/US2018/053488 dated Jun. 4, 2019.
International Search Report and Written Opinion for PCT/US2018/053529 dated Jan. 28, 2019.
International Preliminary Report on Patentability for PCT/US2018/053529 dated Dec. 18, 2019.
International Search Report and Written Opinion for PCT/US2018/053521 dated Jun. 3, 2019.
International Preliminary Report on Patentability for PCT/US2018/053521 dated Sep. 3, 2019.
International Search Report and Written Opinion for PCT/US2018/053467 dated Jun. 3, 2019.
International Preliminary Report on Patentability for PCT/US2018/053467 dated Dec. 17, 2019.
International Search Report and Written Opinion for PCT/US2018/053510 dated May 29, 2019.
International Preliminary Report on Patentability for PCT/US2018/053510 dated Dec. 20, 2019.
Texture-www.vocabulary.com, Jun. 2, 2020 (Year: 2020).
Color-www.dictionary.com, Jun. 2, 2020 (Year: 2020).
International Preliminary Report on Patentability for PCT/US2018/053478 dated Mar. 31, 2020.
International Preliminary Report on Patentability for PCT/US2018/053516 dated Mar. 31, 2020.
International Preliminary Report on Patentability for PCT/US2018/053502 dated Mar. 31, 2020.
International Preliminary Report on Patentability for PCT/US2018/053488 dated Mar. 31, 2020.
Written Opinion of the International Preliminary Examining Authority for PCT/US2018/053510 dated Sep. 24, 2019.
International Search Report and Written Opinion for PCT/US2020/022099 dated Jun. 22, 2020.
International Search Report and Written Opinion for PCT/US2020/022129 dated Jun. 8, 2020.
OHARA et al: "Structurally Colored Fibers", Chemical Fibers International, vol. 50, No. 1, Feb. 1, 2000 (Feb. 1, 2000), p. 38/39.
International Search Report and Written Opinion for PCT/US2020/022109 dated Jul. 13, 2020.
International Search Report and Written Opinion for PCT/US2020/022148 dated Jul. 15, 2020.
International Search Report and Written Opinion dated Oct. 8, 2020 for PCT/US2020/043273.
International Search Report and Written Opinion for PCT/US2020/043271 dated Oct. 23, 2020.
International Search Report and Written Opinion for PCT/2020/044626 dated Oct. 30, 2020.
International Search Report and Written Opinion for PCT/US2020/044624 dated Oct. 30, 2020.
International Search Report and Written Opinion for PCT/US2020/044628 dated Oct. 30, 2020.

* cited by examiner

STRUCTURALLY-COLORED ARTICLES AND METHODS FOR MAKING AND USING STRUCTURALLY-COLORED ARTICLES

CROSS-REFERENCE TO RELATED APPLICATIONS

This application claims the benefit of and priority to U.S. Provisional Application Ser. No. 62/565,299, having the title "STRUCTURALLY COLORED ARTICLES AND METHODS OF MAKING STRUCTURALLY COLORED ARTICLES", filed on Sep. 29, 2017, and to U.S. Provisional Application Ser. No. 62/633,666, having the title "ARTICLES HAVING STRUCTURAL COLOR AND METHODS AND SYSTEMS FOR MAKING ARTICLES HAVING STRUCTURAL COLOR", filed on Feb. 22, 2018, and to U.S. Provisional Application Ser. No. 62/565,306, having the title "STRUCTURALLY COLORED STRUCTURES AND ARTICLES, METHODS OF MAKING STRUCTURES AND ARTICLES", filed on Sep. 29, 2017, and to U.S. Provisional Application Ser. No. 62/565,313, having the title "STRUCTURES HAVING STRUCTURAL COLOR AND METHODS AND SYSTEMS FOR MAKING STRUCTURES HAVING STRUCTURAL COLOR", filed on Sep. 29, 2017, and U.S. Provisional Application Ser. No. 62/565,310, having the title "STRUCTURES HAVING STRUCTURAL COLOR AND METHODS AND SYSTEMS FOR MAKING STRUCTURES HAVING STRUCTURAL COLOR", filed on Sep. 29, 2017, the disclosures which are incorporated herein by reference in their entireties.

BACKGROUND

Structural color is caused by the physical interaction of light with the micro- or nano-features of a surface and the bulk material as compared to color derived from the presence of dyes or pigments that absorb or reflect specific wavelengths of light based on the chemical properties of the dyes or pigments. Color from dyes and pigments can be problematic in a number of ways. For example, dyes and pigments and their associated chemistries for fabrication and incorporation into finished goods may not be environmentally friendly.

BRIEF DESCRIPTION OF THE DRAWINGS

Further embodiments of the present disclosure will be more readily appreciated upon review of the detailed description of its various embodiments, described below, when taken in conjunction with the accompanying drawings.

DESCRIPTION

Figure 1A:
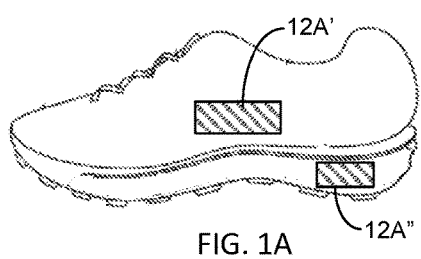
FIGS. 1A-1M illustrates footwear, apparel, athletic equipment, containers, electronic equipment, and vision wear that include the optical element of the present disclosure.
Figure 1B:
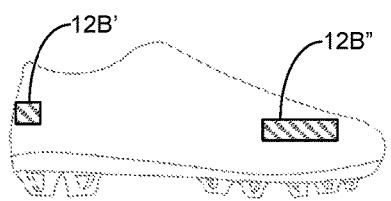
Figure 1C:
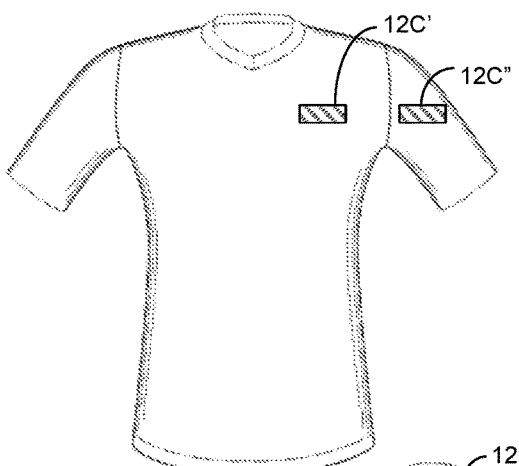
Figure 1D:
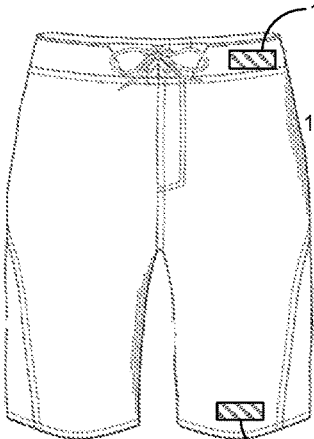
Figure 1E:
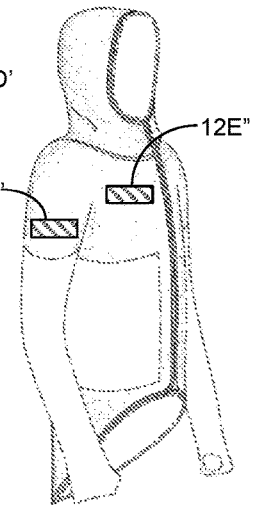
Figure 1F:
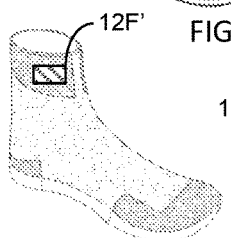
Figure 1G:
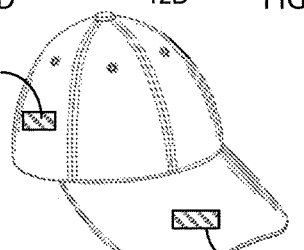
Figure 1H:
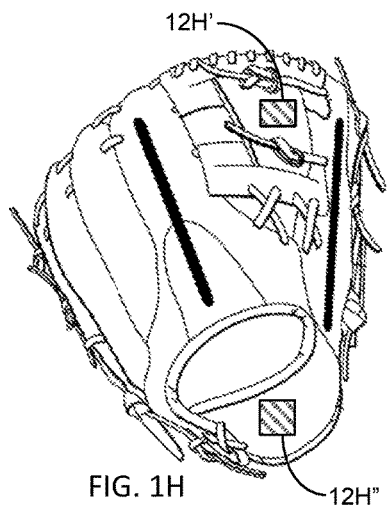
Figure 1I:
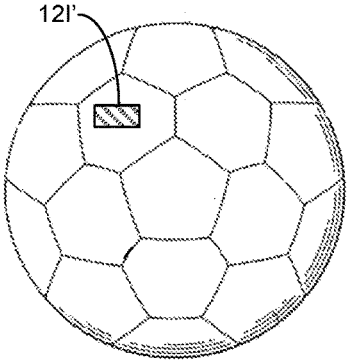
Figure 1J:
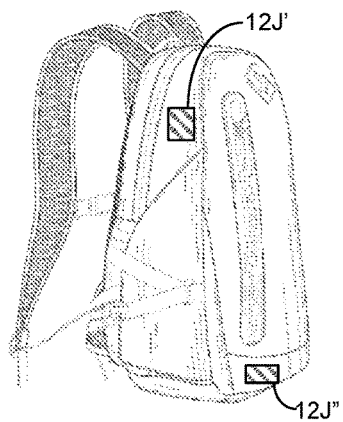
Figure 1K:
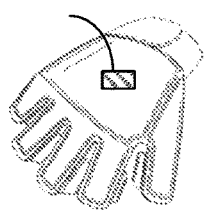
Figure 1L:
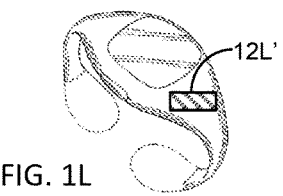
Figure 1M:
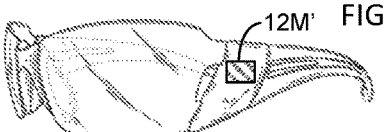

The present disclosure provides for articles methods of making articles that exhibit structural colors through the use of optical elements disposed onto the article using a transfer structure, where structural colors are visible colors produced, at least in part, through optical effects (e.g., through scattering, refraction, reflection, interference, and/or diffraction of visible wavelengths of light). The structural color imparts an aesthetically appealing color to the article without requiring the use of inks or pigments and the environmental impact associated with their use.

One or more aspects of the present disclosure is directed to transfer structures having an optical element disposed thereon (optical element transfer structures) and methods of forming transfer structures and using transfer structures in methods to dispose an optical element to an article to impart structural color to the article. In an aspect, an optical element transfer structure can be formed of the optical element (e.g., a single or multilayer reflector or a multilayer filter) disposed on a transfer medium (e.g., release paper). The transfer structure can then be used to apply the optical element or portions thereof to the article.

According to various aspects, the optical element transferred using the transfer structure can be used alone or optionally in combination with a textured surface, a primer layer, or both to impart the structural color. The textured surface and/or the primer layer can be part of the optical element or can be separate from the optical element, but, when used with the optical element, impart the structural color. In other words, while the optical element alone can impart a first structural color, the combination of the optical element with the textured surface or primer layer or both impart a second structural color. In some examples, the second structural color is the same as the second structural color. Alternatively, the second structural color can differ from the first structural color optical element based on a color parameter such as hue, lightness, or iridescence type. In such cases, the combination of the optical element and the textured surface and/or the primer layer impart the structural color to the article.

After disposing the optical element to the article, the article exhibits a different color from the underlying surface of the article, without the application of additional pigments or dyes to the article. For example, the structural color can differ from the color of the underlying surface of the article based on a color parameter such as hue, lightness, iridescence type, or any combination thereof. In particular examples, the structural color and the color of the underlying surface of the article differ both in hue and iridescence type, where the structural color is iridescent (e.g., exhibits two or more different hues when viewed from at least two different angles 15 degrees apart), and the color of the underlying surface is not iridescent. The optical element can be disposed (e.g., affixed, attached, adhered, bonded, joined) to a surface of one or more components of the article, such as on the shoe upper and/or the sole of footwear.

In an aspect, the method of making the article can include contacting the optical element transfer structure (e.g., transfer medium including the optical element) with a surface of an article under a pressure and/or temperature condition for a time frame so that the optical element becomes disposed (e.g. affixed or adhered) to the surface of the article. The surface of the article can include a first thermoplastic material (e.g., thermoplastic material such as yarn, films, and the like), where the optical element is disposed to the thermoplastic material while under appropriate pressure and/or temperature conditions. The thermoplastic material can be reflowed while under the pressure and/or temperature conditions and disposes onto the optical element. Subsequently, the transfer medium can be removed, after cooling, from the article leaving the optical element or a portion thereof disposed onto the article. The optical element can impart structural color (e.g., single color, multicolor, iridescence) to the article. In one aspect, following application of the optical element on the surface of the article, the article can appear to be colored (i.e., to have a new, different color than the surface of the article had initially) without the application of pigments or dyes to the article, albeit pigments and/or dyes can be used in the design to select the desired structural color.

One type of transfer medium, among others, that can be used in accordance with the present disclosure is untextured or textured release paper. It has been found that application of the optical element from release paper (the optical element and the release paper forming the optical element transfer structure) results in an article. Using release paper as the transfer medium can be particularly suited for use with textiles including the thermoplastic polymeric material (e.g., thermoplastic yarn).

In one exemplary example, the optical element transfer structure can be used with an article such as a textile by applying the transfer structure to the surface of the textile, running the textile (including the thermoplastic material) and applied release paper through a set of nip rollers to reflow at least a portion of the thermoplastic material, and then removing the nip rollers and release paper to expose the optical element affixed to the textile. Application of the optical element can thus result in the textile having structural color (article) while the textile remains sufficiently flexible for use in articles of footwear, apparel, and the like.

The present disclosure provides for a method of making a component comprising: providing a transfer medium having a first surface and a second surface; and disposing an optical element onto the first surface of the transfer medium, wherein the optical element has a first side and a second side, wherein the first side of the optical element is disposed on the first surface of the transfer medium.

The present disclosure provides for a method of making an article comprising: providing an optical element transfer structure having a first side and a second side, wherein the first side of the optical element transfer structure includes a transfer medium, and the second side of the optical element transfer structure includes an optical element; contacting at least a portion of the second side of the optical element transfer structure with a first surface of a component of an article; disposing at least a portion of the optical element onto the first surface of the component; and removing the transfer medium from the optical element so that the portion of the optical element remains disposed on the component; wherein the optical element, as disposed to the article, imparts a structural color. The present disclosure provides for an article comprising a product of the method described above and herein.

The present disclosure provides for an optical element transfer structure comprising: a transfer medium having a first surface and a second surface; and an optical element disposed on at least a portion of the first surface of the transfer medium, wherein the optical element includes an optical layer.

The present disclosure provides for an article comprising: a component having a first surface; an optical element disposed to the first surface of the component; and a transfer medium releasably coupled with the optical element.

The present disclosure provides for an article comprising: a component having a first surface, the first surface comprising a first thermoplastic material; and an optical element disposed to the first thermoplastic material, wherein the optical element imparts a structural color to the component.

Now having described embodiments of the present disclosure generally, additional discussion regarding embodiments will be described in greater details.

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method may be carried out in the order of events recited or in any other order that is logically possible.

Embodiments of the present disclosure will employ, unless otherwise indicated, techniques of material science, chemistry, textiles, polymer chemistry, and the like, which are within the skill of the art. Such techniques are explained fully in the literature.

Unless otherwise defined, all technical and scientific terms used herein have the same meaning as commonly understood by one of ordinary skill in the art of material science, chemistry, textiles, polymer chemistry, and the like. Although methods and materials similar or equivalent to those described herein can be used in the practice or testing of the present disclosure, suitable methods and materials are described herein.

As used in the specification and the appended claims, the singular forms "a," "an," and "the" may include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

The present disclosure is directed to methods of forming optical element transfer structures and methods of using optical element transfer structures to form an article having structural color. The optical element transfer structure can include a transfer medium and an optical element disposed thereon. The present disclosure provides for methods of transferring the optical element or portions thereon onto the article using the optical element transfer structure. The surface of the article can be defined by a thermoplastic polymeric material. The optical element (e.g., a single or multilayer reflector or a multilayer filter) as disposed on an article can produce optical effects such as structural color on a surface of the article.

The method of making transferring the optical element can include contacting the optical element transfer structure (e.g., transfer medium including the optical element) with a surface of an article under conditions and for a time frame so that the optical element becomes disposed (e.g., affixed or adhered) to the surface of the article. In an embodiment, the surface of the article can include the thermoplastic material or materials having thermoplastic material on one or more surfaces, where the optical element is disposed to the thermoplastic material while under appropriate conditions. The thermoplastic material can be reflowed while under appropriate conditions to dispose the optical element onto the thermoplastic material. Subsequently, the transfer medium can be removed, after cooling, from the article leaving the optical element or a portion thereof disposed onto the article.

Articles of the present disclosure include the optical element as transferred from the optical element transfer structure that has the characteristic of producing optical effects such as structural color. The optical element includes at least one optical layer (e.g., a multilayer reflector or a multilayer filter) optionally in combination with a textured surface (e.g., integral to the optical element or as part of the surface of the article), optionally with a primer layer, optionally with a protective layer, or optionally with any combination of the textured surface, the primer layer, and the protective layer. The optical element or the combination of the optical element optionally with the textured surface and/or primer layer impart structural color (e.g., single color, multicolor, iridescent), to the article. Following disposing of the optical element onto the article, the article appears to be colored (i.e., to have a new, different color (e.g., in hue or otherwise defined herein) than the surface of the article had prior to the disposing) without the application of pigments or dyes to the article. However, pigments and/or dyes can be used in conjunction with the structural color structure to produce aesthetically pleasing effects.

In an aspect, the article including the transferred optical element can include footwear, apparel (e.g., shirts, jerseys, pants, shorts, gloves, glasses, socks, hats, caps, jackets, undergarments), containers (e.g., backpacks, bags), and upholstery for furniture (e.g., chairs, couches, car seats), bed coverings (e.g., sheets, blankets), table coverings, towels, flags, tents, sails, and parachutes. In addition, the transferred optical element can be used with or disposed on textiles or other items such as striking devices (e.g., bats, rackets, sticks, mallets, golf clubs, paddles, etc.), athletic equipment (e.g., golf bags, baseball and football gloves, soccer ball restriction structures), protective equipment (e.g., pads, helmets, guards, visors, masks, goggles, etc.), locomotive equipment (e.g., bicycles, motorcycles, skateboards, cars, trucks, boats, surfboards, skis, snowboards, etc.), balls or pucks for use in various sports, fishing or hunting equipment, furniture, electronic equipment, construction materials, eyewear, timepieces, jewelry, and the like.

Referring to FIGS. 1A-1M, the optical element of the present disclosure may be disclosed on many types of articles, including footwear, apparel, athletic equipment, container, electronic equipment, and vision wear. The optical element is represented by hashed areas 12A'/12M'-12A"/12M". The location of the optical element is provided only to indicate one possible area that the optical element can be located. Also, two locations are illustrated in the figures, but this is done only for illustration purposes as the articles can include one or a plurality of optical elements, where the size and location can be determined based on the item. The optical element(s) located on each item can represent a number, letter, symbol, design, emblem, graphic mark, icon, logo, or the like.

In an aspect, the article can include footwear. The footwear can be designed for a variety of uses, such as sporting, athletic, military, work-related, recreational, or casual use. Primarily, the article of footwear is intended for outdoor use on unpaved surfaces (in part or in whole), such as on a ground surface including one or more of grass, turf, gravel, sand, dirt, clay, mud, and the like, whether as an athletic performance surface or as a general outdoor surface. However, the article of footwear may also be desirable for indoor applications, such as indoor sports including dirt playing surfaces for example (e.g., indoor baseball fields with dirt infields).

The article of footwear can be designed for use in outdoor sporting activities, such as global football/soccer, golf, American football, rugby, baseball, running, track and field, cycling (e.g., road cycling and mountain biking), and the like. The article of footwear can optionally include traction elements (e.g., lugs, cleats, studs, and spikes as well as tread patterns) to provide traction on soft and slippery surfaces, where components of the present disclosure can be used or applied between or among the traction elements and optionally on the sides of the traction elements but on the surface of the traction element that contacts the ground or surface. Cleats, studs and spikes are commonly included in footwear designed for use in sports such as global football/soccer, golf, American football, rugby, baseball, and the like, which are frequently played on unpaved surfaces. Lugs and/or exaggerated tread patterns are commonly included in footwear including boots design for use under rugged outdoor conditions, such as trail running, hiking, and military use.

The article can be an article of apparel (i.e., a garment). The article of apparel can be an article of apparel designed for athletic or leisure activities. The article of apparel can be an article of apparel designed to provide protection from the elements (e.g., wind and/or rain), or from impacts.

The article can be an article of sporting equipment. The article of sporting equipment can be designed for use in indoor or outdoor sporting activities, such as global football/soccer, golf, American football, rugby, baseball, running, track and field, cycling (e.g., road cycling and mountain biking), and the like.

As has been described herein, the structural color can include one of a number of colors. The "color" of an article as perceived by a viewer can differ from the actual color of the article, as the color perceived by a viewer is determined by the actual color of the article by the presence of optical elements which may absorb, refract, interfere with, or otherwise alter light reflected by the article, by the viewer's ability to detect the wavelengths of light reflected by the article, by the wavelengths of light used to illuminate the article, as well as other factors such as the coloration of the environment of the article, and the type of incident light (e.g., sunlight, fluorescent light, and the like). As a result, the color of an object as perceived by a viewer can differ from the actual color of the article.

Conventionally, color is imparted to man-made objects by applying colored pigments or dyes to the object. More recently, methods of imparting "structural color" to man-made objects have been developed. Structural color is color which is produced, at least in part, by microscopically structured surfaces that interfere with visible light contacting the surface. The structural color is color caused by physical phenomena including the scattering, refraction, reflection, interference, and/or diffraction of light, unlike color caused by the absorption or emission of visible light through coloring matters. For example, optical phenomena which impart structural color can include multilayer interference, thin-film interference, refraction, dispersion, light scattering, Mie scattering, diffraction, and diffraction grating. In various aspects described herein, structural color imparted to an article can be visible to a viewer having 20/20 visual acuity and normal color vision from a distance of about 1 meter from the article.

As described herein, structural color is produced, at least in part, by the optical element, as opposed to the color being produced solely by pigments and/or dyes. The coloration of an article can be due solely to structural color (i.e., the article, a colored portion of the article, or a colored outer layer of the article can be substantially free of pigments and/or dyes). Structural color can also be used in combination with pigments and/or dyes, for example, to alter all or a portion of a structural color.

"Hue" is commonly used to describe the property of color which is discernible based on a dominant wavelength of visible light, and is often described using terms such as magenta, red, orange, yellow, green, cyan, blue, indigo, violet, etc. or can be described in relation (e.g., as similar or dissimilar) to one of these. The hue of a color is generally considered to be independent of the intensity or lightness of the color. For example, in the Munsell color system, the properties of color include hue, value (lightness) and chroma (color purity). Particular hues are commonly associated with particular ranges of wavelengths in the visible spectrum: wavelengths in the range of about 700 to 635 nanometers are associated with red, the range of about 635 to 590 nanometers is associated with orange, the range of about 590 to 560 nanometers is associated with yellow, the range of about 560 to 520 nanometers is associated with green, the range of about 520 to 490 nanometers is associated with cyan, the range of about 490 nanometers to 450 nanometers is associated with blue, and the range of about 450 to 400 nanometers is associated with violet.

The color (including the hue) of an article as perceived by a viewer can differ from the actual color of the article. The color as perceived by a viewer depends not only on the physics of the article, but also its environment, and the characteristics of the perceiving eye and brain. For example, as the color perceived by a viewer is determined by the actual color of the article (e.g., the color of the light leaving the surface of the article), by the viewer's ability to detect the wavelengths of light reflected or emitted by the article, by the wavelengths of light used to illuminate the article, as well as other factors such as the coloration of the environment of the article, and the type of incident light (e.g., sunlight, fluorescent light, and the like). As a result, the color of an object as perceived by a viewer can differ from the actual color of the article.

When used in the context of structural color, one can characterize the hue of an article, i.e., an article that has been structurally colored by incorporating an optical element into the article, based on the wavelengths of light the structurally-colored portion of the article absorbs and reflects (e.g., linearly and non-linearly). While the optical element may impart a first structural color, the presence of an optional textured surface and/or primer layer can alter the structural color. Other factors such as coatings or transparent elements may further alter the perceived structural color. The hue of the structurally colored article can include any of the hues described herein as well as any other hues or combination of hues. The structural color can be referred to as a "single hue" (i.e., the hue remains substantially the same, regardless of the angle of observation and/or illumination), or "multi-hued" (i.e., the hue varies depending upon the angle of observation and/or illumination). The multihued structural color can be iridescent (i.e., the hue changes gradually over two or more hues as the angle of observation or illumination changes). The hue of an iridescent multihued structural color can change gradually across all the hues in the visible spectrum (e.g., like a "rainbow") as the angle of observation or illumination changes. The hue of an iridescent multihued structural color can change gradually across a limited number of hues in the visible spectrum as the angle of observation or illumination changes, in other words, one or more hues in the visible spectrum (e.g., red, orange, yellow, etc.) are not observed in the structural color as the angle of observation or illumination changes. Only one hue, or substantially one hue, in the visible spectrum may be present for a single-hued structural color. The hue of a multihued structural color can change more abruptly between a limited number of hues (e.g., between 2-8 hues, or between 2-4 hues, or between 2 hues) as the angle of observation or illumination changes.

The structural color can be a multi-hued structural color in which two or more hues are imparted by the structural color.

The structural color can be iridescent multi-hued structural color in which the hue of the structural color varies over a wide number of hues (e.g., 4, 5, 6, 7, 8 or more hues) when viewed at a single viewing angle, or when viewed from two or more different viewing angles that are at least 15 degrees apart from each other.

The structural color can be limited iridescent multi-hue structural color in which the hue of the structural color varies, or varies substantially (e.g., about 90 percent, about 95 percent, or about 99 percent) over a limited number of hues (e.g, 2 hues, or 3 hues) when viewed from two or more different viewing angles that are at least 15 degrees apart from each other. In some aspects, a structural color having limited iridescence is limited to two, three or four hues selected from the RYB primary colors of red, yellow and blue, optionally the RYB primary and secondary colors of red, yellow, blue, green, orange and purple, or optionally the RYB primary, secondary and tertiary colors of red, yellow, blue, green, orange purple, green-yellow, yellow-orange, orange-red, red-purple, purple-blue, and blue-green.

The structural color can be single-hue angle-independent structural color in which the hue, the hue and value, or the hue, value and chroma of the structural color is independent of or substantially (e.g., about 90 percent, about 95 percent, or about 99 percent) independent of the angle of observation. For example, the single-hue angle-independent structural color can display the same hue or substantially the same hue when viewed from at least 3 different angles that are at least 15 degrees apart from each other (e.g., single-hue structural color).

The structural color imparted can be a structural color having limited iridescence such that, when each color observed at each possible angle of observation is assigned to a single hue selected from the group consisting of the primary, secondary and tertiary colors on the red yellow blue (RYB) color wheel, for a single structural color, all of the assigned hues fall into a single hue group, wherein the single hue group is one of a) green-yellow, yellow, and yellow-orange; b) yellow, yellow-orange and orange; c) yellow-orange, orange, and orange-red; d) orange-red, and red-purple; e) red, red-purple, and purple; f) red-purple, purple, and purple-blue; g) purple, purple-blue, and blue; h) purple-blue, blue, and blue-green; i) blue, blue-green and green; and j) blue-green, green, and green-yellow. In other words, in this example of limited iridescence, the hue (or the hue and the value, or the hue, value and chroma) imparted by the structural color varies depending upon the angle at which the structural color is observed, but the hues of each of the different colors viewed at the various angles of observations varies over a limited number of possible hues. The hue visible at each angle of observation can be assigned to a single primary, secondary or tertiary hue on the red yellow blue (RYB) color wheel (i.e., the group of hues consisting of red, yellow, blue, green, orange purple, green-yellow, yellow-orange, orange-red, red-purple, purple-blue, and blue-green). For example, while a plurality of different colors are observed as the angle of observation is shifted, when each observed hue is classified as one of red, yellow, blue, green, orange purple, green-yellow, yellow-orange, orange-red, red-purple, purple-blue, and blue-green, the list of assigned hues includes no more than one, two, or three hues selected from the list of RYB primary, secondary and tertiary hues. In some examples of limited iridescence, all of the assigned hues fall into a single hue group selected from hue groups a)-j), each of which include three adjacent hues on the RYB primary, secondary and tertiary color wheel. For example, all of the assigned hues can be a single hue within hue group h) (e.g., blue), or some of the assigned hues can represent two hues in hue group h) (e.g., purple-blue and blue), or can represent three hues in hue group h) (e.g., purple-blue, blue, and blue-green).

Similarly, other properties of the structural color, such as the lightness of the color, the saturation of the color, and the purity of the color, among others, can be substantially the same regardless of the angle of observation or illumination, or can vary depending upon the angle of observation or illumination. The structural color can have a matte appearance, a glossy appearance, or a metallic appearance, or a combination thereof.

As discussed above, the color (including hue) of an article can vary depending upon the angle at which the article is observed or illuminated. The hue or hues of an article can be determined by observing the article, or illuminating the article, at a variety of angles using constant lighting conditions. As used herein, the "angle" of illumination or viewing is the angle measured from an axis or plane that is orthogonal to the surface. The viewing or illuminating angles can be set between about 0 and 180 degrees. The viewing or illuminating angles can be set at 0 degrees, 15 degrees, 30 degrees, 45 degrees, 60 degrees, and –15 degrees and the color can be measured using a colorimeter or spectrophotometer (e.g., Konica Minolta), which focuses on a particular area of the article to measure the color. The viewing or illuminating angles can be set at 0 degrees, 15 degrees, 30 degrees, 45 degrees, 60 degrees, 75 degrees, 90 degrees, 105 degrees, 120 degrees, 135 degrees, 150 degrees, 165 degrees, 180 degrees, 195 degrees, 210 degrees, 225 degrees, 240 degrees, 255 degrees, 270 degrees, 285 degrees, 300 degrees, 315 degrees, 330 degrees, and 345 degrees and the color can be measured using a colorimeter or spectrophotometer. In a particular example of a multihued article colored using only structural color, when measured at 0 degrees, 15 degrees, 30 degrees, 45 degrees, 60 degrees, and –15 degrees, the hues measured for article consisted of "blue" at three of the measurement angles, "blue-green" at 2 of the measurement angles and "purple" at one of the measurement angles.

In other embodiments, the color (including hue, value and/or chroma) of an article does not change substantially, if at all, depending upon the angle at which the article is observed or illuminated. In instances such as this the structural color can be an angle-independent structural color in that the hue, the hue and value, or the hue, value and chroma observed is substantially independent or is independent of the angle of observation.

Various methodologies for defining color coordinate systems exist. One example is L*a*b* color space, where, for a given illumination condition, L* is a value for lightness, and a* and b* are values for color-opponent dimensions based on the CIE coordinates (CIE 1976 color space or CIELAB). In an embodiment, an article having structural color can be considered as having a "single" color when the change in color measured for the article is within about 10% or within about 5% of the total scale of the a* or b* coordinate of the L*a*b* scale (CIE 1976 color space) at three or more measured observation or illumination angles selected from measured at observation or illumination angles of 0 degrees, 15 degrees, 30 degrees, 45 degrees, 60 degrees, and –15 degrees. In certain embodiments, colors which, when measured and assigned values in the L*a*b* system that differ by at least 5 percent of the scale of the a* and b* coordinates, or by at least 10 percent of the scale of the a* and b* coordinates, are considered to be different colors. The article can have a change of less than about 40%, or less than about 30%, or less than about 20%, or less than about 10%, of the total scale of the a* coordinate or b* coordinate of the L*a*b* scale (CIE 1976 color space) at three or more measured observation or illumination angles.

A change in color between two measurements in the CIELAB space can be determined mathematically. For example, a first measurement has coordinates $L_1^*$, $a_1^*$ and $b_1^*$, and a second measurement has coordinates $L_2^*$, $a_2^*$ and $b_2^*$. The total difference between these two measurements on the CIELAB scale can be expressed as $\Delta E^*_{ab}$, which is calculated as follows: $\Delta E^*_{ab} = [(L_1^*-L_2^*)^2+(a_1^*-a_2^*)^2+(b_1^*-b_2^*)^2]^{1/2}$. Generally speaking, if two colors have a $\Delta E^*_{ab}$ of less than or equal to 1, the difference in color is not perceptible to human eyes, and if two colors have a $\Delta E^*_{ab}$ of greater than 100 the colors are considered to be opposite colors, while a $\Delta E^*_{ab}$ of about 2-3 is considered the threshold for perceivable color difference. In certain embodiments, a structurally colored article having structural color can be considered as having a "single" color when the $\Delta E^*_{ab}$ is less than 60, or less than 50, or less than 40, or less than 30, between three or more measured observation or illumination angles selected from measured at observation or illumination angles of 0 degrees, 15 degrees, 30 degrees, 45 degrees, 60 degrees, and –15 degrees. The article can have a $\Delta E^*_{ab}$ that is less than about 100, or less than about 80, or less than about 60, between two or more measured observation or illumination angles.

Another example of a color scale is the CIELCH color space, where, for a given illumination condition, L* is a value for lightness, C* is a value for chroma, and h° denotes a hue as an angular measurement. In an embodiment, an article having structural color can be considered as having a "single" color when the color measured for the article is less than 10 degrees different or less than 5 degrees different at the h° angular coordinate of the CIELCH color space, at three or more measured observation or illumination angles selected from measured at observation or illumination angles of 0 degrees, 15 degrees, 30 degrees, 45 degrees, 60 degrees, and –15 degrees. In certain embodiments, colors which, when measured and assigned values in the CIELCH system that vary by at least 45 degrees in the h° measurements, are considered to be different colors The article can have a change of less than about 60 degrees, or less than about 50 degrees, or less than about 40 degrees, or less than about 30 degrees, or less than about 20 degrees, or less than about 10 degrees, in the h° measurements of the CIELCH system at three or more measured observation or illumination angles.

Another system for characterizing color includes the "PANTONE" Matching System (Pantone LLC, Carlstadt, N.J., USA), which provides a visual color standard system to provide an accurate method for selecting, specifying, broadcasting, and matching colors through any medium. In an example, an article having a structural color can be considered as having a "single" color when the color measured for the article is within a certain number of adjacent standards, e.g., within 20 adjacent PANTONE standards, at three or more measured observation or illumination angles selected from 0 degrees, 15 degrees, 30 degrees, 45 degrees, 60 degrees, and −15 degrees Now having described color, additional details regarding the optical element are provided. As described herein, the article includes the optical element. The optical element includes at least one optical layer. The optical element that can be or include a single or multilayer reflector or a multilayer filter. The optical element can function to modify the light that impinges thereupon so that structural color is imparted to the article. The optical element can include at least one optical layer and optionally one or more additional layers (e.g., a protective layer, the textured layer, the primer layer, a polymer layer, and the like).

The method of making the structurally colored article can include disposing (e.g., affixing, attaching, bonding, fastening, joining, appending, connecting, binding, and operably disposing etc.) the optical element onto an article (e.g., an article of footwear, an article of apparel, an article of sporting equipment, etc.). The article includes a component, and the component has a surface upon which the optical element can be disposed. The surface of the article can be made of a material such as a thermoplastic material or thermoset material, as described herein. For example, the article has a surface including a thermoplastic material (i.e., a first thermoplastic material), for example an externally-facing surface of the component or an internally-facing surface of the component (e.g., an externally-facing surface or an internally-facing surface a bladder). The optical element can be disposed onto the thermoplastic material, for example.

In an aspect, the temperature of at least a portion of the first side of the article including the thermoplastic material is increased to a temperature at or above creep relaxation temperature ($T_{cr}$), Vicat softening temperature ($T_{vs}$), heat deflection temperature ($T_{hd}$), and/or melting temperature ($T_m$) of the thermoplastic material, for example to soften or melt the thermoplastic material. The temperature can be increased to a temperature at or above the creep relaxation temperature. The temperature can be increased to a temperature at or above the Vicat softening temperature. The temperature can be increased to a temperature at or above the heat deflection temperature. The temperature can be increased to a temperature at or above the melting temperature. While the temperature of the at least a portion of the first side of the article is at or above the increased temperature (e.g., at or above the creep relaxation temperature, the heat deflection temperature, the Vicat softening temperature, or the melting temperature of the thermoplastic material), the optical element is disposed on (e.g., affixed to) the thermoplastic material within the at least a portion of the first side of the article. Following the disposing (e.g., affixing), the temperature of the thermoplastic material is decreased to a temperature below its creep relaxation temperature to at least partially re-solidify the thermoplastic material. The thermoplastic material can be actively cooled (e.g., removing the source that increases the temperature and actively (e.g., flowing cooler gas adjacent the article reducing the temperature of the thermoplastic material) or passively cooled (e.g., removing the source that increases the temperature and allowing the thermoplastic layer to cool on its own).

The method of making the article can include disposing (e.g., affixing, attaching, bonding, fastening, joining, appending, connecting, binding) the optical element onto an article (e.g., an article of footwear, an article of apparel, an article of sporting equipment, etc.). The article includes a component, and the component has a surface upon which the optical element can be disposed. The surface of the article can be made of a material such as a thermoplastic material or thermoset material, as described herein. For example, the article has a surface including a thermoplastic material (i.e., a first thermoplastic material), for example an externally-facing surface of the component or an internally-facing surface of the component (e.g., an externally-facing surface or an internally-facing surface a bladder). The optical element can be disposed onto the thermoplastic material, for example.

The optical element has a first side (including the outer surface) and a second side opposing the first side (including the opposing outer surface), where the first side or the second side is adjacent the article. For example, when the optical element is used in conjunction with a component having internally-facing and externally-facing surfaces, such as a film or a bladder, the first side of the optical element can be disposed on the internally-facing surface of the component, such as in the following order: second side of the optical element/core of the optical element/first side of the optical element/internally-facing surface of the component/core of the component/externally-facing surface of the component. Alternatively, the second side the optical element can be disposed on the internally-facing surface of the component, such as in the following order: first side of the optical element/core of the optical element/second side of the optical element/internally-facing surface of the component/core of the component wall/externally-facing surface of the component. In another example, the first side of the optical element can be disposed on the externally-facing surface of the component, such as in the following order: internally-facing surface of the component/core of the component/externally-facing surface of the component/first side of the optical element/core of the optical element/second side of the optical element. Similarly, the second side of the optical element can be disposed on the externally-facing surface of the component, such as in the following order: internally-facing surface of the component/core of the component/externally-facing surface of the component/second side of the optical element/core of the optical element/first side of the optical element. In examples where the optional textured surface, the optional primer layer, or both are present, the textured surface and/or the primer layer can be located at the interface between the surface of the component and a side of the optical element.

The optical element or layers or portions thereof (e.g., optical layer) can be formed using known techniques such as physical vapor deposition, electron beam deposition, atomic layer deposition, molecular beam epitaxy, cathodic arc deposition, pulsed laser deposition, sputtering deposition (e.g., radio frequency, direct current, reactive, non-reactive), chemical vapor deposition, plasma-enhanced chemical vapor deposition, low pressure chemical vapor deposition and wet chemistry techniques such as layer-by-layer deposition, sol-gel deposition, Langmuir blodgett, and the like. The temperature of the first side can be adjusted using the technique to form the optical element and/or a separate system to adjust the temperature. Additional details are provided herein.

The optical layer(s) of the optical element can comprise a multilayer reflector. The multilayer reflector can be configured to have a certain reflectivity at a given wavelength of light (or range of wavelengths) depending, at least in part, on the material selection, thickness and number of the layers of the multilayer reflector. In other words, one can carefully select the materials, thicknesses, and numbers of the layers of a multilayer reflector and optionally its interaction with one or more other layers, so that it can reflect a certain wavelength of light (or range of wavelengths), to produce a desired structural color. The optical layer can include at least two adjacent layers, where the adjacent layers have different refractive indices. The difference in the index of refraction of adjacent layers of the optical layer can be about 0.0001 to 50 percent, about 0.1 to 40 percent, about 0.1 to 30 percent, about 0.1 to 20 percent, about 0.1 to 10 percent (and other ranges there between (e.g., the ranges can be in increments of 0.0001 to 5 percent)). The index of refraction depends at least in part upon the material of the optical layer and can range from 1.3 to 2.6.

The optical layer can include 2 to 20 layers, 2 to 10 layer, 2 to 6 layers, or 2 to 4 layers. Each layer of the optical layer can have a thickness that is about one-fourth of the wavelength of light to be reflected to produce the desired structural color. Each layer of the optical layer can have a thickness of about 10 to 500 nanometers or about 90 to 200 nanometers. The optical layer can have at least two layers, where adjacent layers have different thicknesses and optionally the same or different refractive indices.

The optical element can comprise a multilayer filter. The multilayer filter destructively interferes with light that impinges upon the structure or article, where the destructive interference of the light and optionally interaction with one or more other layers or structures (e.g., a multilayer reflector, a textured structure) impart the structural color. In this regard, the layers of the multilayer filter can be designed (e.g., material selection, thickness, number of layer, and the like) so that a single wavelength of light, or a particular range of wavelengths of light, make up the structural color. For example, the range of wavelengths of light can be limited to a range within plus or minus 30 percent or a single wavelength, or within plus or minus 20 percent of a single wavelength, or within plus or minus 10 percent of a single wavelength, or within plus or minus 5 percent or a single wavelength. The range of wavelengths can be broader to produce a more iridescent structural color.

The optical layer(s) can include multiple layers where each layer independently comprises a material selected from: the transition metals, the metalloids, the lanthanides, and the actinides, as well as nitrides, oxynitrides, sulfides, sulfates, selenides, and tellurides of these. The material can be selected to provide an index of refraction that when optionally combined with the other layers of the optical element achieves the desired result. One or more layers of the optical layer can be made of liquid crystals. Each layer of the optical layer can be made of liquid crystals. One or more layers of the optical layer can be made of a material such as: silicon dioxide, titanium dioxide, zinc sulfide, magnesium fluoride, tantalum pentoxide, aluminum oxide, or a combination thereof. Each layer of the optical layer can be made of a material such as: silicon dioxide, titanium dioxide, zinc sulfide, magnesium fluoride, tantalum pentoxide, aluminum oxide, or a combination thereof.

The optical element can be uncolored (e.g., no pigments or dyes added to the structure or its layers), colored (e.g., pigments and/or dyes are added to the structure or its layers (e.g., dark or black color)), reflective, and/or transparent (e.g., percent transmittance of 75 percent or more). The surface of the component upon which the optical element is disposed can be uncolored (e.g., no pigments or dyes added to the material), colored (e.g., pigments and/or dyes are added to the material (e.g., dark or black color)), reflective, and/or transparent (e.g., percent transmittance of 75 percent or more).

The optical layer(s) can be formed in a layer-by-layer manner, where each layer has a different index of refraction. Each layer of the optical layer can be formed using known techniques such as physical vapor deposition including: chemical vapor deposition, pulsed laser deposition, evaporative deposition, sputtering deposition (e.g., radio frequency, direct current, reactive, non-reactive), plasma enhanced chemical vapor deposition, electron beam deposition, atomic layer deposition, molecular beam epitaxy, cathodic arc deposition, low pressure chemical vapor deposition and wet chemistry techniques such as layer by layer deposition, sol-gel deposition, Langmuir blodgett and the like.

As mentioned above, the optical element can include one or more layers in addition to the optical layer(s). The optical element has a first side (e.g, the side having a surface) and a second side (e.g., the side having a surface), where the first side or the second side is adjacent the surface of the component. The one or more other layers of the optical element can be on the first side and/or the second side of the optical element. For example, the optical element can include a protective layer and/or a polymeric layer such as a thermoplastic polymeric layer, where the protective layer and/or the polymeric layer can be on one or both of the first side and the second side of the optical element. In another example, the optical element can include a primer layer as described herein. One or more of the optional other layers can include a textured surface. Alternatively or in addition, one or more optical layers of the optical element can include a textured surface.

A protective layer can be disposed on the first and/or second side of the optical layer to protect the optical layer. The protective layer is more durable or more abrasion resistant than the optical layer. The protective layer is optically transparent to visible light. The protective layer can be on the first side of the optical element to protect the optical layer. All or a portion of the protective layer can include a dye or pigment in order to alter an appearance of the structural color. The protective layer can include silicon dioxide, glass, combinations of metal oxides, or mixtures of polymers. The protective layer can have a thickness of about 3 nanometers to 1 millimeter.

The protective layer can be formed using physical vapor deposition, chemical vapor deposition, pulsed laser deposition, evaporative deposition, sputtering deposition (e.g., radio frequency, direct current, reactive, non-reactive), plasma enhanced chemical vapor deposition, electron beam deposition, cathodic arc deposition, low pressure chemical vapor deposition and wet chemistry techniques such as layer by layer deposition, sol-gel deposition, Langmuir blodgett, and the like. Alternatively or in addition, the protective layer can be applied by spray coating, dip coating, brushing, spin coating, doctor blade coating, and the like.

A polymeric layer can be disposed on the first and/or the second side of the optical element. The polymeric layer can be used to dispose the optical element onto an article, such as, for example, when the article does not include a thermoplastic material to adhere the optical element. The polymeric layer can comprise a polymeric adhesive material, such as a hot melt adhesive. The polymeric layer can be a thermoplastic material and can include one or more layers. The thermoplastic material can be any one of the thermoplastic material described herein. The polymeric layer can be applied using various methodologies, such as spin coating, dip coating, doctor blade coating, and so on. The polymeric layer can have a thickness of about 3 nanometer to 1 millimeter.

As described above, one or more embodiments of the present disclosure provide articles that incorporate the optical element (e.g., single or multilayer structures) on a side of a component of the article to impart structural color. The optical element can be disposed onto the thermoplastic material of the side of the article, and the side of the article can include a textile, including a textile comprising the thermoplastic material.

Having described the optical element, additional details will now be described for the optional textured surface. As described herein, the component includes the optical element and the optical element can include at least one optical layer and optionally a textured surface. The textured surface can be a surface of a textured structure or a textured layer. The textured surface may be provided as part of the optical element. For example, the optical element may comprise a textured layer or a textured structure that comprises the textured surface. The textured surface may be formed on the first or second side of the optical element. For example, a side of the optical element can be formed or modified to provide a textured surface, or a textured layer or textured structure can be disposed on (e.g., affixed to) the first or second side of the optical element. The textured surface may be provided as part of the component to which the optical element is disposed. For example, the optical element may be disposed onto the surface of the component where the surface of the component is a textured surface, or the surface of the component includes a textured structure or a textured layer.

The textured surface (or a textured structure or textured layer including the textured surface) may be provided as a feature on or part of another medium, such as a transfer medium, and imparted to a side or layer of the optical element or to the surface of the component. For example, a mirror image or relief form of the textured surface may be provided on the side of a transfer medium, and the transfer medium contacts a side of the optical element or the surface of the component in a way that imparts the textured surface to the optical element or article. While the various embodiments herein may be described with respect to a textured surface of the optical element, it will be understood that the features of the textured surface, or a textured structure or textured layer, may be imparted in any of these ways.

The textured surface can contribute to the structural color resulting from the optical element. As described herein, structural coloration is imparted, at least in part, due to optical effects resulting from physical phenomena such as scattering, diffraction, reflection, interference or unequal refraction of light rays from an optical element. The textured surface (or its mirror image or relief) can include a plurality of profile features and flat or planar areas. The plurality of profile features included in the textured surface, including their size, shape, orientation, spatial arrangement, etc., can affect the light scattering, diffraction, reflection, interference and/or refraction resulting from the optical element. The flat or planar areas included in the textured surface, including their size, shape, orientation, spatial arrangement, etc., can affect the light scattering, diffraction, reflection, interference and/or refraction resulting from the optical element. The desired structural color can be designed, at least in part, by adjusting one or more of properties of the profile features and/or flat or planar areas of the textured surface.

The profile features can extend from a side of the flat areas, so as to provide the appearance of projections and/or depressions therein. In an aspect, the flat areas can be flat planar areas. A profile feature may include various combinations of projections and depressions. For example, a profile feature may include a projection with one or more depressions therein, a depression with one or more projections therein, a projection with one or more further projections thereon, a depression with one or more further depressions therein, and the like. The flat areas do not have to be completely flat and can include texture, roughness, and the like. The texture of the flat areas may not contribute much, if any, to the imparted structural color. The texture of the flat areas typically contributes to the imparted structural color. For clarity, the profile features and flat areas are described in reference to the profile features extending above the flat areas, but the inverse (e.g., dimensions, shapes, and the like) can apply when the profile features are depressions in the textured surface.

The textured surface can comprise a thermoplastic material. The profile features and the flat areas can be formed using a thermoplastic material. For example, when the thermoplastic material is heated above its softening temperature a textured surface can be formed in the thermoplastic material such as by molding, stamping, printing, compressing, cutting, etching, vacuum forming, etc., the thermoplastic material to form profile features and flat areas therein. The textured surface can be imparted on a side of a thermoplastic material. The textured surface can be formed in a layer of thermoplastic material. The profile features and the flat areas can be made of the same thermoplastic material or a different thermoplastic material.

The textured surface generally has a length dimension extending along an x-axis, and a width dimension extending along a z-axis, and a thickness dimension extending along a y-axis. The textured surface has a generally planar portion extending in a first plane that extends along the x-axis and the z-axis. A profile feature can extend outward from the first plane, so as to extend above or below the plane x. A profile feature may extend generally orthogonal to the first plane, or at an angle greater to or less than 90 degrees to the first plane.

The dimension (e.g., length, width, height, diameter, depending upon the shape of the profile feature) of each profile feature can be within the nanometer to micrometer range. A textured surface can have a profile feature and/or flat area with a dimension of about 10 nanometers to about 500 micrometers. The profile feature can have dimensions in the nanometer range, e.g., from about 10 nanometers to about 1000 nanometers. All of the dimensions of the profile feature (e.g., length, width, height, diameter, depending on the geometry) can be in the nanometer range, e.g., from about 10 nanometers to about 1000 nanometers. The textured surface can have a plurality of profile features having dimensions that are 1 micrometer or less. In this context, the phrase "plurality of the profile features" is meant to mean that about 50 percent or more, about 60 percent or more, about 70 percent or more, about 80 percent or more, about 90 percent or more, or about 99 percent or more of the profile features have a dimension in this range. The profile features can have a ratio of width:height and/or length:height dimensions of about 1:2 and 1:100, or 1:5 and 1:50, or 1:5 and 1.10.

The textured surface can have a profile feature and/or flat area with a dimension within the micrometer range of dimensions. A textured surface can have a profile feature and/or flat area with a dimension of about 1 micrometer to about 500 micrometers. All of the dimensions of the profile feature (e.g., length, width, height, diameter, depending on the geometry) can be in the micrometer range, e.g., from about 1 micrometer to about 500 micrometers. The textured surface can have a plurality of profile features having dimensions that are from about 1 micrometer to about 500 micrometer. In this context, the phrase "plurality of the profile features" is meant to mean that about 50 percent or more, about 60 percent or more, about 70 percent or more, about 80 percent or more, about 90 percent or more, or about 99 percent or more of the profile features have a dimension in this range. The height of the profile features (or depth if depressions) can be about 0.1 and 50 micrometers, about 1 to 5 micrometers, or 2 to 3 micrometers. The profile features can have a ratio of width:height and/or length:height dimensions of about 1:2 and 1:100, or 1:5 and 1:50, or 1:5 and 1:10.

A textured surface can have a plurality of profile features having a mixture of size dimensions within the nanometer to micrometer range (e.g., a portion of the profile features are on the nanometer scale and a portion of the profile features are on the micrometer scale). A textured surface can have a plurality of profile features having a mixture of dimensional ratios. The textured surface can have a profile feature having one or more nanometer-scale projections or depressions on a micrometer-scale projection or depression.

The profile feature can have height and width dimensions that are within a factor of three of each other (0.33w≤h≤3w where w is the width and h is the height of the profile feature) and/or height and length dimensions that are within a factor of three of each other (0.33l≤h≤3l where l is the length and h is the height of the profile feature). The profile feature can have a ratio of length:width that is from about 1:3 to about 3:1, or about 1:2 to about 2:1, or about 1:1.5 to about 1.5:1, or about 1:1.2 to about 1.2:1, or about 1:1. The width and length of the profile features can be substantially the same or different.

The profile features can have a certain spatial arrangement. The spatial arrangement of the profile features may be uniform, such as spaced evenly apart or forming a pattern. The spatial arrangement can be random. Adjacent profile features can be about 1 to 100 micrometers apart or about 5 to 100 micrometers apart. The desired spacing can depend, at least in part, on the size and/or shape of the profile structures and the desired structural color effect.

The profile features can have a certain cross-sectional shape (with respect to a plane parallel the first plane). The textured surface can have a plurality of profile features having the same or similar cross-sectional shape. The textured surface has a plurality of profile features having a mixture of different cross-sectional shapes. The cross-sectional shapes of the profile features can include polygonal (e.g., square or triangle or rectangle cross section), circular, semi-circular, tubular, oval, random, high and low aspect ratios, overlapping profile features, and the like.

The profile feature (e.g., about 10 nanometers to 500 micrometers) can include an upper, convexly curved surface. The curved surface may extend symmetrically either side of an uppermost point.

The profile feature can include protrusions from the textured surface. The profile feature can include indents (hollow areas) formed in the textured surface. The profile feature can have a smooth, curved shape (e.g., a polygonal cross-section with curved corners).

The profile features (whether protrusions or depressions) can be approximately conical or frusto-conical (i.e. the projections or indents may have horizontally or diagonally flattened tops) or have an approximately part-spherical surface (e.g., a convex or concave surface respectively having a substantially even radius of curvature).

The profile features may have one or more sides or edges that extend in a direction that forms an angle to the first plane of the textured surface. The angle between the first plane and a side or edge of the profile feature is about 45 degrees or less, about 30 degrees or less, about 25 degrees or less, or about 20 degrees or less. The one or more sides or edges may extend in a linear or planar orientation, or may be curved so that the angle changes as a function of distance from the first plane. The profile features may have one or more sides that include step(s) and/or flat side(s). The profile feature can have one or more sides (or portions thereof) that can be orthogonal or perpendicular to the first plane of the textured surface, or extend at an angle of about 10 degrees to 89 degrees to the first plane (90 degrees being perpendicular or orthogonal to the first plane)). The profile feature can have a side with a stepped configuration, where portions of the side can be parallel to the first plane of the textured surface or have an angle of about 1 degrees to 179 degrees (0 degrees being parallel to the first plane)).

The textured surface can have profile features with varying shapes (e.g., the profile features can vary in shape, height, width and length among the profile features) or profile features with substantially uniform shapes and/or dimensions. The structural color produced by the textured surface can be determined, at least in part, by the shape, dimensions, spacing, and the like, of the profile features.

The profile features can be shaped so as to result in a portion of the surface (e.g., about 25 to 50 percent or more) being about normal to the incoming light when the light is incident at the normal to the first plane of the textured surface. The profile features can be shaped so as to result in a portion of the surface (e.g., about 25 to 50 percent or more) being about normal to the incoming light when the light is incident at an angle of up to 45 degrees to the first plane of the textured surface.

The spatial orientation of the profile features on the textured surface is set to reduce distortion effects, e.g., resulting from the interference of one profile feature with another in regard to the structural color of the structure. Since the shape, dimension, relative orientation of the profile features can vary considerably across the textured surface, the desired spacing and/or relative positioning for a particular area (e.g., in the micrometer range or about 1 to 10 square micrometers) having profile features can be appropriately determined. As discussed herein, the shape, dimension, relative orientation of the profile features affect the contours of the optical element (or optical layer), so the dimensions (e.g., thickness), index of refraction, number of layers in the optical element are considered when designing the textured side of the texture layer.

The profile features are located in nearly random positions relative to one another across a specific area of the textured surface (e.g., in the micrometer range or about 1 to 10 square micrometers to centimeter range or about 0.5 to 5 square centimeters, and all range increments therein), where the randomness does not defeat the purpose of producing the structural color. In other words, the randomness is consistent with the spacing, shape, dimension, and relative orientation of the profile features, the dimensions (e.g., thickness), index of refraction, and number of layers in the optical layer, and the like, with the goal to achieve the structural color.

The profile features are positioned in a set manner relative to one another across a specific area of the textured surface to achieve the purpose of producing the structural color. The relative positions of the profile features do not necessarily follow a pattern, but can follow a pattern consistent with the desired structural color. As mentioned above and herein, various parameters related to the profile features, flat areas, and optical element (e.g., optical layer) can be used to position the profile features in a set manner relative to one another.

The textured surface can include micro and/or nanoscale profile features that can form gratings (e.g., a diffractive grating), photonic crystal structure, a selective mirror structure, crystal fiber structures, deformed matrix structures, spiraled coiled structures, surface grating structures, and combinations thereof. The textured surface can include micro and/or nanoscale profile features that form a grating having a periodic or non-periodic design structure to impart the structural color. The micro and/or nanoscale profile features can have a peak-valley pattern of profile features and/or flat areas to produce the desired structural color. The grading can be an Echelette grating.

Figure 2A:
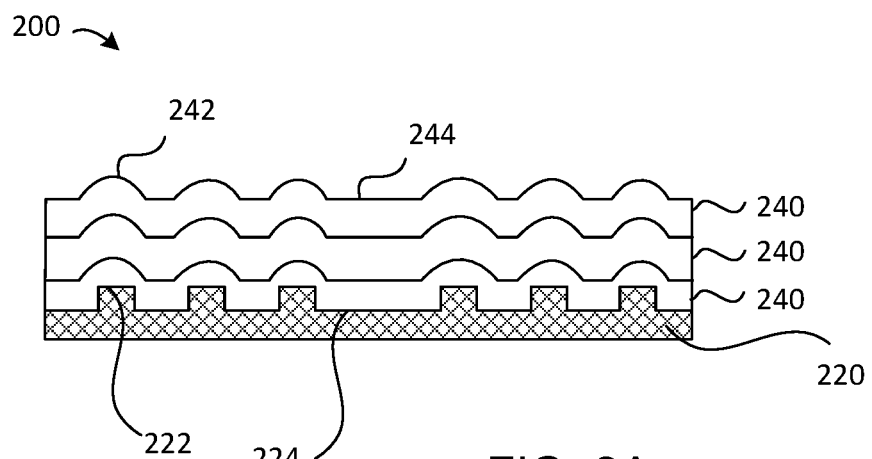
FIGS. 2A-2B illustrate side views of exemplary optical elements of the present disclosure.
Figure 2B:
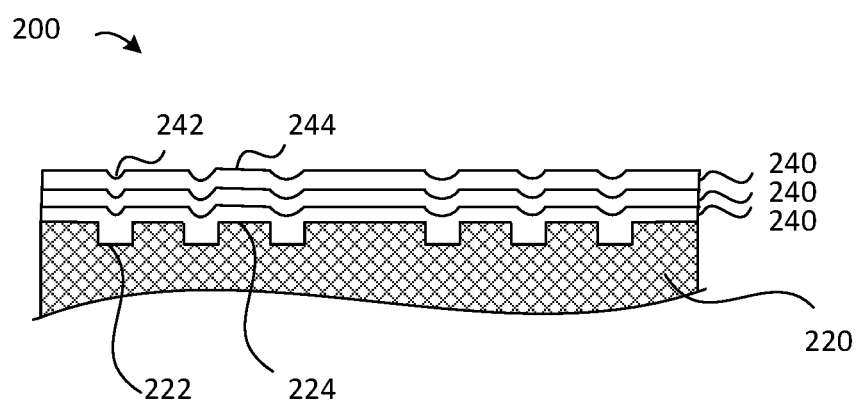

The profile features and the flat areas of the textured surface in the optical element can appear as topographical undulations in each layer of the optical layer. For example, referring to FIGS. 2A and 2B, an optical element 200 includes a textured structure 220 having a plurality of profile features 222 and flat areas 224. As described herein, one or more of the profile features 222 can be projections from a surface of the textured structure 220 (as shown in FIG. 2A), and/or one or more of the profile features 222 can be depressions in a surface of the textured structure 220 (as shown in FIG. 2B). One or more optical layers 240 are disposed on the side or surface of the textured structure 220 having the profile features 222 and flat areas 224. In some embodiments, the resulting topography of the one or more optical layers 240 is not identical to the topography of the textured structure 220, but rather, the one or more optical layers 240 can have elevated or depressed regions 242 which are either elevated or depressed relative to the height of the planar regions 244 and which roughly correspond to the location of the profile features 222 of the textured structure 220. The one or more optical layers 240 also have planar regions 244 that roughly correspond to the location of the flat areas 224 of the textured structure 220. Due to the presence of the elevated or depressed regions 242 and the planar regions 244, the resultant overall topography of the optical layer 240 can be that of an undulating or wave-like structure. The dimension, shape, and spacing of the profile features along with the number of layers of the optical layer, the thickness of each of the layers, refractive index of each layer, and the type of material, can be used to produce an optical element which results in a particular structural color.

Now having described the optical element and the textured surface, additional details will be provided for the optionally present primer layer. The optical element is used to produce the structural color, where the optical element can include (e.g., as part of the optical element) or use the primer layer to produce the structural color. As described herein, the optical element can also include (e.g., as part of optical element) the optional textured surface, such as a texture layer and/or a textured structure. The combination of the optical element and the optional texture layer and the optional primer layer can form a structural color structure having one of the following designs: texture layer/primer layer/optical element or primer layer/texture layer/optical element. The primer layer can have a thickness of about 3 nanometers to 200 micrometers, or about 1 to about 200 micrometers, or about 10 to about 100 micrometers, or about 10 to about 80 micrometers. The structural color structure can include the combination of the primer layer, the optical element, and (optionally) textured surface. Selection of variables associated with the primer layer, texture layer, and the optical element, can be used to control and select the desired structural color.

The structural color structure can include the primer layer, the textured surface (optionally), and the optical element (e.g., optical layer), where the optical element is disposed on the textured surface or the primer layer, depending upon the design. The combination of the primer layer, the textured surface, and the optical element imparts structural color, to the article, where the structural color is different than the primer color, optionally with or without the application of pigments or dyes to the article. The optical element can be disposed onto the primer layer and/or the textured surface. The primer layer can include the textured surface as described herein. For example, the primer layer can be formed in a way so that it has the textured surface.

The primer layer can include a paint layer (e.g., dyes, pigments, and a combination thereof), an ink layer, a reground layer, an at least partially degraded polymer layer, a metal layer, an oxide layer, or a combination thereof. The primer layer can have a light or dark color. The primer layer can have a dark color. For example the dark color can be selected from: black, shades of black, brown, dark shades of brown, dark shades of red, dark shades of orange, dark shades of yellow, dark shades of green, dark shades of cyan, dark shades of blue, dark shades of violet, grey, dark shades of gray, dark shades of magenta, dark shades of indigo, tones, tints, shades, or hues of any of these, and a combination thereof. The color can be defined using the L*a*b system, where the value of L* can be about 70 or less, about 60 or less, about 50 or less, about 40 or less, or about 30 or less and a* and b* coordinate values can vary across the positive and negative value scales.

The primer layer can be formed using digital printing, inkjet printing, offset printing, pad printing, screen printing, flexographic printing, heat transfer printing, physical vapor deposition including: chemical vapor deposition, pulsed laser deposition, evaporative deposition, sputtering deposition (radio frequency, direct current, reactive, non-reactive), plasma enhanced chemical vapor deposition, electron beam deposition, cathodic arc deposition, low pressure chemical vapor deposition and wet chemistry techniques such as layer by layer deposition, sol-gel deposition, or Langmuir blodgett. Alternatively or in addition, the primer layer can be applied by spray coating, dip coating, brushing, spin coating, doctor blade coating, and the like.

The primer layer can have a percent transmittance of about 40% or less, about 30% or less, about 20% or less, about 15% or less, about 10% or less, about 5% or less, or about 1% or less, where "less" can include about 0% (e.g., 0 to 0.01 or 0 to 0.1), about 1%, about 2.5%, or about 5%.

The primer layer can include a paint composition that, upon applying to the structure, forms a thin layer. The thin layer can be a solid film having a dark color, such as those described above. The paint composition can include known paint compositions that can comprise one or more of the following components: one or more paint resin, one or more polymers, one or more dyes, and one or more pigments as well as water, film-forming solvents, drying agents, thickeners, surfactants, anti-skinning agents, plasticizers, mildewcides, mar-resistant agents, anti-flooding agents, and combinations thereof.

The primer layer can comprise a reground, and at least partially degraded, polymer layer. The reground, and at least partially degraded, polymer layer can have a dark color, such as those described above.

The primer layer can include a metal layer or the oxide layer. The metal layer or the oxide layer can have a dark color, such as those described above. The oxide layer can be a metal oxide, a doped metal oxide, or a combination thereof. The metal layer, the metal oxide or the doped metal oxide can include the following: the transition metals, the metalloids, the lanthanides, and the actinides, as well as nitrides, oxynitrides, sulfides, sulfates, selenides, tellurides and a combination of these. The metal oxide can include titanium oxide, aluminum oxide, silicon dioxide, tin dioxide, chromia, iron oxide, nickel oxide, silver oxide, cobalt oxide, zinc oxide, platinum oxide, palladium oxide, vanadium oxide, molybdenum oxide, lead oxide, and combinations thereof as well as doped versions of each. In some aspects, the primer layer can consist essentially of a metal oxide. In some aspects, the primer layer can consist essentially of titanium dioxide or silicon dioxide. In some aspects, the primer layer can consist essentially of titanium dioxide. The metal oxide can be doped with water, inert gasses (e.g., argon), reactive gasses (e.g., oxygen or nitrogen), metals, small molecules, and a combination thereof. In some aspects, the primer layer can consist essentially of a doped metal oxide or a doped metal oxynitride or both.

The primer layer can be a coating on the surface of the article. The coating can be chemically bonded (e.g., covalently bonded, ionically bonded, hydrogen bonded, and the like) to the surface of the article. The coating has been found to bond well to a surface made of a polymeric material. In an example, the surface of the article can be made of a polymeric material such as a polyurethane, including a thermoplastic polyurethane (TPU), as those described herein.

The coating can be a crosslinked coating that includes one or more colorants such as solid pigment particles or dye. The crosslinked coating can be a matrix of crosslinked polymers (e.g., a crosslinked polyester polyurethane polymer or copolymer). The colorants can be entrapped in the coating, including entrapped in the matrix of crosslinked polymers. The solid pigment particles or dye can be physically entrapped in the crosslinked polymer matrix, can be chemically bonded (e.g., covalently bonded, ionically bonded, hydrogen bonded, and the like, with the coating including the polymeric matrix or with the material forming the surface of the article to which the coating is applied), or a combination of physically bonded and chemically bonded with the coating or article. The crosslinked coating can have a thickness of about 0.01 micrometers to 1000 micrometers.

The coating can be a product (or also referred to as "crosslinked product") of crosslinking a polymeric coating composition. The polymeric coating composition can include one or more colorants (e.g., solid pigment particles or dye) in a dispersion of polymers. The dispersion of polymers can include a water-borne dispersion of polymers such as a water-borne dispersion of polyurethane polymers, including polyester polyurethane copolymers). The water-borne dispersion of polymers can be crosslinked to entrap the colorants. The colorants can be physically entrapped in the crosslinked product, can be chemically bonded (e.g., covalently bonded, ionically bonded, hydrogen bonded, and the like, with the crosslinked copolymer matrix), or can be both physically bonded and chemically bonded with the crosslinked product. The product can be formed by crosslinking the polymeric coating composition. The product can have a thickness of about 0.01 micrometer to 1000 micrometers.

The coating can include colorants such a pigment (e.g., a solid pigment particle) or a dye. The solid pigment particles can include inorganic pigments such as metal and metal oxides such as homogeneous inorganic pigments, core-shell pigments and the like, as well as carbon pigments (e.g., carbon black), clay earth pigments, and ultramarine pigments. The solid pigment particles can be biological or organic pigments. The solid pigment particles can be of a type known in the art as an extender pigment, which include, but are not limited to, calcium carbonate, calcium silicate, mica, clay, silica, barium sulfate and the like. The amount of the solid pigment particles sufficient to achieve the desired color intensity, shade, and opacity, can be in amounts up to about 5 percent to 25 percent or more by weight of the coating. The pigments can include those sold by KP Pigments such as pearl pigments, color shift pigments (e.g., CALYPSO, JEDI, VERO, BLACKHOLE, LYNX, ROSE GOLD, and the like), hypershift pigments, interference pigments and the like.

The colorant can be a dye such as an anionic dye, a cationic dye, a direct dye, a metal complex dye, a basic dye, a disperse dye, a solvent dye, a polymeric dye, a polymeric dye colorant, or a nonionic dye, where the coating can include one or more dyes and/or types of dyes. The dye can be a water-miscible dye. The dye can be a solubilized dye. The anionic dye can be an acid dye. The dye can be applied separately from the coating (e.g., either before or after the coating is applied and/or cured).

Acid dyes are water-soluble anionic dyes. Acid dyes are available in a wide variety, from dull tones to brilliant shades. Chemically, acid dyes include azo, anthraquinone and triarylmethane compounds. The "Color Index" (C.I.), published jointly by the Society of Dyers and Colourists (UK) and by the American Association of Textile Chemists and Colorists (USA), is the most extensive compendium of dyes and pigments for large scale coloration purposes, including 12000 products under 2000 C.I. generic names. In the C.I. each compound is presented with two numbers referring to the coloristic and chemical classification. The "generic name" refers to the field of application and/or method of coloration, while the other number is the "constitution number." Examples of acid dyes include Acid Yellow 1, 17, 23, 25, 34, 42, 44, 49, 61, 79, 99, 110, 116, 127, 151, 158:1, 159, 166, 169, 194, 199, 204, 220, 232, 241, 246, and 250; Acid Red, 1, 14, 17, 18, 42, 57, 88, 97, 118, 119, 151, 183, 184, 186, 194, 195, 198, 211, 225, 226, 249, 251, 257, 260, 266, 278, 283, 315, 336, 337, 357, 359, 361, 362, 374, 405, 407, 414, 418, 419, and 447; Acid Violet 3, 5, 7, 17, 54, 90, and 92; Acid Brown 4, 14, 15, 45, 50, 58, 75, 97, 98, 147, 160:1, 161, 165, 191, 235, 239, 248, 282, 283, 289, 298, 322, 343, 349, 354, 355, 357, 365, 384, 392, 402, 414, 420, 422, 425, 432, and 434; Acid Orange 3, 7, 10, 19, 33, 56, 60, 61, 67, 74, 80, 86, 94, 139, 142, 144, 154, and 162; Acid Blue 1, 7, 9, 15, 92, 133, 158, 185, 193, 277, 277:1, 314, 324, 335, and 342; Acid Green 1, 12, 68:1, 73, 80, 104, 114, and 119; Acid Black 1, 26, 52, 58, 60, 64, 65, 71, 82, 84, 107, 164, 172, 187, 194, 207, 210, 234, 235, and combinations of these. The acid dyes may be used singly or in any combination in the ink composition.

Acid dyes and nonionic disperse dyes are commercially available from many sources, including Dystar L.P., Charlotte, N.C. under the tradename TELON, Huntsman Corporation, Woodlands, Tex., USA under the tradename ERIONYL and TECTILON, BASF SE, Ludwigshafen, Germany under the tradename BASACID, and Bezema AG, Montlingen, Switzerland under the tradename Bemacid.

The colorant can include the dye and a quaternary (tetraalkyl) ammonium salt, in particular when the dye is acidic dye. The quaternary (tetraalkyl) ammonium salt can react with the dye (e.g., acid dye) to form a complexed dye that can be used in the coating. The "alkyl" group can include C1 to C10 alkyl groups. The quaternary (tetraalkyl) ammonium salt can be selected from soluble tetrabutylammonium compounds and tetrahexylammonium compounds. The counterion of the quaternary ammonium salt should be selected so that the quaternary ammonium salt forms a stable solution with the dye (e.g., anionic dye). The quaternary ammonium compound may be, for example, a halide (such as chloride, bromide or iodide), hydroxide, sulfate, sulfite, carbonate, perchlorate, chlorate, bromate, iodate, nitrate, nitrite, phosphate, phosphite, hexfluorophosphite, borate, tetrafluoroborate, cyanide, isocyanide, azide, thiosulfate, thiocyanate, or carboxylate (such as acetate or oxalate). The tetraalkylammonium compound can be or include a tetrabutylammonium halide or tetrahexylammonium halide, particularly a tetrabutylammonium bromide or chloride or a tetrahexylammonium bromide or chloride. The coating (e.g., coating, polymeric coating composition (prior to curing) can include about 1 to 15 weight percent of the quaternary ammonium salt. The molar ratio of the acid dye to the quaternary ammonium compound can range from about 3:1 to 1:3 or about 1.5:1 to 1:1.5.

The coating (e.g., coating, polymeric coating composition (prior to curing), monomers and/or polymers of the matrix of crosslinked polymers, or precursors of the coating) can include a cross-linker, which functions to crosslink the polymeric components of the coating. The cross-linker can be a water-borne cross-linker. The cross-linker can include one or more of the following: a polycarboxylic acid cross-linking agent, an aldehyde crosslinking agent, a polyisocyanate crosslinking agent, or a combination thereof. The polycarboxylic acid crosslinking agent can be a polycarboxylic acid having from 2 to 9 carbon atoms. For example, the cross-linker can include a polyacrylic acid, a polymaleic acid, a copolymer of acid, a copolymer of maleic acid, fumaric acid, or 1, 2, 3, 4-butanetetracarboxylic acid. The concentration of the cross-linker can be about 0.01 to 5 weight percent or 1 to 3 weight percent of the coating.

The coating (e.g., coating, polymeric coating composition (prior to curing), monomers and/or polymers of the matrix of crosslinked polymers, or precursors of the coating) can include a solvent. The solvent can be an organic solvent. The organic solvent can be a water-miscible organic solvent. The coating may not include water, or may be essentially free of water. For example, the solvent can be or includes acetone, ethanol, 2-propanol, ethyl acetate, isopropyl acetate, methanol, methyl ethyl ketone, 1-butanol, t-butanol, or any mixture thereof.

According to aspects of the disclosure, a method for making an article includes providing the optical element transfer structure comprising an optical element releasably coupled with a transfer medium, and then transferring the optical element to an article.

One type of transfer medium, among others, that can be used in accordance with the present disclosure is untextured or textured release paper. In an aspect, the transfer medium may have a first side that has a release material, and the optical element or a portion thereof may be disposed on the release material so that it may be removed from the transfer medium and affixed to an article. It has been found that application of the optical element from release paper (the optical element and the release paper forming the optical element transfer structure) results in an article having structural color. Using release paper as the transfer medium can be particularly suited for use with textiles including a thermoplastic polymeric material (e.g., thermoplastic yarn).

In an aspect, the transfer medium, or a layer on the surface of the transfer medium, can form a textured surface on the optical element. The transfer medium can include a textured layer (as part of the transfer medium or a layer formed thereon) having a textured surface, which is used to impart the textured surface in the optical element. For example, the transfer medium can have a first textured surface, and as a result of disposing the optical element on the first textured surface, the optical element may have a second textured surface that is an inverse or relief of the first textured surface.

In an aspect, the method of making the can include contacting the optical element transfer structure (e.g., transfer medium including the optical element with a surface of an article (or a component thereof) under a pressure and/or temperature condition for a time frame so that the optical element is disposed onto the surface of the article. The surface of the article can include a thermoplastic material (e.g., thermoplastic fiber, yarn, film, layer, skin), where the optical element is disposed to the thermoplastic material while under appropriate pressure and/or temperature conditions. The thermoplastic material can be reflowed while under the pressure and/or temperature conditions and is disposed onto the article. Subsequently, the transfer medium can be removed, after cooling, from the article leaving the optical element affixed to the article.

In one exemplary embodiment, the transfer medium (optical element transfer structure) can be used with the article such as a textile by applying the transfer medium to the surface of the textile, running the textile (including the thermoplastic material) and applied release paper through a set of nip rollers to reflow at least a portion of the thermoplastic material, and then removing the nip rollers and release paper to result in the optical element being affixed to the textile. Application of the optical element to the textile imparts structural color to the textile, while the textile remains sufficiently flexible for use in articles of footwear, apparel, and the like.

In an aspect, one method for making the optical element transfer structure includes providing a transfer medium having a first surface, and a second surface, and disposing an optical element on the first surface of the transfer medium. The optical element has a first side and a second side and the first side of the optical element is in contact with the first side of the transfer medium. In an aspect, the transfer medium can include a cellulose, such as a release paper. In an aspect one side of the transfer medium includes a release material comprising polyeolefins, silicones, polyurethanes, or a combination thereof. In some aspects, the release material may include a material having a softening or melting temperature such that when the release material is heated above the softening or melting temperature, the optical element may be more easily released from the transfer medium. For example, a release material may have a softening or melting temperature of from about 105 degrees C. to about 140 degrees C.

In an aspect, the optical element can be formed or disposed on the transfer medium, such as on the release material. Additional details regarding the optical element are provided herein. In some aspects, the first surface of the transfer medium, can be substantially flat, and the optical element is disposed on the flat first surface. In other aspects, the first surface of the transfer medium can be at least partially textured, and the optical element is disposed on the textured surface, which results in forming a texture on the surface of the optical element. If desired, an optional textured surface can alternatively be formed on a layer within the optical element, or on one or both surfaces of the optical element. In some aspects, an optional primer layer may be formed on the transfer medium. The primer layer may be formed on the first or second side of the optical element. Additional details regarding the primer layer are provided herein.

In an aspect, a method of making an article includes contacting a region of the second side of the optical element transfer structure with a first side of a component of an article and disposed at least a portion of the optical element to the first side of the component. The optical element transfer structure can be removed so that the portion of the optical element remains disposed onto the component.

In another aspect, disposing at least a portion of the optical element to the first side of the article can include increasing a temperature of the second side of the optical element transfer structure (e.g., the thermoplastic material) and applying pressure to the second side of the optical element transfer structure. The temperature of the second side of the optical element transfer structure can then be decreased. The optical element transfer structure can be removed during or after the temperature is decreased so that the portion of the optical element remains disposed onto the component.

Now having described the method in general, other aspects of the method or more particular aspects of the method will now be described. In an aspect, at least a portion of the optical element can be disposed onto the first side of the component of the article. In an aspect, disposing can include increasing a temperature of the second side of the optical element transfer structure, applying pressure to the second side of the optical element transfer structure, and/or decreasing the temperature of the second side of the optical element. In as aspect, during disposing, increasing of the temperature can be conducted prior to or concurrently with the contacting and the applying pressure, and prior to the decreasing the temperature, and decreasing the temperature is conducted prior to the removing. In an aspect, increasing the temperature can include increasing the temperature of the second side of the optical element transfer structure to a temperature above a softening or melting temperature of a release material of the optical element transfer structure.

In an aspect, the component of the article can be defined at least in part by a first thermoplastic material, and the optical element is disposed onto the first thermoplastic material. In an aspect, increasing the temperature can include increasing the temperature to a first temperature that is at or above a creep relaxation temperature, a heat deflection temperature, a Vicat softening temperature, or a melting temperature of the first thermoplastic material. While the temperature is at or above the first temperature, the optical element can be disposed onto the first thermoplastic material.

In another aspect, the method can include increasing a temperature of the component of the article to a first temperature that is at or above a creep relaxation temperature, a heat deflection temperature, a Vicat softening temperature, or a melting temperature of the first thermoplastic material. The temperature can be lowered to a second temperature that is below the creep relaxation temperature, the heat deflection temperature, the Vicat softening temperature, or the melting temperature of the first thermoplastic material to partially re-solidify the thermoplastic material and then the optical element can be disposed onto the thermoplastic material.

As described generally above, the thermoplastic material of the article can be reflowed before or during the time frame when the optical layer transfer structure (e.g., transfer medium) is in direct contact with the thermoplastic material of the surface of the article, optionally under pressure, to transfer the optical element to the surface of the first thermoplastic material of the article. The first thermoplastic material can be subject to heating before and/or during application of the transfer medium. As stated above, the temperature can be selected based on the composition of the first thermoplastic material, in particular the thermoplastic polymer. In some aspects, the first thermoplastic material has material has a creep relaxation temperature, a heat deflection temperature, a Vicat softening temperature, or a melting temperature of about 80 degrees C. to about 140 degrees C.

In an aspect, a pressure can be applied between the transfer medium and the first thermoplastic material of the article so that the transfer structure and the thermoplastic material are in direct contact with one another so that the optical element contacts and is disposed onto the first thermoplastic material. For example, the transfer structure and the thermoplastic material can be passed through a roller system (e.g., nip rolls) or other similar system that causes the transfer structure and the thermoplastic material to directly contact one another to disposed the optical element to the article.

Once the optical element is disposed on or affixed to the first thermoplastic material of the article, the transfer medium can be removed. In an aspect, the removal of the transfer medium can be performed after the first thermoplastic material, specifically the thermoplastic polymer, has cooled near or below one of the creep relaxation temperature, the heat deflection temperature, the Vicat softening temperature, or the melting temperature of the first thermoplastic material to partially re-solidify the first thermoplastic material.

In another aspect and as described generally above, the article may or may not include a thermoplastic material. In an aspect, the article (or component thereof) can include a first constituent comprising the first thermoplastic material. Disposing can include disposing the optical element to the first constituent. In some aspects, the first constituent can include an externally facing surface that comprises the first thermoplastic material and the optical element is disposed to the externally-facing surface. In some aspects, the first surface of the article (or component thereof) further includes a second constituent that is different from the first constituent, wherein the second constituent is selected from a group consisting of a first fiber or filament, a first yarn, a film, a textile, or a combination thereof, and during the disposing step, the optical element is not affixed to the second constituent. For example, the second constituent can comprise a polymeric material having a creep relaxation temperature, a heat deflection temperature, a Vicat softening temperature, or a melting temperature that is at least 20 degrees C. above the creep relaxation temperature, the heat deflection temperature, the Vicat softening temperature, or the melting temperature of the first thermoplastic material; and increasing the temperature of the first surface of the component to a first temperature does not result in softening or melting of the second constituent.

In instances where portions of the article do not include a thermoplastic material (e.g., second yarn) or only portions (e.g., select yarns (first yarn)) include the thermoplastic material, the optical element can include a thermoplastic layer that can applied against the surface of the article. In this regard, the thermoplastic material can be reflowed before or during the time frame when transfer medium is in direct contact with the surface of the article, optionally under pressure, to transfer the optical element to the article. The thermoplastic material can be subject to heating before and/or during application of the transfer medium. The temperature of the thermoplastic material is above a softening temperature so that the optical element becomes disposed onto the article. As stated above, the temperature can be selected based on the composition of the thermoplastic material, in particular the thermoplastic polymer.

In an aspect, a pressure can be applied between the transfer medium and the article so that the transfer medium and the thermoplastic material are in direct contact with one another so that the optical element adheres to the article. For example, the transfer medium and the article can be passed through a roller system (e.g., nip rolls) or other similar system that causes the transfer medium and the article to directly contact one another to affix the optical element to the article. Once the optical element is disposed on or affixed to the article, the transfer medium can be removed. In an aspect, the removal of the transfer medium can be performed after the thermoplastic material, specifically the thermoplastic polymer, has cooled near or below the softening temperature so that it is at least partially solidified and the article and the optical element are adhered to one another.

In another aspect, the method also includes contacting the second side of the optical layer onto a first side of an article. In an aspect, thermal energy and/or pressure can be applied to the second side transfer medium for a time frame to affix (e.g., adhered to or attached to one another) a portion of the optical layer to the article. Subsequently, the transfer medium is removed from the first side of the optical layer so that a portion of the optical layer remains affixed to the article.

In an aspect, the pressure applied, the thermal energy applied, and/or the time frame of the application can each vary depending upon the article, the transfer medium, and the like. In general, the pressure applied can be about 30 psi to 90 psi, or about 40 psi to about 80 psi. The thermal energy can raise the temperature of the article, in particular, the thermoplastic material of the article to near or above the softening temperature and/or melting temperature so that the optical element adheres to the article. In general, the temperature can depend upon the thermoplastic material selected and can be about 80° C. to about 140 psi. In general, the time frame can be from 2 seconds to 10 minutes or more. Any combination of pressure, temperature, and time can be used to affix the optical element to the article.

In some aspects, the first surface of the component, prior to the increasing its temperature, can have an externally-facing portion which comprises a plurality of fibers in a filamentous conformation that include the first thermoplastic material, and increasing the temperature to a first temperature at or above a creep relaxation temperature, a heat deflection temperature, a Vicat softening temperature, or a melting temperature of the first thermoplastic material results in a softening or melting the first thermoplastic material which alters the conformation of at least a portion of the fibers present on the externally-facing portion of the first surface so that they have a non-filamentous conformation, producing a non-filamentous region on the first surface of the component. In some aspects, the optical element may be disposed onto the first surface of the component while the temperature is at or above the first temperature. In other aspects, the temperature of the first surface of the component can be lowered to at least partially re-solidify the first thermoplastic material of the non-filamentous region, and then the optical element can be affixed to the non-filamentous region.

An aspect of the present disclosure includes a system for disposing the optical element to the thermoplastic material of the article to form the article. In an aspect, a first device can be configured to contact the optical element transfer structure to the surface of the article. In an aspect, the first device can be configured to apply the transfer medium against the article for a time frame, at a selected temperature, and/or at a selected pressure. In an aspect, the first device can be configured to remove the transfer medium, where the optical element is disposed onto the article. In an aspect, the first device is configured to reflow the thermoplastic material. In an aspect, the first device is configured to heat the thermoplastic material before, after, or both applying the transfer medium to the article, while optionally being able to apply a pressure (e.g., nip rolls) between the article and the transfer medium. In this regard, the first device can perform multiple tasks, for example at different stages on a production line.

Additional details are provided regarding the polymeric materials referenced herein for example, the polymers described in reference to the article, components of the article, structures, layers, films, bladders, foams, primer layer, coating, and like the.

Additional details are provided regarding the polymeric materials referenced herein for example, the polymers described in reference to the article, components of the article, structures, layers, films, bladders, foams, primer layer, coating, and like the. The polymer can be a thermoset polymer or a thermoplastic polymer. The polymer can be an elastomeric polymer, including an elastomeric thermoset polymer or an elastomeric thermoplastic polymer. The polymer can be selected from: polyurethanes (including elastomeric polyurethanes, thermoplastic polyurethanes (TPUs), and elastomeric TPUs), polyesters, polyethers, polyamides, vinyl polymers (e.g., copolymers of vinyl alcohol, vinyl esters, ethylene, acrylates, methacrylates, styrene, and so on), polyacrylonitriles, polyphenylene ethers, polycarbonates, polyureas, polystyrenes, co-polymers thereof (including polyester-polyurethanes, polyether-polyurethanes, polycarbonate-polyurethanes, polyether block polyamides (PEBAs), and styrene block copolymers), and any combination thereof, as described herein. The polymer can include one or more polymers selected from the group consisting of polyesters, polyethers, polyamides, polyurethanes, polyolefins copolymers of each, and combinations thereof.

The term "polymer" refers to a chemical compound formed of a plurality of repeating structural units referred to as monomers. Polymers often are formed by a polymerization reaction in which the plurality of structural units become covalently bonded together. When the monomer units forming the polymer all have the same chemical structure, the polymer is a homopolymer. When the polymer includes two or more monomer units having different chemical structures, the polymer is a copolymer. One example of a type of copolymer is a terpolymer, which includes three different types of monomer units. The co-polymer can include two or more different monomers randomly distributed in the polymer (e.g., a random co-polymer). Alternatively, one or more blocks containing a plurality of a first type of monomer can be bonded to one or more blocks containing a plurality of a second type of monomer, forming a block copolymer. A single monomer unit can include one or more different chemical functional groups.

Polymers having repeating units which include two or more types of chemical functional groups can be referred to as having two or more segments. For example, a polymer having repeating units of the same chemical structure can be referred to as having repeating segments. Segments are commonly described as being relatively harder or softer based on their chemical structures, and it is common for polymers to include relatively harder segments and relatively softer segments bonded to each other in a single monomeric unit or in different monomeric units. When the polymer includes repeating segments, physical interactions or chemical bonds can be present within the segments or between the segments or both within and between the segments. Examples of segments often referred to as hard segments include segments including a urethane linkage, which can be formed from reacting an isocyanate with a polyol to form a polyurethane. Examples of segments often referred to as soft segments include segments including an alkoxy functional group, such as segments including ether or ester functional groups, and polyester segments. Segments can be referred to based on the name of the functional group present in the segment (e.g., a polyether segment, a polyester segment), as well as based on the name of the chemical structure which was reacted in order to form the segment (e.g., a polyol-derived segment, an isocyanate-derived segment). When referring to segments of a particular functional group or of a particular chemical structure from which the segment was derived, it is understood that the polymer can contain up to 10 mole percent of segments of other functional groups or derived from other chemical structures. For example, as used herein, a polyether segment is understood to include up to 10 mole percent of non-polyether segments.

As previously described, the polymer can be a thermoplastic polymer. In general, a thermoplastic polymer softens or melts when heated and returns to a solid state when cooled. The thermoplastic polymer transitions from a solid state to a softened state when its temperature is increased to a temperature at or above its softening temperature, and a liquid state when its temperature is increased to a temperature at or above its melting temperature. When sufficiently cooled, the thermoplastic polymer transitions from the softened or liquid state to the solid state. As such, the thermoplastic polymer may be softened or melted, molded, cooled, re-softened or re-melted, re-molded, and cooled again through multiple cycles. For amorphous thermoplastic polymers, the solid state is understood to be the "rubbery" state above the glass transition temperature of the polymer. The thermoplastic polymer can have a melting temperature from about 90 degrees C. to about 190 degrees C. when determined in accordance with ASTM D3418-97 as described herein below, and includes all subranges therein in increments of 1 degree. The thermoplastic polymer can have a melting temperature from about 93 degrees C. to about 99 degrees C. when determined in accordance with ASTM D3418-97 as described herein below. The thermoplastic polymer can have a melting temperature from about 112 degrees C. to about 118 degrees C. when determined in accordance with ASTM D3418-97 as described herein below.

The glass transition temperature is the temperature at which an amorphous polymer transitions from a relatively brittle "glassy" state to a relatively more flexible "rubbery" state. The thermoplastic polymer can have a glass transition temperature from about −20 degrees C. to about 30 degrees C. when determined in accordance with ASTM D3418-97 as described herein below. The thermoplastic polymer can have a glass transition temperature (from about −13 degree C. to about −7 degrees C. when determined in accordance with ASTM D3418-97 as described herein below. The thermoplastic polymer can have a glass transition temperature from about 17 degrees C. to about 23 degrees C. when determined in accordance with ASTM D3418-97 as described herein below.

The thermoplastic polymer can have a melt flow index from about 10 to about 30 cubic centimeters per 10 minutes ($cm^3/10$ min) when tested in accordance with ASTM D1238-13 as described herein below at 160 degrees C. using a weight of 2.16 kilograms (kg). The thermoplastic polymer can have a melt flow index from about 22 $cm^3/10$ min to about 28 $cm^3/10$ min when tested in accordance with ASTM D1238-13 as described herein below at 160 degrees C. using a weight of 2.16 kg.

The thermoplastic polymer can have a cold Ross flex test result of about 120,000 to about 180,000 cycles without cracking or whitening when tested on a thermoformed plaque of the thermoplastic polymer in accordance with the cold Ross flex test as described herein below. The thermoplastic polymer can have a cold Ross flex test result of about 140,000 to about 160,000 cycles without cracking or whitening when tested on a thermoformed plaque of the thermoplastic polymer in accordance with the cold Ross flex test as described herein below.

The thermoplastic polymer can have a modulus from about 5 megaPascals (MPa) to about 100 MPa when determined on a thermoformed plaque in accordance with ASTM D412-98 Standard Test Methods for Vulcanized Rubber and Thermoplastic Rubbers and Thermoplastic Elastomers-Tension with modifications described herein below. The thermoplastic polymer can have a modulus from about 20 MPa to about 80 MPa when determined on a thermoformed plaque in accordance with ASTM D412-98 Standard Test Methods for Vulcanized Rubber and Thermoplastic Rubbers and Thermoplastic Elastomers-Tension with modifications described herein below.

The polymer can be a thermoset polymer. As used herein, a "thermoset polymer" is understood to refer to a polymer which cannot be heated and melted, as its melting temperature is at or above its decomposition temperature. A "thermoset material" refers to a material which comprises at least one thermoset polymer. The thermoset polymer and/or thermoset material can be prepared from a precursor (e.g., an uncured or partially cured polymer or material) using thermal energy and/or actinic radiation (e.g., ultraviolet radiation, visible radiation, high energy radiation, infrared radiation) to form a partially cured or fully cured polymer or material which no longer remains fully thermoplastic. In some cases, the cured or partially cured polymer or material may remain thermoelastic properties, in that it is possible to partially soften and mold the polymer or material at elevated temperatures and/or pressures, but it is not possible to melt the polymer or material. The curing can be promoted, for example, with the use of high pressure and/or a catalyst. In many examples, the curing process is irreversible since it results in cross-linking and/or polymerization reactions of the precursors. The uncured or partially cured polymers or materials can be malleable or liquid prior to curing. In some cases, the uncured or partially cured polymers or materials can be molded into their final shape, or used as adhesives. Once hardened, a thermoset polymer or material cannot be re-melted in order to be reshaped. The textured surface can be formed by partially or fully curing an uncured precursor material to lock in the textured surface.

Polyurethane

The polymer can be a polyurethane, such as a thermoplastic polyurethane (also referred to as "TPU"). Alternatively, the polymer can be a thermoset polyurethane. Additionally, polyurethane can be an elastomeric polyurethane, including an elastomeric TPU or an elastomeric thermoset polyurethane. The elastomeric polyurethane can include hard and soft segments. The hard segments can comprise or consist of urethane segments (e.g., isocyanate-derived segments). The soft segments can comprise or consist of alkoxy segments (e.g., polyol-derived segments including polyether segments, or polyester segments, or a combination of polyether segments and polyester segments). The polyurethane can comprise or consist essentially of an elastomeric polyurethane having repeating hard segments and repeating soft segments.

One or more of the polyurethanes can be produced by polymerizing one or more isocyanates with one or more polyols to produce polymer chains having carbamate linkages (—N(CO)O—) as illustrated below in Formula 1, where the isocyanate(s) each preferably include two or more isocyanate (—NCO) groups per molecule, such as 2, 3, or 4 isocyanate groups per molecule (although, mono-functional isocyanates can also be optionally included, e.g., as chain terminating units).

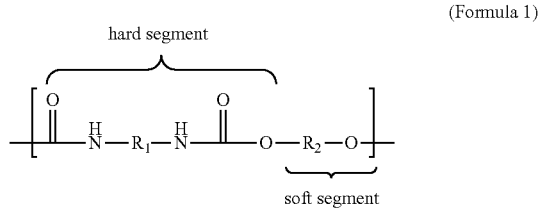

(Formula 1)

Each $R_1$ group and $R_2$ group independently is an aliphatic or aromatic group. Optionally, each $R_2$ can be a relatively hydrophilic group, including a group having one or more hydroxyl groups.

Additionally, the isocyanates can also be chain extended with one or more chain extenders to bridge two or more isocyanates, increasing the length of the hard segment. This can produce polyurethane polymer chains as illustrated below in Formula 2, where $R_3$ includes the chain extender. As with each $R_1$ and $R_2$, each $R_3$ independently is an aliphatic or aromatic functional group.

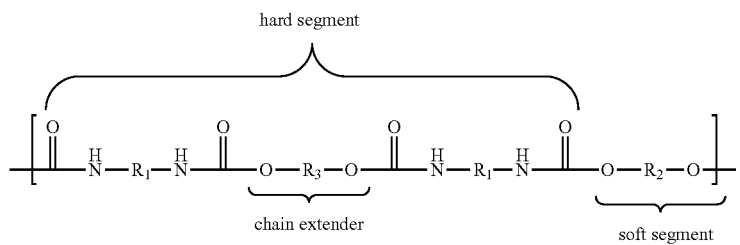

(Formula 2)

Each $R_1$ group in Formulas 1 and 2 can independently include a linear or branched group having from 3 to 30 carbon atoms, based on the particular isocyanate(s) used, and can be aliphatic, aromatic, or include a combination of aliphatic portions(s) and aromatic portion(s). The term "aliphatic" refers to a saturated or unsaturated organic molecule or portion of a molecule that does not include a cyclically conjugated ring system having delocalized pi electrons. In comparison, the term "aromatic" refers to an organic molecule or portion of a molecule having a cyclically conjugated ring system with delocalized pi electrons, which exhibits greater stability than a hypothetical ring system having localized pi electrons.

Each $R_1$ group can be present in an amount of about 5 percent to about 85 percent by weight, from about 5 percent to about 70 percent by weight, or from about 10 percent to about 50 percent by weight, based on the total weight of the reactant compounds or monomers which form the polymer.

In aliphatic embodiments (from aliphatic isocyanate(s)), each $R_1$ group can include a linear aliphatic group, a branched aliphatic group, a cycloaliphatic group, or combinations thereof. For instance, each $R_1$ group can include a linear or branched alkylene group having from 3 to 20 carbon atoms (e.g., an alkylene having from 4 to 15 carbon atoms, or an alkylene having from 6 to 10 carbon atoms), one or more cycloalkylene groups having from 3 to 8 carbon atoms (e.g., cyclopropyl, cyclobutyl, cyclopentyl, cyclohexyl, cycloheptyl, or cyclooctyl), and combinations thereof. The term "alkene" or "alkylene" as used herein refers to a bivalent hydrocarbon. When used in association with the term $C_n$ it means the alkene or alkylene group has "n" carbon atoms. For example, $C_{1-6}$ alkylene refers to an alkylene group having, e.g., 1, 2, 3, 4, 5, or 6 carbon atoms.

Examples of suitable aliphatic diisocyanates for producing the polyurethane polymer chains include hexamethylene diisocyanate (HDI), isophorone diisocyanate (IPDI), butylenediisocyanate (BDI), bisisocyanatocyclohexylmethane (HMDI), 2,2,4-trimethylhexamethylene diisocyanate (TMDI), bisisocyanatomethylcyclohexane, bisisocyanatomethyltricyclodecane, norbornane diisocyanate (NDI), cyclohexane diisocyanate (CHDI), 4,4'-dicyclohexylmethane diisocyanate (H12MDI), diisocyanatododecane, lysine diisocyanate, and combinations thereof.

The isocyanate-derived segments can include segments derived from aliphatic diisocyanate. A majority of the isocyanate-derived segments can comprise segments derived from aliphatic diisocyanates. At least 90% of the isocyanate-derived segments are derived from aliphatic diisocyanates. The isocyanate-derived segments can consist essentially of segments derived from aliphatic diisocyanates. The aliphatic diisocyanate-derived segments can be derived substantially (e.g., about 50 percent or more, about 60 percent or more, about 70 percent or more, about 80 percent or more, about 90 percent or more) from linear aliphatic diisocyanates. At least 80% of the aliphatic diisocyanate-derived segments can be derived from aliphatic diisocyanates that are free of side chains. The segments derived from aliphatic diisocyanates can include linear aliphatic diisocyanates having from 2 to 10 carbon atoms.

When the isocyanate-derived segments are derived from aromatic isocyanate(s)), each $R_1$ group can include one or more aromatic groups, such as phenyl, naphthyl, tetrahydronaphthyl, phenanthrenyl, biphenylenyl, indanyl, indenyl, anthracenyl, and fluorenyl. Unless otherwise indicated, an aromatic group can be an unsubstituted aromatic group or a substituted aromatic group, and can also include heteroaromatic groups. "Heteroaromatic" refers to monocyclic or polycyclic (e.g., fused bicyclic and fused tricyclic) aromatic ring systems, where one to four ring atoms are selected from oxygen, nitrogen, or sulfur, and the remaining ring atoms are carbon, and where the ring system is joined to the remainder of the molecule by any of the ring atoms. Examples of suitable heteroaryl groups include pyridyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, furanyl, quinolinyl, isoquinolinyl, benzoxazolyl, benzimidazolyl, and benzothiazolyl groups.

Examples of suitable aromatic diisocyanates for producing the polyurethane polymer chains include toluene diisocyanate (TDI), TDI adducts with trimethyloylpropane (TMP), methylene diphenyl diisocyanate (MDI), xylene diisocyanate (XDI), tetramethylxylylene diisocyanate (TMXDI), hydrogenated xylene diisocyanate (HXDI), naphthalene 1,5-diisocyanate (NDI), 1,5-tetrahydronaphthalene diisocyanate, para-phenylene diisocyanate (PPDI), 3,3'-dimethyldiphenyl-4, 4'-diisocyanate (DDDI), 4,4'-dibenzyl diisocyanate (DBDI), 4-chloro-1,3-phenylene diisocyanate, and combinations thereof. The polymer chains can be substantially free of aromatic groups.

The polyurethane polymer chains can be produced from diisocyanates including HMDI, TDI, MDI, $H_{12}$ aliphatics, and combinations thereof. For example, the polyurethane can comprise one or more polyurethane polymer chains produced from diisocyanates including HMDI, TDI, MDI, $H_{12}$ aliphatics, and combinations thereof.

Polyurethane chains which are at least partially crosslinked or which can be crosslinked, can be used in accordance with the present disclosure. It is possible to produce crosslinked or crosslinkable polyurethane chains by reacting multi-functional isocyanates to form the polyurethane. Examples of suitable triisocyanates for producing the polyurethane chains include TDI, HDI, and IPDI adducts with trimethyloylpropane (TMP), uretdiones (i.e., dimerized isocyanates), polymeric MDI, and combinations thereof.

The $R_3$ group in Formula 2 can include a linear or branched group having from 2 to 10 carbon atoms, based on the particular chain extender polyol used, and can be, for example, aliphatic, aromatic, or an ether or polyether. Examples of suitable chain extender polyols for producing the polyurethane include ethylene glycol, lower oligomers of ethylene glycol (e.g., diethylene glycol, triethylene glycol, and tetraethylene glycol), 1,2-propylene glycol, 1,3-propylene glycol, lower oligomers of propylene glycol (e.g., dipropylene glycol, tripropylene glycol, and tetrapropylene glycol), 1,4-butylene glycol, 2,3-butylene glycol, 1,6-hexanediol, 1,8-octanediol, neopentyl glycol, 1,4-cyclohexanedimethanol, 2-ethyl-1,6-hexanediol, 1-methyl-1,3-propanediol, 2-methyl-1,3-propanediol, dihydroxyalkylated aromatic compounds (e.g., bis(2-hydroxyethyl) ethers of hydroquinone and resorcinol, xylene-a,a-diols, bis(2-hydroxyethyl) ethers of xylene-a,a-diols, and combinations thereof.

The $R_2$ group in Formula 1 and 2 can include a polyether group, a polyester group, a polycarbonate group, an aliphatic group, or an aromatic group. Each $R_2$ group can be present in an amount of about 5 percent to about 85 percent by weight, from about 5 percent to about 70 percent by weight, or from about 10 percent to about 50 percent by weight, based on the total weight of the reactant monomers.

At least one $R_2$ group of the polyurethane includes a polyether segment (i.e., a segment having one or more ether groups). Suitable polyether groups include, but are not limited to, polyethylene oxide (PEO), polypropylene oxide (PPO), polytetrahydrofuran (PTHF), polytetramethylene oxide (PTMO), and combinations thereof. The term "alkyl" as used herein refers to straight chained and branched saturated hydrocarbon groups containing one to thirty carbon atoms, for example, one to twenty carbon atoms, or one to ten carbon atoms. When used in association with the term $C_n$ it means the alkyl group has "n" carbon atoms. For example, $C_4$ alkyl refers to an alkyl group that has 4 carbon atoms. $C_{1-7}$ alkyl refers to an alkyl group having a number of carbon atoms encompassing the entire range (i.e., 1 to 7 carbon atoms), as well as all subgroups (e.g., 1-6, 2-7, 1-5, 3-6, 1, 2, 3, 4, 5, 6, and 7 carbon atoms). Non-limiting examples of alkyl groups include, methyl, ethyl, n-propyl, isopropyl, n-butyl, sec-butyl (2-methylpropyl), t-butyl (1,1-dimethylethyl), 3,3-dimethylpentyl, and 2-ethylhexyl. Unless otherwise indicated, an alkyl group can be an unsubstituted alkyl group or a substituted alkyl group.

In some examples of the polyurethane, the at least one $R_2$ group includes a polyester group. The polyester group can be derived from the polyesterification of one or more dihydric alcohols (e.g., ethylene glycol, 1,3-propylene glycol, 1,2-propylene glycol, 1,4-butanediol, 1,3-butanediol, 2-methylpentanediol, 1,5,diethylene glycol, 1,5-pentanediol, 1,5-hexanediol, 1,2-dodecanediol, cyclohexanedimethanol, and combinations thereof) with one or more dicarboxylic acids (e.g., adipic acid, succinic acid, sebacic acid, suberic acid, methyladipic acid, glutaric acid, pimelic acid, azelaic acid, thiodipropionic acid and citraconic acid and combinations thereof). The polyester group also can be derived from polycarbonate prepolymers, such as poly(hexamethylene carbonate) glycol, poly(propylene carbonate) glycol, poly(tetramethylene carbonate)glycol, and poly(nonanemethylene carbonate) glycol. Suitable polyesters can include, for example, polyethylene adipate (PEA), poly(1,4-butylene adipate), poly(tetramethylene adipate), poly(hexamethylene adipate), polycaprolactone, polyhexamethylene carbonate, poly(propylene carbonate), poly(tetramethylene carbonate), poly(nonanemethylene carbonate), and combinations thereof.

At least one $R_2$ group can include a polycarbonate group. The polycarbonate group can be derived from the reaction of one or more dihydric alcohols (e.g., ethylene glycol, 1,3-propylene glycol, 1,2-propylene glycol, 1,4-butanediol, 1,3-butanediol, 2-methylpentanediol, 1,5, diethylene glycol, 1,5-pentanediol, 1,5-hexanediol, 1,2-dodecanediol, cyclohexanedimethanol, and combinations thereof) with ethylene carbonate.

The aliphatic group can be linear and can include, for example, an alkylene chain having from 1 to 20 carbon atoms or an alkenylene chain having from 1 to 20 carbon atoms (e.g., methylene, ethylene, propylene, butylene, pentylene, hexylene, heptylene, octylene, nonylene, decylene, undecylene, dodecylene, tridecylene, ethenylene, propenylene, butenylene, pentenylene, hexenylene, heptenylene, octenylene, nonenylene, decenylene, undecenylene, dodecenylene, tridecenylene). The term "alkene" or "alkylene"

refers to a bivalent hydrocarbon. The term "alkenylene" refers to a bivalent hydrocarbon molecule or portion of a molecule having at least one double bond.

The aliphatic and aromatic groups can be substituted with one or more pendant relatively hydrophilic and/or charged groups. The pendant hydrophilic group can include one or more (e.g., 2, 3, 4, 5, 6, 7, 8, 9, 10 or more) hydroxyl groups. The pendant hydrophilic group includes one or more (e.g., 2, 3, 4, 5, 6, 7, 8, 9, 10 or more) amino groups. In some cases, the pendant hydrophilic group includes one or more (e.g., 2, 3, 4, 5, 6, 7, 8, 9, 10 or more) carboxylate groups. For example, the aliphatic group can include one or more polyacrylic acid group. In some cases, the pendant hydrophilic group includes one or more (e.g., 2, 3, 4, 5, 6, 7, 8, 9, 10 or more) sulfonate groups. In some cases, the pendant hydrophilic group includes one or more (e.g., 2, 3, 4, 5, 6, 7, 8, 9, 10 or more) phosphate groups. In some examples, the pendant hydrophilic group includes one or more ammonium groups (e.g., tertiary and/or quaternary ammonium). In other examples, the pendant hydrophilic group includes one or more zwitterionic groups (e.g., a betaine, such as poly(carboxybetaine (pCB) and ammonium phosphonate groups such as a phosphatidylcholine group).

The $R_2$ group can include charged groups that are capable of binding to a counterion to ionically crosslink the polymer and form ionomers. For example, $R_2$ is an aliphatic or aromatic group having pendant amino, carboxylate, sulfonate, phosphate, ammonium, or zwitterionic groups, or combinations thereof.

When a pendant hydrophilic group is present, the pendant hydrophilic group can be at least one polyether group, such as two polyether groups. In other cases, the pendant hydrophilic group is at least one polyester. The pendant hydrophilic group can be a polylactone group (e.g., polyvinylpyrrolidone). Each carbon atom of the pendant hydrophilic group can optionally be substituted with, e.g., an alkyl group having from 1 to 6 carbon atoms. The aliphatic and aromatic groups can be graft polymeric groups, wherein the pendant groups are homopolymeric groups (e.g., polyether groups, polyester groups, polyvinylpyrrolidone groups).

The pendant hydrophilic group can be a polyether group (e.g., a polyethylene oxide (PEO) group, a polyethylene glycol (PEG) group), a polyvinylpyrrolidone group, a polyacrylic acid group, or combinations thereof.

The pendant hydrophilic group can be bonded to the aliphatic group or aromatic group through a linker. The linker can be any bifunctional small molecule (e.g., one having from 1 to 20 carbon atoms) capable of linking the pendant hydrophilic group to the aliphatic or aromatic group. For example, the linker can include a diisocyanate group, as previously described herein, which when linked to the pendant hydrophilic group and to the aliphatic or aromatic group forms a carbamate bond. The linker can be 4,4'-diphenylmethane diisocyanate (MDI), as shown below.

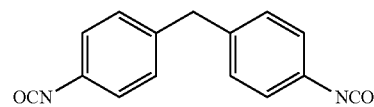

(Formula 3)

The pendant hydrophilic group can be a polyethylene oxide group and the linking group can be MDI, as shown below.

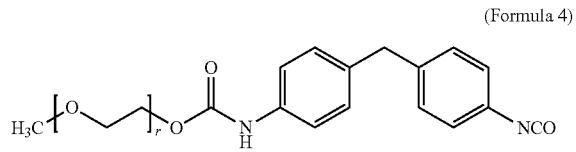

(Formula 4)

The pendant hydrophilic group can be functionalized to enable it to bond to the aliphatic or aromatic group, optionally through the linker. For example, when the pendant hydrophilic group includes an alkene group, which can undergo a Michael addition with a sulfhydryl-containing bifunctional molecule (i.e., a molecule having a second reactive group, such as a hydroxyl group or amino group), resulting in a hydrophilic group that can react with the polymer backbone, optionally through the linker, using the second reactive group. For example, when the pendant hydrophilic group is a polyvinylpyrrolidone group, it can react with the sulfhydryl group on mercaptoethanol to result in hydroxyl-functionalized polyvinylpyrrolidone, as shown below.

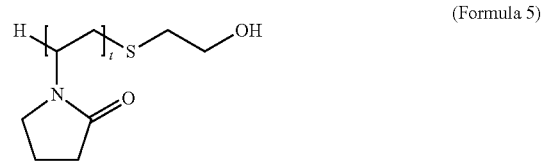

(Formula 5)

At least one $R_2$ group in the polyurethane can include a polytetramethylene oxide group. At least one $R_2$ group of the polyurethane can include an aliphatic polyol group functionalized with a polyethylene oxide group or polyvinylpyrrolidone group, such as the polyols described in E.P. Patent No. 2 462 908, which is hereby incorporated by reference. For example, the $R_2$ group can be derived from the reaction product of a polyol (e.g., pentaerythritol or 2,2,3-trihydroxypropanol) and either MDI-derivatized methoxypolyethylene glycol (to obtain compounds as shown in Formulas 6 or 7) or with MDI-derivatized polyvinylpyrrolidone (to obtain compounds as shown in Formulas 8 or 9) that had been previously been reacted with mercaptoethanol, as shown below.

(Formula 6)

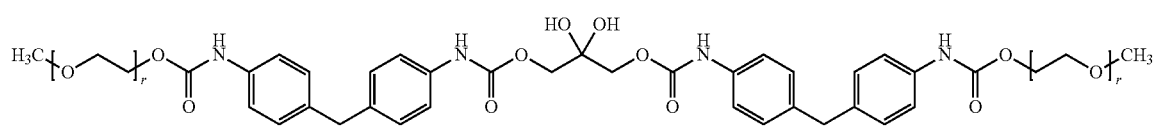

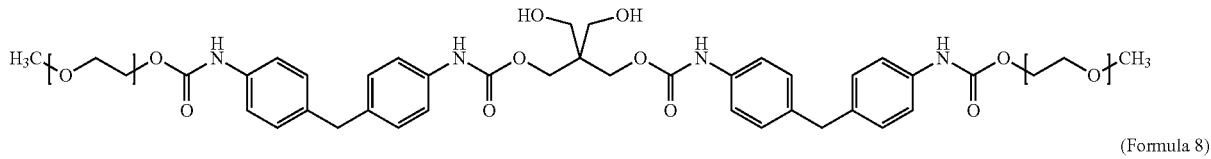

(Formula 7)

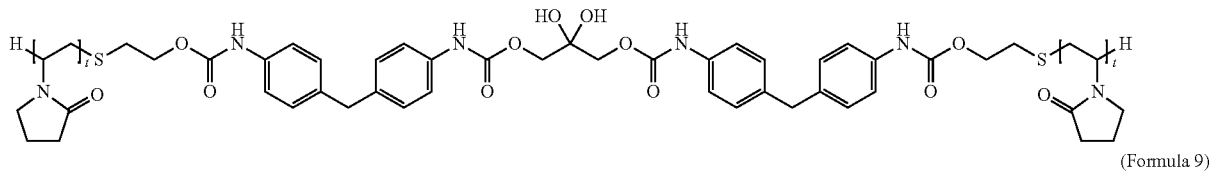

(Formula 8)

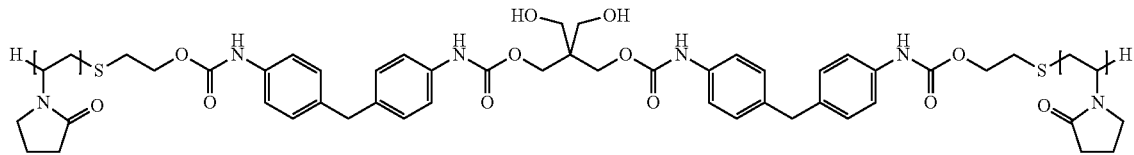

(Formula 9)

At least one $R_2$ of the polyurethane can be a polysiloxane, In these cases, the $R_2$ group can be derived from a silicone monomer of Formula 10, such as a silicone monomer disclosed in U.S. Pat. No. 5,969,076, which is hereby incorporated by reference:

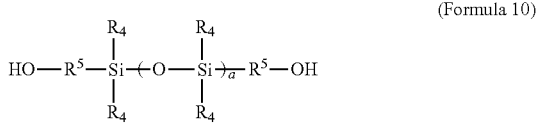

(Formula 10)

wherein: a is 1 to 10 or larger (e.g., 1, 2, 3, 4, 5, 6, 7, 8, 9, or 10); each $R_4$ independently is hydrogen, an alkyl group having from 1 to 18 carbon atoms, an alkenyl group having from 2 to 18 carbon atoms, aryl, or polyether; and each $R_5$ independently is an alkylene group having from 1 to 10 carbon atoms, polyether, or polyurethane.

Each $R_4$ group can independently be a H, an alkyl group having from 1 to 10 carbon atoms, an alkenyl group having from 2 to 10 carbon atoms, an aryl group having from 1 to 6 carbon atoms, polyethylene, polypropylene, or polybutylene group. Each $R_4$ group can independently be selected from the group consisting of methyl, ethyl, n-propyl, iso-propyl, n-butyl, isobutyl, s-butyl, t-butyl, ethenyl, propenyl, phenyl, and polyethylene groups.

Each $R_5$ group can independently include an alkylene group having from 1 to 10 carbon atoms (e.g., a methylene, ethylene, propylene, butylene, pentylene, hexylene, heptylene, octylene, nonylene, or decylene group). Each $R_5$ group can be a polyether group (e.g., a polyethylene, polypropylene, or polybutylene group). Each $R_5$ group can be a polyurethane group.

Optionally, the polyurethane can include an at least partially crosslinked polymeric network that includes polymer chains that are derivatives of polyurethane. The level of crosslinking can be such that the polyurethane retains thermoplastic properties (i.e., the crosslinked thermoplastic polyurethane can be melted and re-solidified under the processing conditions described herein). The crosslinked polyurethane can be a thermoset polymer. This crosslinked polymeric network can be produced by polymerizing one or more isocyanates with one or more polyamino compounds, polysulfhydryl compounds, or combinations thereof, as shown in Formulas 11 and 12, below:

(Formula 11)

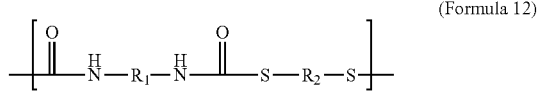

(Formula 12)

wherein the variables are as described above. Additionally, the isocyanates can also be chain extended with one or more polyamino or polythiol chain extenders to bridge two or more isocyanates, such as previously described for the polyurethanes of Formula 2.

The polyurethane chain can be physically crosslinked to another polyurethane chain through e.g., nonpolar or polar interactions between the urethane or carbamate groups of the polymers (the hard segments). The $R_1$ group in Formula 1, and the $R_1$ and $R_3$ groups in Formula 2, form the portion of the polymer often referred to as the "hard segment", and the $R_2$ group forms the portion of the polymer often referred to as the "soft segment". The soft segment is covalently bonded to the hard segment. The polyurethane having physically crosslinked hard and soft segments can be a hydrophilic polyurethane (i.e., a polyurethane, including a thermoplastic polyurethane, including hydrophilic groups as disclosed herein).

The polyurethane can be a thermoplastic polyurethane composed of MDI, PTMO, and 1,4-butylene glycol, as described in U.S. Pat. No. 4,523,005. Commercially available polyurethanes suitable for the present use include, but are not limited to those under the tradename "SANCURE" (e.g., the "SANCURE" series of polymer such as "SAN-CURE" 20025F) or "TECOPHILIC" (e.g., TG-500, TG-2000, SP-80A-150, SP-93A-100, SP-60D-60) (Lubrizol, Countryside, Ill., USA), "PELLETHANE" 2355-85ATP and 2355-95AE (Dow Chemical Company of Midland, Mich., USA.), "ESTANE" (e.g., ALR G 500, or 58213; Lubrizol, Countryside, Ill., USA).

One or more of the polyurethanes (e.g., those used in the primer as the coating (e.g., water-dispersible polyurethane)) can be produced by polymerizing one or more isocyanates with one or more polyols to produce copolymer chains having carbamate linkages (—N(C=O)O—) and one or more water-dispersible enhancing moieties, where the polymer chain includes one or more water-dispersible enhancing moieties (e.g., a monomer in polymer chain). The water-dispersible polyurethane can also be referred to as "a water-borne polyurethane polymer dispersion." The water-dispersible enhancing moiety can be added to the chain of Formula 1 or 2 (e.g., within the chain and/or onto the chain as a side chain). Inclusion of the water-dispersible enhancing moiety enables the formation of a water-borne polyurethane dispersion. The term "water-borne" herein means the continuous phase of the dispersion or formulation of about 50 weight percent to 100 weight percent water, about 60 weight percent to 100 weight percent water, about 70 weight percent to 100 weight percent water, or about 100 weight percent water. The term "water-borne dispersion" refers to a dispersion of a component (e.g., polymer, cross-linker, and the like) in water without co-solvents. The co-solvent can be used in the water-borne dispersion and the co-solvent can be an organic solvent. Additional detail regarding the polymers, polyurethanes, isocyantes and the polyols are provided below.

The polyurethane (e.g., a water-borne polyurethane polymer dispersion) can include one or more water-dispersible enhancing moieties. The water-dispersible enhancing moiety can have at least one hydrophilic (e.g., poly(ethylene oxide)), ionic or potentially ionic group to assist dispersion of the polyurethane, thereby enhancing the stability of the dispersions. A water-dispersible polyurethane can be formed by incorporating a moiety bearing at least one hydrophilic group or a group that can be made hydrophilic (e.g., by chemical modifications such as neutralization) into the polymer chain. For example, these compounds can be nonionic, anionic, cationic or zwitterionic or the combination thereof. In one example, anionic groups such as carboxylic acid groups can be incorporated into the chain in an inactive form and subsequently activated by a salt-forming compound, such as a tertiary amine. Other water-dispersible enhancing moieties can also be reacted into the backbone through urethane linkages or urea linkages, including lateral or terminal hydrophilic ethylene oxide or ureido units.

The water-dispersible enhancing moiety can be a one that includes carboxyl groups. Water-dispersible enhancing moiety that include a carboxyl group can be formed from hydroxy-carboxylic acids having the general formula $(HO)_x Q(COOH)_y$, where Q can be a straight or branched bivalent hydrocarbon radical containing 1 to 12 carbon atoms, and x and y can each independently be 1 to 3. Illustrative examples include dimethylolpropanoic acid (DMPA), dimethylol butanoic acid (DMBA), citric acid, tartaric acid, glycolic acid, lactic acid, malic acid, dihydroxymalic acid, dihydroxytartaric acid, and the like, and mixtures thereof.

The water-dispersible enhancing moiety can include reactive polymeric polyol components that contain pendant anionic groups that can be polymerized into the backbone to impart water dispersible characteristics to the polyurethane. Anionic functional polymeric polyols can include anionic polyester polyols, anionic polyether polyols, and anionic polycarbonate polyols, where additional detail is provided in U.S. Pat. No. 5,334,690.

The water-dispersible enhancing moiety can include a side chain hydrophilic monomer. For example, the water-dispersible enhancing moiety including the side chain hydrophilic monomer can include alkylene oxide polymers and copolymers in which the alkylene oxide groups have from 2-10 carbon atoms as shown in U.S. Pat. No. 6,897,281. Additional types of water-dispersible enhancing moieties can include thioglycolic acid, 2,6-dihydroxybenzoic acid, sulfoisophthalic acid, polyethylene glycol, and the like, and mixtures thereof. Additional details regarding water-dispersible enhancing moieties can be found in U.S. Pat. No. 7,476,705.

Polyamides

The polymer can comprise a polyamide, such as a thermoplastic polyamide, or a thermoset polyamide. The polyamide can be an elastomeric polyamide, including an elastomeric thermoplastic polyamide or an elastomeric thermoset polyamide. The polyamide can be a polyamide homopolymer having repeating polyamide segments of the same chemical structure. Alternatively, the polyamide can comprise a number of polyamide segments having different polyamide chemical structures (e.g., polyamide 6 segments, polyamide 11 segments, polyamide 12 segments, polyamide 66 segments, etc.). The polyamide segments having different chemical structure can be arranged randomly, or can be arranged as repeating blocks.

The polyamide can be a co-polyamide (i.e., a co-polymer including polyamide segments and non-polyamide segments). The polyamide segments of the co-polyamide can comprise or consist of polyamide 6 segments, polyamide 11 segments, polyamide 12 segments, polyamide 66 segments, or any combination thereof. The polyamide segments of the co-polyamide can be arranged randomly, or can be arranged as repeating segments. The polyamide segments can comprise or consist of polyamide 6 segments, or polyamide 12 segments, or both polyamide 6 segment and polyamide 12 segments. In the example where the polyamide segments of the co-polyamide include of polyamide 6 segments and polyamide 12 segments, the segments can be arranged randomly. The non-polyamide segments of the co-polyamide can comprise or consist of polyether segments, polyester segments, or both polyether segments and polyester segments. The co-polyamide can be a block co-polyamide, or can be a random co-polyamide. The copolyamide can be formed from the polycondensation of a polyamide oligomer or prepolymer with a second oligomer prepolymer to form a copolyamide (i.e., a co-polymer including polyamide segments. Optionally, the second prepolymer can be a hydrophilic prepolymer.

The polyamide can be a polyamide-containing block co-polymer. For example, the block co-polymer can have repeating hard segments, and repeating soft segments. The hard segments can comprise polyamide segments, and the soft segments can comprise non-polyamide segments. The polyamide-containing block co-polymer can be an elastomeric co-polyamide comprising or consisting of polyamide-containing block co-polymers having repeating hard segments and repeating soft segments. In block co-polymers, including block co-polymers having repeating hard segments and soft segments, physical crosslinks can be present within the segments or between the segments or both within and between the segments.

The polyamide itself, or the polyamide segment of the polyamide-containing block co-polymer can be derived from the condensation of polyamide prepolymers, such as lactams, amino acids, and/or diamino compounds with dicarboxylic acids, or activated forms thereof. The resulting polyamide segments include amide linkages (—(CO)NH—). The term "amino acid" refers to a molecule having at least one amino group and at least one carboxyl group. Each polyamide segment of the polyamide can be the same or different.

The polyamide or the polyamide segment of the polyamide-containing block co-polymer can be derived from the polycondensation of lactams and/or amino acids, and can include an amide segment having a structure shown in Formula 13, below, wherein $R_6$ group represents the portion of the polyamide derived from the lactam or amino acid.

(Formula 13)

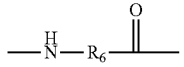

The $R_6$ group can be derived from a lactam. The $R_6$ group can be derived from a lactam group having from 3 to 20 carbon atoms, or a lactam group having from 4 to 15 carbon atoms, or a lactam group having from 6 to 12 carbon atoms. The $R_6$ group can be derived from caprolactam or laurolactam. The $R_6$ group can be derived from one or more amino acids. The $R_6$ group can be derived from an amino acid group having from 4 to 25 carbon atoms, or an amino acid group having from 5 to 20 carbon atoms, or an amino acid group having from 8 to 15 carbon atoms. The $R_6$ group can be derived from 12-aminolauric acid or 11-aminoundecanoic acid.

Optionally, in order to increase the relative degree of hydrophilicity of the polyamide-containing block co-polymer, Formula 13 can include a polyamide-polyether block copolymer segment, as shown below:

(Formula 14)

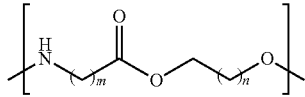

wherein m is 3-20, and n is 1-8. Optionally, m is 4-15, or 6-12 (e.g., 6, 7, 8, 9, 10, 11, or 12), and n is 1, 2, or 3. For example, m can be 11 or 12, and n can be 1 or 3. The polyamide or the polyamide segment of the polyamide-containing block co-polymer can be derived from the condensation of diamino compounds with dicarboxylic acids, or activated forms thereof, and can include an amide segment having a structure shown in Formula 15, below, wherein the $R_7$ group represents the portion of the polyamide derived from the diamino compound, and the $R_8$ group represents the portion derived from the dicarboxylic acid compound:

(Formula 15)

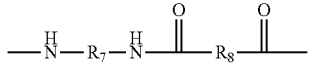

The $R_7$ group can be derived from a diamino compound that includes an aliphatic group having from 4 to 15 carbon atoms, or from 5 to 10 carbon atoms, or from 6 to 9 carbon atoms. The diamino compound can include an aromatic group, such as phenyl, naphthyl, xylyl, and tolyl. Suitable diamino compounds from which the $R_7$ group can be derived include, but are not limited to, hexamethylene diamine (HMD), tetramethylene diamine, trimethyl hexamethylene diamine (TMD), m-xylylene diamine (MXD), and 1,5-pentamine diamine. The $R_8$ group can be derived from a dicarboxylic acid or activated form thereof, including an aliphatic group having from 4 to 15 carbon atoms, or from 5 to 12 carbon atoms, or from 6 to 10 carbon atoms. The dicarboxylic acid or activated form thereof from which $R_8$ can be derived includes an aromatic group, such as phenyl, naphthyl, xylyl, and tolyl groups. Suitable carboxylic acids or activated forms thereof from which $R_8$ can be derived include adipic acid, sebacic acid, terephthalic acid, and isophthalic acid. The polyamide chain can be substantially free of aromatic groups.

Each polyamide segment of the polyamide (including the polyamide-containing block co-polymer) can be independently derived from a polyamide prepolymer selected from the group consisting of 12-aminolauric acid, caprolactam, hexamethylene diamine and adipic acid.

The polyamide can comprise or consist essentially of a poly(ether-block-amide). The poly(ether-block-amide) can be formed from the polycondensation of a carboxylic acid terminated polyamide prepolymer and a hydroxyl terminated polyether prepolymer to form a poly(ether-block-amide), as shown in Formula 16:

(Formula 16)

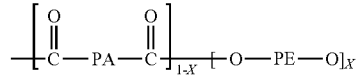

The poly(ether block amide) polymer can be prepared by polycondensation of polyamide blocks containing reactive ends with polyether blocks containing reactive ends. Examples include: 1) polyamide blocks containing diamine chain ends with polyoxyalkylene blocks containing carboxylic chain ends; 2) polyamide blocks containing dicarboxylic chain ends with polyoxyalkylene blocks containing diamine chain ends obtained by cyanoethylation and hydrogenation of aliphatic dihydroxylated alpha-omega polyoxyalkylenes known as polyether diols; 3) polyamide blocks containing dicarboxylic chain ends with polyether diols, the products obtained in this particular case being polyetheresteramides. The polyamide block of the poly(ether-block-amide) can be derived from lactams, amino acids, and/or diamino compounds with dicarboxylic acids as previously described. The polyether block can be derived from one or more polyethers selected from the group consisting of polyethylene oxide (PEO), polypropylene oxide (PPO), polytetrahydrofuran (PTHF), polytetramethylene oxide (PTMO), and combinations thereof.

The poly(ether block amide) polymers can include those comprising polyamide blocks comprising dicarboxylic chain ends derived from the condensation of α, ω-aminocarboxylic acids, of lactams or of dicarboxylic acids and diamines in the presence of a chain-limiting dicarboxylic acid. In poly(ether block amide) polymers of this type, a α, ω-aminocarboxylic acid such as aminoundecanoic acid can be used; a lactam such as caprolactam or lauryllactam can be used; a dicarboxylic acid such as adipic acid, decanedioic acid or dodecanedioic acid can be used; and a diamine such as hexamethylenediamine can be used; or various combinations of any of the foregoing. The copolymer can comprise polyamide blocks comprising polyamide 12 or of polyamide 6.

The poly(ether block amide) polymers can include those comprising polyamide blocks derived from the condensation of one or more α, ω-aminocarboxylic acids and/or of one or more lactams containing from 6 to 12 carbon atoms in the presence of a dicarboxylic acid containing from 4 to 12 carbon atoms, and are of low mass, i.e., they have a number-average molecular weight of from 400 to 1000. In poly(ether block amide) polymers of this type, an α, ω-aminocarboxylic acid such as aminoundecanoic acid or aminododecanoic acid can be used; a dicarboxylic acid such as adipic acid, sebacic acid, isophthalic acid, butanedioic acid, 1,4-cyclohexyldicarboxylic acid, terephthalic acid, the sodium or lithium salt of sulphoisophthalic acid, dimerized fatty acids (these dimerized fatty acids have a dimer content of at least 98 weight percent and are preferably hydrogenated) and dodecanedioic acid $HOOC-(CH_2)_{10}-COOH$ can be used; and a lactam such as caprolactam and lauryllactam can be used; or various combinations of any of the foregoing. The copolymer can comprise polyamide blocks obtained by condensation of lauryllactam in the presence of adipic acid or dodecanedioic acid and with a number average molecular weight of at least 750 have a melting temperature of from about 127 to about 130 degrees C. The various constituents of the polyamide block and their proportion can be chosen in order to obtain a melting point of less than 150 degrees C., or from about 90 degrees C. to about 135 degrees C.

The poly(ether block amide) polymers can include those comprising polyamide blocks derived from the condensation of at least one α, ω-aminocarboxylic acid (or a lactam), at least one diamine and at least one dicarboxylic acid. In copolymers of this type, a α,ω-aminocarboxylic acid, the lactam and the dicarboxylic acid can be chosen from those described herein above and the diamine that can be used can include an aliphatic diamine containing from 6 to 12 atoms and can be acyclic and/or saturated cyclic such as, but not limited to, hexamethylenediamine, piperazine, 1-aminoethylpiperazine, bisaminopropylpiperazine, tetramethylenediamine, octamethylene-diamine, decamethylenediamine, dodecamethylenediamine, 1,5-diaminohexane, 2,2,4-trimethyl-1,6-diaminohexane, diamine polyols, isophoronediamine (IPD), methylpentamethylenediamine (MPDM), bis(aminocyclohexyl)methane (BACM) and bis(3-methyl-4-aminocyclohexyl)methane (BMACM).

The polyamide can be a thermoplastic polyamide and the constituents of the polyamide block and their proportion can be chosen in order to obtain a melting temperature of less than 150 degrees C., such as a melting point of from about 90 degrees C. to about 135 degrees C. The various constituents of the thermoplastic polyamide block and their proportion can be chosen in order to obtain a melting point of less than 150 degrees C., such as from about and 90 degrees C. to about 135 degrees C.

The number average molar mass of the polyamide blocks can be from about 300 grams per mole to about 15,000 grams per mole, from about 500 grams per mole to about 10,000 grams per mole, from about 500 grams per mole to about 6,000 grams per mole, from about 500 grams per mole to about 5,000 grams per mole, or from about 600 grams per mole to about 5,000 grams per mole. The number average molecular weight of the polyether block can range from about 100 to about 6,000, from about 400 to about 3000, or from about 200 to about 3,000. The polyether (PE) content (x) of the poly(ether block amide) polymer can be from about 0.05 to about 0.8 (i.e., from about 5 mole percent to about 80 mole percent). The polyether blocks can be present in the polyamide in an amount of from about 10 weight percent to about 50 weight percent, from about 20 weight percent to about 40 weight percent, or from about 30 weight percent to about 40 weight percent. The polyamide blocks can be present in the polyamide in an amount of from about 50 weight percent to about 90 weight percent, from about 60 weight percent to about 80 weight percent, or from about 70 weight percent to about 90 weight percent.

The polyether blocks can contain units other than ethylene oxide units, such as, for example, propylene oxide or polytetrahydrofuran (which leads to polytetramethylene glycol sequences). It is also possible to use simultaneously PEG blocks, i.e., those consisting of ethylene oxide units, polypropylene glycol (PPG) blocks, i.e. those consisting of propylene oxide units, and poly(tetramethylene ether)glycol (PTMG) blocks, i.e. those consisting of tetramethylene glycol units, also known as polytetrahydrofuran. PPG or PTMG blocks are advantageously used. The amount of polyether blocks in these copolymers containing polyamide and polyether blocks can be from about 10 weight percent to about 50 weight percent of the copolymer, or from about 35 weight percent to about 50 weight percent.

The copolymers containing polyamide blocks and polyether blocks can be prepared by any means for attaching the polyamide blocks and the polyether blocks. In practice, two processes are essentially used, one being a 2-step process and the other a one-step process.

In the two-step process, the polyamide blocks having dicarboxylic chain ends are prepared first, and then, in a second step, these polyamide blocks are linked to the polyether blocks. The polyamide blocks having dicarboxylic chain ends are derived from the condensation of polyamide precursors in the presence of a chain-stopper dicarboxylic acid. If the polyamide precursors are only lactams or α,ω-aminocarboxylic acids, a dicarboxylic acid is added. If the precursors already comprise a dicarboxylic acid, this is used in excess with respect to the stoichiometry of the diamines. The reaction usually takes place from about 180 to about 300 degrees C., such as from about 200 degrees to about 290 degrees C., and the pressure in the reactor can be set from about 5 to about 30 bar and maintained for approximately 2 to 3 hours. The pressure in the reactor is slowly reduced to atmospheric pressure and then the excess water is distilled off, for example for one or two hours.

Once the polyamide having carboxylic acid end groups has been prepared, the polyether, the polyol and a catalyst are then added. The total amount of polyether can be divided and added in one or more portions, as can the catalyst. The polyether is added first and the reaction of the OH end groups of the polyether and of the polyol with the COOH end groups of the polyamide starts, with the formation of ester linkages and the elimination of water. Water is removed as much as possible from the reaction mixture by distillation and then the catalyst is introduced in order to complete the linking of the polyamide blocks to the polyether blocks. This second step takes place with stirring, preferably under a vacuum of at least 50 millibar (5000 Pascals) at a temperature such that the reactants and the copolymers obtained are in the molten state. By way of example, this temperature can be from about 100 to about 400 degrees C., such as from about 200 to about 250 degrees C. The reaction is monitored by measuring the torque exerted by the polymer melt on the stirrer or by measuring the electric power consumed by the stirrer. The end of the reaction is determined by the value of the torque or of the target power. The catalyst is defined as being any product which promotes the linking of the polyamide blocks to the polyether blocks by esterification. The catalyst can be a derivative of a metal (M) chosen from the group formed by titanium, zirconium and hafnium. The derivative can be prepared from a tetraalkoxides consistent with the general formula $M(OR)_4$, in which M represents titanium, zirconium or hafnium and R, which can be identical or different, represents linear or branched alkyl radicals having from 1 to 24 carbon atoms.

The catalyst can comprise a salt of the metal (M), particularly the salt of (M) and of an organic acid and the complex salts of the oxide of (M) and/or the hydroxide of (M) and an organic acid. The organic acid can be formic acid, acetic acid, propionic acid, butyric acid, valeric acid, caproic acid, caprylic acid, lauric acid, myristic acid, palmitic acid, stearic acid, oleic acid, linoleic acid, linolenic acid, cyclohexanecarboxylic acid, phenylacetic acid, benzoic acid, salicylic acid, oxalic acid, malonic acid, succinic acid, glutaric acid, adipic acid, maleic acid, fumaric acid, phthalic acid or crotonic acid. The organic acid can be an acetic acid or a propionic acid. M can be zirconium and such salts are called zirconyl salts, e.g., the commercially available product sold under the name zirconyl acetate.

The weight proportion of catalyst can vary from about 0.01 to about 5 percent of the weight of the mixture of the dicarboxylic polyamide with the polyetherdiol and the polyol. The weight proportion of catalyst can vary from about 0.05 to about 2 percent of the weight of the mixture of the dicarboxylic polyamide with the polyetherdiol and the polyol.

In the one-step process, the polyamide precursors, the chain stopper and the polyether are blended together; what is then obtained is a polymer having essentially polyether blocks and polyamide blocks of highly variable length, but also the various reactants that have reacted randomly, which are distributed randomly along the polymer chain. They are the same reactants and the same catalyst as in the two-step process described above. If the polyamide precursors are only lactams, it is advantageous to add a little water. The copolymer has essentially the same polyether blocks and the same polyamide blocks, but also a small portion of the various reactants that have reacted randomly, which are distributed randomly along the polymer chain. As in the first step of the two-step process described above, the reactor is closed and heated, with stirring. The pressure established is from about 5 to about 30 bar. When the pressure no longer changes, the reactor is put under reduced pressure while still maintaining vigorous stirring of the molten reactants. The reaction is monitored as previously in the case of the two-step process.

The proper ratio of polyamide to polyether blocks can be found in a single poly(ether block amide), or a blend of two or more different composition poly(ether block amide)s can be used with the proper average composition. It can be useful to blend a block copolymer having a high level of polyamide groups with a block copolymer having a higher level of polyether blocks, to produce a blend having an average level of polyether blocks of about 20 to about 40 weight percent of the total blend of poly(amid-block-ether) copolymers, or about 30 to about 35 weight percent. The copolymer can comprise a blend of two different poly(ether-block-amide)s comprising at least one block copolymer having a level of polyether blocks below 35 weight percent, and a second poly(ether-block-amide) having at least 45 weight percent of polyether blocks.

Exemplary commercially available copolymers include, but are not limited to, those available under the tradenames of "VESTAMID" (Evonik Industries, Essen, Germany); "PLATAMID" (Arkema, Colombes, France), e.g., product code H2694; "PEBAX" (Arkema), e.g., product code "PEBAX MH1657" and "PEBAX MV1074"; "PEBAX RNEW" (Arkema); "GRILAMID" (EMS-Chemie AG, Domat-Ems, Switzerland), or also to other similar materials produced by various other suppliers.

The polyamide can be physically crosslinked through, e.g., nonpolar or polar interactions between the polyamide groups of the polymers. In examples where the polyamide is a copolyamide, the copolyamide can be physically crosslinked through interactions between the polyamide groups, and optionally by interactions between the copolymer groups. When the co-polyamide is physically crosslinked through interactions between the polyamide groups, the polyamide segments can form the portion of the polymer referred to as the hard segment, and copolymer segments can form the portion of the polymer referred to as the soft segment. For example, when the copolyamide is a poly (ether-block-amide), the polyamide segments form the hard segments of the polymer, and polyether segments form the soft segments of the polymer. Therefore, in some examples, the polymer can include a physically crosslinked polymeric network having one or more polymer chains with amide linkages.

The polyamide segment of the co-polyamide can include polyamide-11 or polyamide-12 and the polyether segment can be a segment selected from the group consisting of polyethylene oxide, polypropylene oxide, and polytetramethylene oxide segments, and combinations thereof.

The polyamide can be partially or fully covalently crosslinked, as previously described herein. In some cases, the degree of crosslinking present in the polyamide is such that, when it is thermally processed, e.g., in the form of a yarn or fiber to form the articles of the present disclosure, the partially covalently crosslinked thermoplastic polyamide retains sufficient thermoplastic character that the partially covalently crosslinked thermoplastic polyamide is melted during the processing and re-solidifies. In other cases, the crosslinked polyamide is a thermoset polymer.

Polyesters

The polymers can comprise a polyester. The polyester can comprise a thermoplastic polyester, or a thermoset polyester. Additionally, the polyester can be an elastomeric polyester, including a thermoplastic polyester or a thermoset elastomeric polyester. The polyester can be formed by reaction of one or more carboxylic acids, or its ester-forming derivatives, with one or more bivalent or multivalent aliphatic, alicyclic, aromatic or aralipatic alcohols or a bisphenol. The polyester can be a polyester homopolymer having repeating polyester segments of the same chemical structure. Alternatively, the polyester can comprise a number of polyester segments having different polyester chemical structures (e.g., polyglycolic acid segments, polylactic acid segments, polycaprolactone segments, polyhydroxyalkanoate segments, polyhydroxybutyrate segments, etc.). The polyester segments having different chemical structure can be arranged randomly, or can be arranged as repeating blocks.

Exemplary carboxylic acids that can be used to prepare a polyester include, but are not limited to, adipic acid, pimelic acid, suberic acid, azelaic acid, sebacic acid, nonane dicarboxylic acid, decane dicarboxylic acid, undecane dicarboxylic acid, terephthalic acid, isophthalic acid, alkyl-substituted or halogenated terephthalic acid, alkyl-substituted or halogenated isophthalic acid, nitro-terephthalic acid, 4,4'-diphenyl ether dicarboxylic acid, 4,4'-diphenyl thioether dicarboxylic acid, 4,4'-diphenyl sulfone-dicarboxylic acid, 4,4'-diphenyl alkylenedicarboxylic acid, naphthalene-2,6-dicarboxylic acid, cyclohexane-1,4-dicarboxylic acid and cyclohexane-1,3-dicarboxylic acid. Exemplary diols or phenols suitable for the preparation of the polyester include, but are not limited to, ethylene glycol, diethylene glycol, 1,3- propanediol, 1,4-butanediol, 1,6-hexanediol, 1,8-octanediol, 1,10-decanediol, 1,2-propanediol, 2,2-dimethyl-1,3-propanediol, 2,2,4-trimethylhexanediol, p-xylenediol, 1,4-cyclohexanediol, 1,4-cyclohexane dimethanol, and bis-phenol A.

The polyester can be a polybutylene terephthalate (PBT), a polytrimethylene terephthalate, a polyhexamethylene terephthalate, a poly-1,4-dimethylcyclohexane terephthalate, a polyethylene terephthalate (PET), a polyethylene isophthalate (PEI), a polyarylate (PAR), a polybutylene naphthalate (PBN), a liquid crystal polyester, or a blend or mixture of two or more of the foregoing.

The polyester can be a co-polyester (i.e., a co-polymer including polyester segments and non-polyester segments). The co-polyester can be an aliphatic co-polyester (i.e., a co-polyester in which both the polyester segments and the non-polyester segments are aliphatic). Alternatively, the co-polyester can include aromatic segments. The polyester segments of the co-polyester can comprise or consist essentially of polyglycolic acid segments, polylactic acid segments, polycaprolactone segments, polyhydroxyalkanoate segments, polyhydroxybutyrate segments, or any combination thereof. The polyester segments of the co-polyester can be arranged randomly, or can be arranged as repeating blocks.

For example, the polyester can be a block co-polyester having repeating blocks of polymeric units of the same chemical structure which are relatively harder (hard segments), and repeating blocks of the same chemical structure which are relatively softer (soft segments). In block co-polyesters, including block co-polyesters having repeating hard segments and soft segments, physical crosslinks can be present within the blocks or between the blocks or both within and between the blocks. The polymer can comprise or consist essentially of an elastomeric co-polyester having repeating blocks of hard segments and repeating blocks of soft segments.

The non-polyester segments of the co-polyester can comprise or consist essentially of polyether segments, polyamide segments, or both polyether segments and polyamide segments. The co-polyester can be a block co-polyester, or can be a random co-polyester. The co-polyester can be formed from the polycondensation of a polyester oligomer or prepolymer with a second oligomer prepolymer to form a block copolyester. Optionally, the second prepolymer can be a hydrophilic prepolymer. For example, the co-polyester can be formed from the polycondensation of terephthalic acid or naphthalene dicarboxylic acid with ethylene glycol, 1,4-butanediol, or 1,3-propanediol. Examples of co-polyesters include polyethylene adipate, polybutylene succinate, poly (3-hydroxybutyrate-co-3-hydroxyvalerate), polyethylene terephthalate, polybutylene terephthalate, polytrimethylene terephthalate, polyethylene napthalate, and combinations thereof. The co-polyamide can comprise or consist of polyethylene terephthalate.

The polyester can be a block copolymer comprising segments of one or more of polybutylene terephthalate (PBT), a polytrimethylene terephthalate, a polyhexamethylene terephthalate, a poly-1,4-dimethylcyclohexane terephthalate, a polyethylene terephthalate (PET), a polyethylene isophthalate (PEI), a polyarylate (PAR), a polybutylene naphthalate (PBN), and a liquid crystal polyester. For example, a suitable polyester that is a block copolymer can be a PET/PEI copolymer, a polybutylene terephthalate/ tetraethylene glycol copolymer, a polyoxyalkylenediimide diacid/polybutylene terephthalate copolymer, or a blend or mixture of any of the foregoing.

The polyester can be a biodegradable resin, for example, a copolymerized polyester in which poly($\alpha$-hydroxy acid) such as polyglycolic acid or polylactic acid is contained as principal repeating units.

The disclosed polyesters can be prepared by a variety of polycondensation methods known to the skilled artisan, such as a solvent polymerization or a melt polymerization process.

Polyolefins

The polymers can comprise or consist essentially of a polyolefin. The polyolefin can be a thermoplastic polyolefin or a thermoset polyolefin. Additionally, the polyolefin can be an elastomeric polyolefin, including a thermoplastic elastomeric polyolefin or a thermoset elastomeric polyolefin. Exemplary polyolefins can include polyethylene, polypropylene, and olefin elastomers (e.g., metallocene-catalyzed block copolymers of ethylene and $\alpha$-olefins having 4 to about 8 carbon atoms). The polyolefin can be a polymer comprising a polyethylene, an ethylene-$\alpha$-olefin copolymer, an ethylene-propylene rubber (EPDM), a polybutene, a polyisobutylene, a poly-4-methylpent-1-ene, a polyisoprene, a polybutadiene, a ethylene-methacrylic acid copolymer, and an olefin elastomer such as a dynamically cross-linked polymer obtained from polypropylene (PP) and an ethylene-propylene rubber (EPDM), and blends or mixtures of the foregoing. Further exemplary polyolefins include polymers of cycloolefins such as cyclopentene or norbornene.

It is to be understood that polyethylene, which optionally can be crosslinked, is inclusive a variety of polyethylenes, including low density polyethylene (LDPE), linear low density polyethylene (LLDPE), (VLDPE) and (ULDPE), medium density polyethylene (MDPE), high density polyethylene (HDPE), high density and high molecular weight polyethylene (HDPE-HMW), high density and ultrahigh molecular weight polyethylene (HDPE-UHMVV), and blends or mixtures of any the foregoing polyethylenes. A polyethylene can also be a polyethylene copolymer derived from monomers of monolefins and diolefins copolymerized with a vinyl, acrylic acid, methacrylic acid, ethyl acrylate, vinyl alcohol, and/or vinyl acetate. Polyolefin copolymers comprising vinyl acetate-derived units can be a high vinyl acetate content copolymer, e.g., greater than about 50 weight percent vinyl acetate-derived composition.

The polyolefin can be formed through free radical, cationic, and/or anionic polymerization by methods well known to those skilled in the art (e.g., using a peroxide initiator, heat, and/or light). The disclosed polyolefin can be prepared by radical polymerization under high pressure and at elevated temperature. Alternatively, the polyolefin can be prepared by catalytic polymerization using a catalyst that normally contains one or more metals from group IVb, Vb, VIb or VIII metals. The catalyst usually has one or more than one ligand, typically oxides, halides, alcoholates, esters, ethers, amines, alkyls, alkenyls and/or aryls that can be either p- or s-coordinated complexed with the group IVb, Vb, VIb or VIII metal. The metal complexes can be in the free form or fixed on substrates, typically on activated magnesium chloride, titanium(III) chloride, alumina or silicon oxide. The metal catalysts can be soluble or insoluble in the polymerization medium. The catalysts can be used by themselves in the polymerization or further activators can be used, typically a group Ia, IIa and/or IIIa metal alkyls, metal hydrides, metal alkyl halides, metal alkyl oxides or metal alkyloxanes. The activators can be modified conveniently with further ester, ether, amine or silyl ether groups.

Suitable polyolefins can be prepared by polymerization of monomers of monolefins and diolefins as described herein.

Exemplary monomers that can be used to prepare the polyolefin include, but are not limited to, ethylene, propylene, 1-butene, 1-pentene, 1-hexene, 2-methyl-1-propene, 3-methyl-1-pentene, 4-methyl-1-pentene, 5-methyl-1-hexene and mixtures thereof.

Suitable ethylene-α-olefin copolymers can be obtained by copolymerization of ethylene with an α-olefin such as propylene, butene-1, hexene-1, octene-1,4-methyl-1-pentene or the like having carbon numbers of 3 to 12.

Suitable dynamically cross-linked polymers can be obtained by cross-linking a rubber component as a soft segment while at the same time physically dispersing a hard segment such as PP and a soft segment such as EPDM by using a kneading machine such as a Banbury mixer and a biaxial extruder.

The polyolefin can be a mixture of polyolefins, such as a mixture of two or more polyolefins disclosed herein above. For example, a suitable mixture of polyolefins can be a mixture of polypropylene with polyisobutylene, polypropylene with polyethylene (for example PP/HDPE, PP/LDPE) or mixtures of different types of polyethylene (for example LDPE/HDPE).

The polyolefin can be a copolymer of suitable monolefin monomers or a copolymer of a suitable monolefin monomer and a vinyl monomer. Exemplary polyolefin copolymers include ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

The polyolefin can be a polypropylene homopolymer, a polypropylene copolymers, a polypropylene random copolymer, a polypropylene block copolymer, a polyethylene homopolymer, a polyethylene random copolymer, a polyethylene block copolymer, a low density polyethylene (LDPE), a linear low density polyethylene (LLDPE), a medium density polyethylene, a high density polyethylene (HDPE), or blends or mixtures of one or more of the preceding polymers.

The polyolefin can be a polypropylene. The term "polypropylene," as used herein, is intended to encompass any polymeric composition comprising propylene monomers, either alone or in mixture or copolymer with other randomly selected and oriented polyolefins, dienes, or other monomers (such as ethylene, butylene, and the like). Such a term also encompasses any different configuration and arrangement of the constituent monomers (such as atactic, syndiotactic, isotactic, and the like). Thus, the term as applied to fibers is intended to encompass actual long strands, tapes, threads, and the like, of drawn polymer. The polypropylene can be of any standard melt flow (by testing); however, standard fiber grade polypropylene resins possess ranges of Melt Flow Indices between about 1 and 1000.

The polyolefin can be a polyethylene. The term "polyethylene," as used herein, is intended to encompass any polymeric composition comprising ethylene monomers, either alone or in mixture or copolymer with other randomly selected and oriented polyolefins, dienes, or other monomers (such as propylene, butylene, and the like). Such a term also encompasses any different configuration and arrangement of the constituent monomers (such as atactic, syndiotactic, isotactic, and the like). Thus, the term as applied to fibers is intended to encompass actual long strands, tapes, threads, and the like, of drawn polymer. The polyethylene can be of any standard melt flow (by testing); however, standard fiber grade polyethylene resins possess ranges of Melt Flow Indices between about 1 and 1000.

The thermoplastic and/or thermosetting material can further comprise one or more processing aids. The processing aid can be a non-polymeric material. These processing aids can be independently selected from the group including, but not limited to, curing agents, initiators, plasticizers, mold release agents, lubricants, antioxidants, flame retardants, dyes, pigments, reinforcing and non-reinforcing fillers, fiber reinforcements, and light stabilizers Now turning to the first thermoplastic material that the optical element can be disposed onto (e.g., affixed or adhered to), additional details regarding the composition are provided. In an aspect, the thermoplastic material that the optical element disposed onto (e.g., first yarn) can have a softening or melting point of about 80° C. to about 140° C. In another aspect, the thermoplastic material is increased to a temperature at or above creep relaxation temperature ($T_{cr}$), Vicat softening temperature ($T_{vs}$), heat deflection temperature ($T_{hd}$), and/or melting temperature ($T_m$), and then the optical element is disposed to the thermoplastic material. In an aspect, the optical element can be disposed onto the thermoplastic material while the temperature is maintained at or above the creep relaxation temperature, the heat deflection temperature, the Vicat softening temperature, or the melting temperature, of the thermoplastic material. In another aspect, the optical element can be affixed onto the thermoplastic material after the temperature is allowed to drop below the creep relaxation temperature, the heat deflection temperature, the Vicat softening temperature, or the melting temperature of the thermoplastic material, as long as the thermoplastic material only partially re-solidified and the optical element can be affixed thereto.

In general, the thermoplastic material can have a creep relaxation temperature ($T_{cr}$) of about 80° C. to about 140° C., or from about 90° C. to about 130° C., or about 100° C. to about 120° C. In general, the thermoplastic material can have a Vicat softening temperature ($T_{vs}$) of about 80° C. to about 140° C., or from about 90° C. to about 130° C., or about 100° C. to about 120° C. In general, the thermoplastic material can have a heat deflection temperature ($T_{hd}$) of about 80° C. to about 140° C., or from about 90° C. to about 130° C., or about 100° C. to about 120° C. In general, the thermoplastic material can have a melting temperature ($T_m$) of about 80° C. to about 140° C., or from about 90° C. to about 130° C., or about 100° C. to about 120° C.

In articles that include a textile, the optical element can be disposed onto the textile. The textile or at least an outer layer of the textile can includes a thermoplastic material that the optical element can disposed onto. The textile can be a nonwoven textile, a synthetic leather, a knit textile, or a woven textile. The textile can comprise a first fiber or a first yarn, where the first fiber or the first yarn can include at least an outer layer formed of the first thermoplastic material. A region of the first or second side of the structure onto which the optical element is disposed can include the first fiber or the first yarn in a non-filamentous conformation. The optical element can be disposed onto the textile or the textile can be processed so that the optical element can be disposed onto the textile. The textured surface can be made of or formed from the textile surface. The primer layer can be disposed on the textile surface and then the optical element can be disposed onto the primer layer. The textile surface can be used to form the textured surface, and either before or after this, the primer layer can be optionally applied to the textured surface prior to disposing the optical element to the textile.

A "textile" may be defined as any material manufactured from fibers, filaments, or yarns characterized by flexibility, fineness, and a high ratio of length to thickness. Textiles generally fall into two categories. The first category includes textiles produced directly from webs of filaments or fibers by randomly interlocking to construct non-woven fabrics and felts. The second category includes textiles formed through a mechanical manipulation of yarn, thereby producing a woven fabric, a knitted fabric, a braided fabric, a crocheted fabric, and the like.

The terms "filament," "fiber," or "fibers" as used herein refer to materials that are in the form of discrete elongated pieces that are significantly longer than they are wide. The fiber can include natural, manmade or synthetic fibers. The fibers may be produced by conventional techniques, such as extrusion, electrospinning, interfacial polymerization, pulling, and the like. The fibers can include carbon fibers, boron fibers, silicon carbide fibers, titania fibers, alumina fibers, quartz fibers, glass fibers, such as E, A, C, ECR, R, S, D, and NE glasses and quartz, or the like. The fibers can be fibers formed from synthetic polymers capable of forming fibers such as poly(ether ketone), polyimide, polybenzoxazole, poly(phenylene sulfide), polyesters, polyolefins (e.g., polyethylene, polypropylene), aromatic polyamides (e.g., an aramid polymer such as para-aramid fibers and meta-aramid fibers), aromatic polyimides, polybenzimidazoles, polyetherimides, polytetrafluoroethylene, acrylic, modacrylic, poly(vinyl alcohol), polyamides, polyurethanes, and copolymers such as polyether-polyurea copolymers, polyester-polyurethanes, polyether block amide copolymers, or the like. The fibers can be natural fibers (e.g., silk, wool, cashmere, vicuna, cotton, flax, hemp, jute, sisal). The fibers can be man-made fibers from regenerated natural polymers, such as rayon, lyocell, acetate, triacetate, rubber, and poly (lactic acid).

The fibers can have an indefinite length. For example, man-made and synthetic fibers are generally extruded in substantially continuous strands. Alternatively, the fibers can be staple fibers, such as, for example, cotton fibers or extruded synthetic polymer fibers can be cut to form staple fibers of relatively uniform length. The staple fiber can have a have a length of about 1 millimeter to 100 centimeters or more as well as any increment therein (e.g., 1 millimeter increments).

The fiber can have any of a variety of cross-sectional shapes. Natural fibers can have a natural cross-section, or can have a modified cross-sectional shape (e.g., with processes such as mercerization). Man-made or synthetic fibers can be extruded to provide a strand having a predetermined cross-sectional shape. The cross-sectional shape of a fiber can affect its properties, such as its softness, luster, and wicking ability. The fibers can have round or essentially round cross sections. Alternatively, the fibers can have non-round cross sections, such as flat, oval, octagonal, rectangular, wedge-shaped, triangular, dog-bone, multi-lobal, multi-channel, hollow, core-shell, or other shapes.

The fiber can be processed. For example, the properties of fibers can be affected, at least in part, by processes such as drawing (stretching) the fibers, annealing (hardening) the fibers, and/or crimping or texturizing the fibers.

In some cases a fiber can be a multi-component fiber, such as one comprising two or more co-extruded polymeric materials. The two or more co-extruded polymeric materials can be extruded in a core-sheath, islands-in-the-sea, segmented-pie, striped, or side-by-side configuration. A multi-component fiber can be processed in order to form a plurality of smaller fibers (e.g., microfibers) from a single fiber, for example, by remove a sacrificial material.

The fiber can be a carbon fiber such as TARIFYL produced by Formosa Plastics Corp. of Kaohsiung City, Taiwan, (e.g., 12,000, 24,000, and 48,000 fiber tows, specifically fiber types TC-35 and TC-35R), carbon fiber produced by SGL Group of Wiesbaden, Germany (e.g., 50,000 fiber tow), carbon fiber produced by Hyosung of Seoul, South Korea, carbon fiber produced by Toho Tenax of Tokyo, Japan, fiberglass produced by Jushi Group Co., LTD of Zhejiang, China (e.g., E6, 318, silane-based sizing, filament diameters 14, 15, 17, 21, and 24 micrometers), and polyester fibers produced by Amann Group of Bonningheim, Germany (e.g., SERAFILE 200/2 non-lubricated polyester filament and SERAFILE COMPHIL 200/2 lubricated polyester filament).

A plurality of fibers includes 2 to hundreds or thousands or more fibers. The plurality of fibers can be in the form of bundles of strands of fibers, referred to as tows, or in the form of relatively aligned staple fibers referred to as sliver and roving. A single type fiber can be used either alone or in combination with one or more different types of fibers by co-mingling two or more types of fibers. Examples of co-mingled fibers include polyester fibers with cotton fibers, glass fibers with carbon fibers, carbon fibers with aromatic polyimide (aramid) fibers, and aromatic polyimide fibers with glass fibers.

As used herein, the term "yarn" refers to an assembly formed of one or more fibers, wherein the strand has a substantial length and a relatively small cross-section, and is suitable for use in the production of textiles by hand or by machine, including textiles made using weaving, knitting, crocheting, braiding, sewing, embroidery, or ropemaking techniques. Thread is a type of yarn commonly used for sewing.

Yarns can be made using fibers formed of natural, man-made and synthetic materials. Synthetic fibers are most commonly used to make spun yarns from staple fibers, and filament yarns. Spun yarn is made by arranging and twisting staple fibers together to make a cohesive strand. The process of forming a yarn from staple fibers typically includes carding and drawing the fibers to form sliver, drawing out and twisting the sliver to form roving, and spinning the roving to form a strand. Multiple strands can be plied (twisted together) to make a thicker yarn. The twist direction of the staple fibers and of the plies can affect the final properties of the yarn. A filament yarn can be formed of a single long, substantially continuous filament, which is conventionally referred to as a "monofilament yarn," or a plurality of individual filaments grouped together. A filament yarn can also be formed of two or more long, substantially continuous filaments which are grouped together by grouping the filaments together by twisting them or entangling them or both. As with staple yarns, multiple strands can be plied together to form a thicker yarn.

Once formed, the yarn can undergo further treatment such as texturizing, thermal or mechanical treating, or coating with a material such as a synthetic polymer. The fibers, yarns, or textiles, or any combination thereof, used in the disclosed articles can be sized. Sized fibers, yarns, and/or textiles are coated on at least part of their surface with a sizing composition selected to change the absorption or wear characteristics, or for compatibility with other materials. The sizing composition facilitates wet-out and wet-through of the coating or resin upon the surface and assists in attaining desired physical properties in the final article. An exemplary sizing composition can comprise, for example, epoxy polymers, urethane-modified epoxy polymers, polyester polymers, phenol polymers, polyamide polymers, polyurethane polymers, polycarbonate polymers, polyetherimide polymers, polyamideimide polymers, polystylylpyridine polymers, polyimide polymers bismaleimide polymers, polysulfone polymers, polyethersulfone polymers, epoxy-modified urethane polymers, polyvinyl alcohol polymers, polyvinyl pyrrolidone polymers, and mixtures thereof.

Two or more yarns can be combined, for example, to form composite yarns such as single- or double-covered yarns, and corespun yarns. Accordingly, yarns may have a variety of configurations that generally conform to the descriptions provided herein.

The yarn can comprise at least one thermoplastic material (e.g., one or more of the fibers can be made of thermoplastic material). The yarn can be made of a thermoplastic material. The yarn can be coated with a layer of a material such as a thermoplastic material.

The linear mass density or weight per unit length of a yarn can be expressed using various units, including denier (D) and tex. Denier is the mass in grams of 9000 meters of yarn. The linear mass density of a single filament of a fiber can also be expressed using denier per filament (DPF). Tex is the mass in grams of a 1000 meters of yarn. Decitex is another measure of linear mass, and is the mass in grams for a 10,000 meters of yarn.

As used herein, tenacity is understood to refer to the amount of force (expressed in units of weight, for example: pounds, grams, centinewtons or other units) needed to break a yarn (i.e., the breaking force or breaking point of the yarn), divided by the linear mass density of the yarn expressed, for example, in (unstrained) denier, decitex, or some other measure of weight per unit length. The breaking force of the yarn is determined by subjecting a sample of the yarn to a known amount of force, for example, using a strain gauge load cell such as an INSTRON brand testing system (Norwood, Mass., USA). Yarn tenacity and yarn breaking force are distinct from burst strength or bursting strength of a textile, which is a measure of how much pressure can be applied to the surface of a textile before the surface bursts.

Generally, in order for a yarn to withstand the forces applied in an industrial knitting machine, the minimum tenacity required is approximately 1.5 grams per Denier. Most yarns formed from commodity polymeric materials generally have tenacities in the range of about 1.5 grams per Denier to about 4 grams per Denier. For example, polyester yarns commonly used in the manufacture of knit uppers for footwear have tenacities in the range of about 2.5 to about 4 grams per Denier. Yarns formed from commodity polymeric materials which are considered to have high tenacities generally have tenacities in the range of about 5 grams per Denier to about 10 grams per Denier. For example, commercially available package dyed polyethylene terephthalate yarn from National Spinning (Washington, N.C., USA) has a tenacity of about 6 grams per Denier, and commercially available solution dyed polyethylene terephthalate yarn from Far Eastern New Century (Taipei, Taiwan) has a tenacity of about 7 grams per Denier. Yarns formed from high performance polymeric materials generally have tenacities of about 11 grams per Denier or greater. For example, yarns formed of aramid fiber typically have tenacities of about 20 grams per Denier, and yarns formed of ultra-high molecular weight polyethylene (UHMWPE) having tenacities greater than 30 grams per Denier are available from Dyneema (Stanley, N.C., USA) and Spectra (Honeywell-Spectra, Colonial Heights, Va., USA).

Various techniques exist for mechanically manipulating yarns to form a textile. Such techniques include, for example, interweaving, intertwining and twisting, and interlooping. Interweaving is the intersection of two yarns that cross and interweave at right angles to each other. The yarns utilized in interweaving are conventionally referred to as "warp" and "weft." A woven textile includes include a warp yarn and a weft yarn. The warp yarn extends in a first direction, and the weft strand extends in a second direction that is substantially perpendicular to the first direction. Intertwining and twisting encompasses various procedures, such as braiding and knotting, where yarns intertwine with each other to form a textile. Interlooping involves the formation of a plurality of columns of intermeshed loops, with knitting being the most common method of interlooping. The textile may be primarily formed from one or more yarns that are mechanically-manipulated, for example, through interweaving, intertwining and twisting, and/or interlooping processes, as mentioned above.

The textile can be a nonwoven textile. Generally, a nonwoven textile or fabric is a sheet or web structure made from fibers and/or yarns that are bonded together. The bond can be a chemical and/or mechanical bond, and can be formed using heat, solvent, adhesive or a combination thereof. Exemplary nonwoven fabrics are flat or tufted porous sheets that are made directly from separate fibers, molten plastic and/or plastic film. They are not made by weaving or knitting and do not necessarily require converting the fibers to yarn, although yarns can be used as a source of the fibers. Nonwoven textiles are typically manufactured by putting small fibers together in the form of a sheet or web (similar to paper on a paper machine), and then binding them either mechanically (as in the case of felt, by interlocking them with serrated or barbed needles, or hydro-entanglement such that the inter-fiber friction results in a stronger fabric), with an adhesive, or thermally (by applying binder (in the form of powder, paste, or polymer melt) and melting the binder onto the web by increasing temperature). A nonwoven textile can be made from staple fibers (e.g., from wetlaid, airlaid, carding/crosslapping processes), or extruded fibers (e.g., from meltblown or spunbond processes, or a combination thereof), or a combination thereof. Bonding of the fibers in the nonwoven textile can be achieved with thermal bonding (with or without calendering), hydro-entanglement, ultrasonic bonding, needlepunching (needlefelting), chemical bonding (e.g., using binders such as latex emulsions or solution polymers or binder fibers or powders), meltblown bonding (e.g., fiber is bonded as air attenuated fibers intertangle during simultaneous fiber and web formation).

In accordance with some aspects, the optical element can be disposed on one or more components that form cushioning elements of a sole of an article of footwear. For example, the component can include one or more bladders and the bladder can include the optical element. The bladder can be unfilled, partially inflated, or fully inflated when the structural design (e.g., optical element) is adhered to the bladder. The bladder is a bladder capable of including a volume of a fluid. An unfilled bladder is a fluid-fillable bladder and a filled bladder is one which has been at least partially inflated with a fluid at a pressure equal to or greater than atmospheric pressure. When disposed onto or incorporated into an article, the bladder is generally, at that point, a fluid-filled bladder. The fluid be a gas or a liquid. The gas can include air, nitrogen gas ($N_2$), or other appropriate gas.

The bladder can have a gas transmission rate for nitrogen gas, for example, where a bladder wall of a given thickness has a gas transmission rate for nitrogen that is at least about ten times lower than the gas transmission rate for nitrogen of a butyl rubber layer of substantially the same thickness as the thickness of the bladder described herein. The bladder can have a first bladder wall having a first bladder wall thickness (e.g., about 0.1 to 40 mils). The bladder can have a first bladder wall that can have a gas transmission rate (GTR) for nitrogen gas of less than about 15 $cm^3/m^2 \cdot atm \cdot day$, less than about 10 $m^3/m^2 \cdot atm \cdot day$, less than about 5 $cm^3/m^2 \cdot atm \cdot day$, less than about 1 $cm^3/m^2 \cdot atm \cdot day$ (e.g., from about 0.001 $cm^3/m^2 \cdot atm \cdot day$ to about 1 $cm^3/m^2 \cdot atm \cdot day$, about 0.01 $cm^3/m^2 \cdot atm \cdot day$ to about 1 $cm^3/m^2 \cdot atm \cdot day$ or about 0.1 $cm^3/m^2 \cdot atm \cdot day$ to about 1 $cm^3/m^2 \cdot atm \cdot day$) for an average wall thickness of 20 mils. The bladder can have a first bladder wall having a first bladder wall thickness, where the first bladder wall has a gas transmission rate of 15 $cm^3/m^2 \cdot atm \cdot day$ or less for nitrogen for an average wall thickness of 20 mils.

In an aspect, the bladder has a bladder wall having an interior-facing side (internally-facing side) and an exterior-facing side (externally-facing side), where the interior-facing side defines at least a portion of an interior region of the bladder. The multi-layer optical film (optical element) having a first side and a second opposing side can be disposed on the exterior-facing side of the bladder, the interior-facing side of the bladder, or both. The exterior-facing side of the bladder, the interior-facing side of the bladder, or both can include a plurality of topographical structures extending from the exterior-facing side of the bladder wall, the interior-facing side of the bladder, or both, where the first side or the second side of the multi-layer optical film is disposed on the exterior-facing side of the bladder wall and covering some or all of the plurality of topographical structures, the interior-facing side of the bladder wall and covering some or all of the plurality of topographical structures, or both, and wherein the multi-layer optical film imparts a structural color to the bladder wall. The primer layer can be disposed on the exterior-facing side of the bladder, the interior-facing side of the bladder, or both, between the bladder wall and the multi-layer optical film.

In a particular aspect, the bladder can include a top wall operably secured to the footwear upper, a bottom wall opposite the top wall, and one or more sidewalls extending between the top wall and the bottom wall of the inflated bladder. The top wall, the bottom wall, and the one or more sidewalls collectively define an interior region of the inflated bladder, and wherein the one or more sidewalls each comprise an exterior-facing side. The multi-layer optical film having a first side and a second opposing side can be disposed on the exterior-facing side of the bladder, the interior-facing side of the bladder, or both. The exterior-facing side of the bladder, the interior-facing side of the bladder, or both can include a plurality of topographical structures extending from the exterior-facing side of the bladder wall, the interior-facing side of the bladder, or both, where the first side or the second side of the multi-layer optical film is disposed on the exterior-facing side of the bladder wall and covering some or all of the plurality of topographical structures, the interior-facing side of the bladder wall and covering some or all of the plurality of topographical structures, or both, and wherein the multi-layer optical film imparts a structural color to the bladder wall. The primer layer can be disposed on the exterior-facing side of the bladder, the interior-facing side of the bladder, or both, between the bladder wall and the multi-layer optical film.

An accepted method for measuring the relative permeance, permeability, and diffusion of inflated bladders is ASTM D-1434-82-V. See, e.g., U.S. Pat. No. 6,127,026, which is incorporated by reference as if fully set forth herein. According to ASTM D-1434-82-V, permeance, permeability and diffusion are measured by the following formulae:

Permeance (quantity of gas)/[(area)×(time)×(pressure difference)]=permeance (GTR)/(pressure difference)= $cm^3/m^2 \cdot atm \cdot day$ (i.e., 24 hours)

Permeability

[(quantity of gas)×(film thickness)]/[(area)×(time)× (pressure difference)]=permeability [(GTR)× (film thickness)]/(pressure difference)=[($cm^3$) (mil)]/$m^2 \cdot atm \cdot day$ (i.e., 24 hours)

Diffusion at One Atmosphere (quantity of gas)/[(area)×(time)]=GTR=$cm^3/m^2 \cdot day$ (i.e., 24 hours)

The bladder can include a bladder wall that includes a film including at least one polymeric layer or at least two or more polymeric layers. Each of the polymeric layers can be about 0.1 to 40 mils in thickness.

The polymeric layer can be formed of polymer material such as a thermoplastic material. The thermoplastic material can include an elastomeric material, such as a thermoplastic elastomeric material. The thermoplastic materials can include thermoplastic polyurethane (TPU), such as those described herein. The thermoplastic materials can include polyester-based TPU, polyether-based TPU, polycaprolactone-based TPU, polycarbonate-based TPU, polysiloxane-based TPU, or combinations thereof. Non-limiting examples of thermoplastic material that can be used include: "PELLETHANE" 2355-85ATP and 2355-95AE (Dow Chemical Company of Midland, Mich., USA), "ELASTOLLAN" (BASF Corporation, Wyandotte, Mich., USA) and "ESTANE" (Lubrizol, Brecksville, Ohio, USA), all of which are either ester or ether based. Additional thermoplastic material can include those described in U.S. Pat. Nos. 5,713,141; 5,952,065; 6,082,025; 6,127,026; 6,013,340; 6,203,868; and 6,321,465, which are incorporated herein by reference.

The polymeric layer can be formed of one or more of the following: ethylene-vinyl alcohol copolymers (EVOH), poly(vinyl chloride), polyvinylidene polymers and copolymers (e.g., polyvinylidene chloride), polyamides (e.g., amorphous polyamides), acrylonitrile polymers (e.g., acrylonitrile-methyl acrylate copolymers), polyurethane engineering plastics, polymethylpentene resins, ethylene-carbon monoxide copolymers, liquid crystal polymers, polyethylene terephthalate, polyether imides, polyacrylic imides, and other polymeric materials known to have relatively low gas transmission rates. Blends and alloys of these materials as well as with the TPUs described herein and optionally including combinations of polyimides and crystalline polymers, are also suitable. For instance, blends of polyimides and liquid crystal polymers, blends of polyamides and polyethylene terephthalate, and blends of polyamides with styrenics are suitable.

Specific examples of polymeric materials of the polymeric layer can include acrylonitrile copolymers such as "BAREX" resins, available from Ineos (Rolle, Switzerland); polyurethane engineering plastics such as "ISPLAST" ETPU available from Lubrizol (Brecksville, Ohio, USA); ethylene-vinyl alcohol copolymers marketed under the tradenames "EVAL" by Kuraray (Houston, Tex., USA), "SOARNOL" by Nippon Gohsei (Hull, England), and "SELAR OH" by DuPont (Wilmington, Del., USA); polyvinylidiene chloride available from S.C. Johnson (Racine, Wis., USA) under the tradename "SARAN", and from Solvay (Brussels, Belgium) under the tradename "IXAN"; liquid crystal polymers such as "VECTRA" from Celanese (Irving, Tex., USA) and "XYDAR" from Solvay; "MDX6" nylon, and amorphous nylons such as "NOVAMID" X21 from Koninklijke DSM N.V (Heerlen, Netherlands), "SELAR PA" from DuPont; polyetherimides sold under the tradename "ULTEM" by SABIC (Riyadh, Saudi Arabia); poly(vinyl alcohol)s; and polymethylpentene resins available from Mitsui Chemicals (Tokyo, Japan) under the tradename "TPX".

Each polymeric layer of the film can be formed of a thermoplastic material which can include a combination of thermoplastic polymers. In addition to one or more thermoplastic polymers, the thermoplastic material can optionally include a colorant, a filler, a processing aid, a free radical scavenger, an ultraviolet light absorber, and the like. Each polymeric layer of the film can be made of a different of thermoplastic material including a different type of thermoplastic polymer.

The bladder can be made by applying heat, pressure and/or vacuum to a film. The bladder (e.g., one or more polymeric layers) can be formed using one or more polymeric materials, and forming the bladder using one or more processing techniques including, for example, extrusion, blow molding, injection molding, vacuum molding, rotary molding, transfer molding, pressure forming, heat sealing, casting, low-pressure casting, spin casting, reaction injection molding, radio frequency (RF) welding, and the like. The bladder can be made by co-extrusion followed by heat sealing or welding to give an inflatable bladder, which can optionally include one or more valves (e.g., one way valves) that allows the bladder to be filled with the fluid (e.g., gas).

In examples where the bladder includes the optical element, the optical element can be disposed onto the internally-facing surface (side) of the bladder or the externally-facing surface (side) of the bladder. The textured layer can be the internally-facing surface (side) or the externally-facing surface (side) of the bladder. The optical element can include the optical layer and optionally the primer layer and texture structure. The textured layer can be the internally-facing surface (side) or the externally-facing surface (side) of the bladder (e.g., where the internally-facing or externally-facing side is made of a thermoplastic material) and the primer layer disposed thereon and the optical element disposed on the primer layer.

Now having described embodiments of the disclosure, evaluation of various properties and characteristics described herein are by various testing procedures as described herein below.

Method to Determine the Melting Temperature, and Glass Transition Temperature.

The melting temperature and glass transition temperature are determined using a commercially available Differential Scanning calorimeter ("DSC") in accordance with ASTM D3418-97. Briefly, a 10-15 gram sample is placed into an aluminum DSC pan and then the lead was sealed with the crimper press. The DSC is configured to scan from −100 degrees C. to 225 degrees C. with a 20 degrees C./minute heating rate, hold at 225 degrees C. for 2 minutes, and then cool down to 25 degrees C. at a rate of −10 degrees C./minute. The DSC curve created from this scan is then analyzed using standard techniques to determine the glass transition temperature and the melting temperature.

Method to Determine the Melt Flow Index.

The melt flow index is determined according to the test method detailed in ASTM D1238-13 Standard Test Method for Melt Flow Rates of Thermoplastics by Extrusion Plastometer, using Procedure A described therein. Briefly, the melt flow index measures the rate of extrusion of thermoplastics through an orifice at a prescribed temperature and load. In the test method, approximately 7 grams of the material is loaded into the barrel of the melt flow apparatus, which has been heated to a temperature specified for the material. A weight specified for the material is applied to a plunger and the molten material is forced through the die. A timed extrudate is collected and weighed. Melt flow rate values are calculated in grams/10 min.

Method to Determine the Creep Relation Temperature $T_{cr}$.

The creep relation temperature $T_{cr}$ is determined according to the exemplary techniques described in U.S. Pat. No. 5,866,058. The creep relaxation temperature $T_{cr}$ is calculated to be the temperature at which the stress relaxation modulus of the tested material is 10% relative to the stress relaxation modulus of the tested material at the solidification temperature of the material, where the stress relaxation modulus is measured according to ASTM E328-02. The solidification temperature is defined as the temperature at which there is little to no change in the stress relaxation modulus or little to no creep about 300 seconds after a stress is applied to a test material, which can be observed by plotting the stress relaxation modulus (in Pa) as a function of temperature (in ° C.).

Method to Determine the Vicat Softening Temperature $T_{vs}$.

The Vicat softening temperature $T_{vs}$ is be determined according to the test method detailed in ASTM D1525-09 Standard Test Method for Vicat Softening Temperature of Plastics, preferably using Load A and Rate A. Briefly, the Vicat softening temperature is the temperature at which a flat-ended needle penetrates the specimen to the depth of 1 mm under a specific load. The temperature reflects the point of softening expected when a material is used in an elevated temperature application. It is taken as the temperature at which the specimen is penetrated to a depth of 1 mm by a flat-ended needle with a 1 mm² circular or square cross-section. For the Vicat A test, a load of 10 N is used, whereas for the Vicat B test, the load is 50 N. The test involves placing a test specimen in the testing apparatus so that the penetrating needle rests on its surface at least 1 mm from the edge. A load is applied to the specimen per the requirements of the Vicat A or Vicate B test. The specimen is then lowered into an oil bath at 23° C. The bath is raised at a rate of 50° C. or 120° C. per hour until the needle penetrates 1 mm. The test specimen must be between 3 and 6.5 mm thick and at least 10 mm in width and length. No more than three layers can be stacked to achieve minimum thickness.

Method to Determine the Heat Deflection Temperature $T_{hd}$.

The heat deflection temperature $T_{hd}$ is be determined according to the test method detailed in ASTM D648-16 Standard Test Method for Deflection Temperature of Plastics Under Flexural Load in the Edgewise Position, using a 0.455 MPa applied stress. Briefly, the heat deflection temperature is the temperature at which a polymer or plastic sample deforms under a specified load. This property of a given plastic material is applied in many aspects of product design, engineering, and manufacture of products using thermoplastic components. In the test method, the bars are placed under the deflection measuring device and a load (0.455 MPa) of is placed on each specimen. The specimens are then lowered into a silicone oil bath where the temperature is raised at 2° C. per minute until they deflect 0.25 mm per ASTM D648-16. ASTM uses a standard bar 5"×½"×¼". ISO edgewise testing uses a bar 120 mm×10 mm×4 mm. ISO flatwise testing uses a bar 80 mm×10 mm×4 mm.

EXAMPLES

Example 1: Forming Optical Element Transfer Structure

In this example an optical element was formed on a transfer medium using a vapor deposition device. A release paper (e.g., transfer medium) was used as the carrier for the optical element. The release paper was purchased from Lintec (Tokyo, Japan) and has a model number of EV130TPD. The release paper has a polyolefin coating and the backing is made of cellulose. The optical element was formed on the coating.

The release paper was placed into a deposition device. The deposition device deposited the optical element onto the coating of the release paper.

Example 2: Application of the Optical Element to Textiles Using the Release Paper as a Carrier The optical element coated release paper from Example 1 was used to dispose the optical element onto a variety of textiles. In one example, a woven textile having a first polyester yarn and a second polyester core/sheath yarn with a thermoplastic polyurethane coating (TPU coated yarn) was used.

The woven textile was thermally treated using a heat press including a heated metal plate. The side of the coated release paper with the optical element on it was placed in contact with a side of the woven textile which included the core-sheath yarn, and then the combined textile and release paper were positioned in the heat press, and the heat press was closed so that the heated plate contacted the backing layer of the release paper. The heated plate was heated to a temperature of about 80 degrees C. to about 130 degrees C. The TPU coating of the coated yarn softened or flowed, and took on a non-filamentous conformation during the heat treatment. After heating the textile to a temperature above the softening temperature of the TPU coating material, the combined textile and release paper was removed from contact with the heated plate, and cooled to a temperature below the softening temperature of the TPU coating before the release paper was removed from the textile. The first polyester yarn, as well as the polyester core of the TPU coated yarn, were unaffected by the heat treatment.

As mentioned above, the optical element coated release paper was depressed against the heat treated woven textile during the heat treatment using a pressure of about 40 psi to about 80 psi. A portion (e.g., one or more layers in one or more areas) of the optical element was deposited onto the woven textile. The optical element was deposited on regions of the woven textile where the TPU coating of the TPU coated yarn had softened or melted. The optical element did not deposit onto the polyester yarn. The regions of the woven textile where the optical element was deposited had a blue sheen structural color with some iridescence.

It is worth noting that not all of the optical element was removed from the coated release paper and the optical element coated release paper could be reused.

Example 3: Application of the Optical Element to Textiles Using the Release Paper as a Carrier The optical element coated release paper from Example 1 (another area not used in Example 2) was used to dispose the optical element onto a piece of black synthetic leather. The synthetic leather has a traditional grained leather texture and has a TPU coating on its outer surface.

The synthetic leather was thermally treated was thermally treated using a heat press including a heated metal plate. The side of the coated release paper with the optical element on it was placed in contact with a side of the synthetic leather, and then the combined textile and release paper were positioned in the heat press, and the heat press was closed so that the heated plate contacted the backing layer of the release paper. The heated plate was heated to a temperature of about 80° C. to about 130° C. The TPU coating softened. After heating the textile to a temperature above the softening temperature of the TPU coating material, the combined textile and release paper was removed from contact with the heated plate, and cooled to a temperature below the softening temperature of the TPU coating before the release paper was removed from the textile. A portion of the optical element was deposited onto the synthetic leather. The optical element was deposited on regions of the synthetic leather where TPU layer on the synthetic leather had softened. The regions of the textile where the optical element was deposited had a dark blue structural color, which was darker than what was observed in Example 2. The difference in structural color as well as the appearance of lower levels of iridescence may be due to the darker synthetic leather, the texture of the synthetic leather, or the like.

It is worth noting that not all of the optical element was removed from the coated release paper and the optical element coated release paper could be reused.

It should be emphasized that the above-described aspects of the present disclosure are merely possible examples of implementations, and are set forth only for a clear understanding of the principles of the disclosure. Many variations and modifications may be made to the above-described aspects of the disclosure without departing substantially from the spirit and principles of the disclosure. All such modifications and variations are intended to be included herein within the scope of this disclosure.

The present disclosure can be described in accordance with the following numbered Clauses, which should not be confused with the claims. In each of the clause sets, "disposing" can be replaced with "operably disposing."

Clause 1. A method of making a component comprising:
    providing a transfer medium having a first surface and a second surface; and disposing an optical element onto the first surface of the transfer medium, wherein the optical element has a first side and a second side, wherein the first side of the optical element is disposed on the first surface of the transfer medium.

Clause 2. The method of clause 1, wherein the first surface of the transfer medium includes a release material comprising polyolefins, silicones, polyurethanes, or a combination thereof; wherein disposing the optical element on the first surface of the transfer medium results in the optical element being releasably coupled with the transfer medium.

Clause 3. The method any one of the preceding clauses, wherein disposing the optical element includes forming or depositing the optical element on the first surface of the transfer medium.

Clause 4. The method of any one of the preceding clauses, wherein disposing the optical element onto the first surface of the transfer medium includes depositing the optical element using a technique comprising: physical vapor deposition, electron beam deposition, atomic layer deposition, molecular beam epitaxy, cathodic arc deposition, pulsed laser deposition, sputtering, chemical vapor deposition, plasma-enhanced chemical vapor deposition, low pressure chemical vapor deposition, wet chemistry techniques, or combinations thereof.

Clause 5. The method of any one of the preceding clauses, wherein the first surface of the transfer medium has a substantially flat surface, wherein disposing includes disposing the optical element on the substantially flat surface of the transfer medium.

Clause 6. The method of any one of the preceding clauses, further comprising disposing a textured surface on the transfer medium, or on the optical element, or both.

Clause 7. The method of any one of the preceding clauses, wherein providing a textured surface comprises providing a textured layer within the optical element.

Clause 8. The method of any one of the preceding clauses, further comprising forming a textured surface on the first side or the second side of the optical element.

Clause 9. The method of any one of the preceding clauses, wherein the first surface of the transfer medium has a textured surface, wherein disposing includes disposing the optical element on the textured surface of the transfer medium, resulting in a textured surface on the first side of the optical element.

Clause 10. The method of any one of the preceding clauses, further comprising disposing a primer layer having less than 40% transmittance on the transfer medium or on the optical element.

Clause 11. A method of making an article comprising:
providing an optical element transfer structure having a first side and a second side, wherein the first side of the optical element transfer structure includes a transfer medium, and the second side of the optical element transfer structure includes an optical element;
contacting at least a portion of the second side of the optical element transfer structure with a first surface of a component of an article;
disposing at least a portion of the optical element onto the first surface of the component;
and removing the transfer medium from the optical element so that the portion of the optical element remains disposed on the component;
wherein the optical element, as disposed to the article, imparts a structural color.

Clause 12. The method of clause 11, wherein providing an optical element transfer structure comprises making an optical element transfer structure according the method of any one of the preceding clauses.

Clause 13. The method of any one of the preceding clauses, wherein disposing at least a portion of the optical element to the first surface of the component comprises:
increasing a temperature of the second side of the optical element transfer structure;
applying pressure to the second side of the optical element transfer structure; and
decreasing the temperature of the second side of the optical element transfer structure.

Clause 14. The method of any one of the preceding clauses, wherein, during the disposing, increasing the temperature is conducted prior to or concurrently with the contacting and the applying pressure, and prior to the decreasing the temperature, and the decreasing the temperature is conducted prior to the removing.

Clause 15. The method of any one of the preceding clauses, wherein increasing the temperature includes increasing the temperature of the second side of the optical element transfer structure to a temperature above a softening or melting temperature of a release material of the transfer medium.

Clause 16. The method of any one of the preceding clauses, wherein the first surface of the component comprises a first thermoplastic material, and the disposing at least the portion of the optical element to the first surface of the component comprises disposing at least the portion of the optical element to the thermoplastic material.

Clause 17. The method of any one of the preceding clauses, further providing:
increasing a temperature of the at least a portion of the first surface of the component to a first temperature at or above one of a creep relaxation temperature, a heat deflection temperature, a Vicat softening temperature, or a melting temperature of the first thermoplastic material; and
disposing the optical element to the first thermoplastic material while the temperature of the first surface is at or above the first temperature.

Clause 18. The method of any one of the preceding clauses, further comprising:
lowering the temperature of the first surface of the component to a second temperature that is below one of the creep relaxation temperature, the heat deflection temperature, the Vicat softening temperature, or the melting temperature of the first thermoplastic material to partially re-solidify the first thermoplastic material of the at least a portion of the first surface, and then, while the first surface is at or below the second temperature, disposing the optical element to the at least a portion of the first surface of the component.

Clause 19. The method of any one of the preceding clauses, further comprising:
lowering the temperature of the first surface of the component to a second temperature that is below one of the creep relaxation temperature, the heat deflection temperature, the Vicat softening temperature, or the melting temperature of the first thermoplastic material to partially re-solidify the first thermoplastic material of the at least a portion of the first surface of the component, and then, while the first surface is at or below the second temperature, disposing the optical element to the at least a portion of the first surface.

Clause 20. The method of any one of the preceding clauses, wherein the first thermoplastic material has material has a creep relaxation temperature, a heat deflection temperature, a Vicat softening temperature, or a melting temperature of about 80 degrees C. to about 140 degrees C.

Clause 21. The method of any one of the preceding clauses, wherein the first surface of the component includes a first constituent, wherein the first constituent comprises the first thermoplastic material, wherein the first constituent is selected from a group consisting of a first fiber or filament, a first yarn, a film, a textile, or a combination thereof, and wherein disposing includes disposing the optical element to the first constituent.

Clause 22. The method of any one of the preceding clauses, wherein the first constituent has an externally-facing surface comprising the first thermoplastic material; wherein disposing includes disposing the optical element to the externally-facing surface of the first constituent.

Clause 23. The method of any one of the preceding clauses, wherein the first surface of the component further includes a second constituent, wherein the second constituent is selected from a group consisting of a first fiber or filament, a first yarn, a film, a textile, or a combination thereof, wherein the optical element is not disposed onto the second constituent during the disposing step.

Clause 24. The method of any one of the preceding clauses, wherein the first surface of the component further comprises a second constituent, wherein the second constituent is selected from the group consisting of: a second filament, a second yarn, a second film, a second textile, and a combination thereof, wherein the second constituent comprises a polymeric material having a creep relaxation temperature, a heat deflection temperature, a Vicat softening temperature, or a melting temperature that is at least 20 degrees C. above the creep relaxation temperature, the heat deflection temperature, the Vicat softening temperature, or the melting temperature of the first thermoplastic material; and wherein increasing the temperature of the first surface of the component to a first temperature does not result in softening or melting of the second constituent.

Clause 25. The method of any one of the preceding clauses, wherein the first surface of the component, prior to the increasing its temperature, includes an externally-facing portion which comprises a plurality of fibers in a filamentous conformation that include the first thermoplastic material, and increasing the temperature further comprises:

increasing the temperature of at least a portion of the externally-facing portion of the first surface of the component to a first temperature at or above a creep relaxation temperature, a heat deflection temperature, a Vicat softening temperature, or a melting temperature of the first thermoplastic material to soften or melt the first thermoplastic material and alter the conformation of at least a portion of the fibers present on the externally-facing portion of the first surface to have a non-filamentous conformation, producing a non-filamentous region on the first surface of the component; and wherein disposing the optical element onto the first thermoplastic material comprises disposing the optical element onto the non-filamentous region.

Clause 26. The method of any one of the preceding clauses, further comprising:

lowering the temperature of the first surface of the component to a second temperature that is below the creep relaxation temperature, the heat deflection temperature, the Vicat softening temperature, or the melting temperature of the first thermoplastic material to partially re-solidify the first thermoplastic material of the non-filamentous region, and then disposing the optical element onto the non-filamentous region while the first surface is at or below the second temperature.

Clause 27. The method of any one of the preceding clauses, wherein the portion of the second side of the optical element transfer structure contacting the first surface of the component has a substantially flat surface in the portions that the optical element is disposed onto the component.

Clause 28. The method of any one of the preceding clauses, wherein the portion of the second side of the optical element transfer structure contacting the first surface of the component has a textured surface in portions that the optical element is disposed onto the component.

Clause 29. The method of any one of the preceding clauses, wherein the first surface of the transfer medium has a textured surface, wherein after removing the transfer medium from the optical element, the surface of the optical element has a textured surface that is the inverse or relief of the textured surface of the transfer medium.

Clause 30. The method of any of the preceding clauses, further comprising altering a texture of at least a portion of the first surface of the component.

Clause 31. The method of any one of the preceding clauses, further comprising disposing a textured structure having a textured surface on the first surface of the component.

Clause 32. The method of any one of the preceding clauses, wherein a combination of the textured surface and the optical element impart the structural color to the component.

Clause 33. The method of any one of the preceding clauses, further comprising disposing a primer layer between the optical element and the first surface of the component.

Clause 34. The method of any one of the preceding clauses, wherein the primer layer is disposed between the textured surface and the optical element.

Clause 35. The method of any one of the preceding clauses, wherein the textured surface is disposed between the primer layer and the optical element.

Clause 36. The method of any one of the preceding clauses, wherein the combination of the primer layer, the textured surface, and the optical element impart the structural color.

Clause 37. The method of any one of the preceding clauses, wherein disposing the primer layer includes using a technique including digitally printing, offset printing, pad printing, screen printing, flexographic printing, or heat transfer printing, or a combination thereof.

Clause 38. The method of any one of the method clauses, wherein the article is an article according to any one of the article clauses.

Clause 39. An article comprising a product of the method of any one of the preceding clauses.

Clause 40. An optical element transfer structure comprising:
 a transfer medium having a first surface and a second surface, and
 an optical element disposed on at least a portion of the first surface of the transfer medium, wherein the optical element includes an optical layer.

Clause 41. The article of any one of the preceding clauses, wherein the first surface of the transfer medium includes a release material comprising polyolefins, silicones, polyurethanes, or a combination thereof.

Clause 42. The article of any one of the preceding clauses, wherein the release material has a softening or melting temperature of from about 105 degrees C. to about 140 degrees C.

Clause 43. The article f any one of the preceding clauses, wherein the second surface of the transfer medium comprises cellulose.

Clause 44. The article of any one of the preceding clauses, wherein the transfer medium is release paper.

Clause 45. The article of any one of the preceding clauses, wherein the optical element has a thickness of about 50 nm to about 500 nm.

Clause 46. The article of any one of the preceding clauses, wherein the second side of the optical element further comprises a thermoplastic material.

Clause 47. The article of any one of the preceding clauses, wherein the thermoplastic material has a softening or melting point of from about 80 degrees C. to about 140 degrees C.

Clause 48. The article of any one of the preceding clauses, wherein the thermoplastic material comprises an elastomeric thermoplastic material.

Clause 49. The article of any one of the preceding clauses, wherein the thermoplastic material includes one or more thermoplastic polyurethanes.

Clause 50. An article comprising:
 a component having a first surface;
 an optical element disposed to the first surface of the component; and
 a transfer medium releasably coupled with the optical element.

Clause 51. An article comprising:
 a component having a first surface, the first surface comprising a first thermoplastic material; and
 an optical element disposed to the first thermoplastic material, wherein the optical element imparts a structural color to the component.

Clause 52. The article of any of the preceding clauses, wherein the first thermoplastic material comprises a thermoplastic polymer, optionally wherein the first thermoplastic material includes one or more elastomeric thermoplastic polymers, optionally wherein the first thermoplastic material includes one or more thermoplastic polyurethanes, thermoplastic polyesters, thermoplastic polyamides, thermoplastic polyolefins, thermoplastic co-polymers thereof, or a combination thereof, optionally wherein the first thermoplastic material includes one or more elastomeric thermoplastic polyurethanes, optionally wherein a polymeric component of the first thermoplastic material consists essentially of one or more thermoplastic polyurethanes, optionally wherein a polymeric component of the first thermoplastic material consists essentially of one or more elastomeric thermoplastic polyurethanes.

Clause 53. The article of any of the preceding clauses, wherein the optical element has a thickness of 10 to 500 nm.

Clause 54. The article of any of the preceding clauses, wherein the optical element includes a multilayer reflector or a multilayer filter, optionally wherein the multilayer reflector has at least two layers, including at least two adjacent layers having different refractive indices, optionally wherein at least one of the layers of the multilayer reflector has a thickness that is about one-fourth of the wavelength of visible light to be reflected by the optical element to produce the structural color, optionally wherein at least one of the layers of the multilayer reflector comprises a material selected from the group consisting of: silicon dioxide, titanium dioxide, zinc sulphide, magnesium fluoride, tantalum pentoxide, and a combination thereof.

Clause 55. The article of any of the preceding clauses, wherein the first surface of the component includes a first constituent, wherein the first constituent comprises the first thermoplastic material, wherein the first constituent is selected from a group consisting of a first fiber, a first yarn, a film, a textile, or a combination thereof, optionally wherein the first surface of the component includes a first fiber, wherein the first fiber comprises the first thermoplastic material, optionally wherein the first surface of the component includes a first yarn, wherein the first yarn comprises the first thermoplastic material, optionally wherein the first surface of the component includes a first film, wherein the first film comprises the first thermoplastic material, optionally wherein the first surface of the component includes a first textile, wherein the first textile comprises the first thermoplastic material.

Clause 56. The article of any of the preceding clauses, wherein the optical element is affixed to the first constituent.

Clause 57. The article of any of the preceding clauses, wherein the component further comprises a second constituent, wherein the second constituent is selected from the group consisting of: a second filament, a second yarn, a second film, a second textile, and a combination thereof, wherein the second constituent comprises a polymeric material having a creep relaxation temperature, a heat deflection temperature, a Vicat softening temperature, or a melting temperature that is at least 20° C. above the creep relaxation temperature, the heat deflection temperature, the Vicat softening temperature, or the melting temperature of the first thermoplastic material.

Clause 58. The article of any of the preceding clauses, wherein the second constituent comprises a polymer selected from the group consisting of: polyesters, polyamides, vinyl polymers, polyolefins, polyacrylonitriles, polyphenylene ethers, polycarbonates, polyureas, styrene polymers, co-polymers thereof, and combinations thereof, optionally wherein the second constituent comprises a polymer selected from the group consisting of: polyesters, polyamides, polyolefins, co-polymers thereof, and combinations thereof.

Clause 59. The article of any of the preceding clauses, wherein the first constituent has an externally-facing surface comprising the first thermoplastic material.

Clause 60. The article of any of the preceding clauses, wherein the optical element is affixed to externally-facing surface of the first constituent.

Clause 61. The article of any of the preceding clauses, wherein the first surface of the component has at least one filamentous region at least one non-filamentous region, or a combination thereof.

Clause 62. The article of any of the preceding clauses, wherein the optical element is disposed on at least one of the non-filamentous regions or the filamentous regions.

Clause 63. The article of any of the preceding clauses, further comprising a textured surface having a plurality of profile features and a plurality of flat areas.

Clause 64. The article of any of the preceding clauses, wherein the textured surface is on the first surface of the component.

Clause 65. The article of any of the preceding clauses, wherein the textured surface is on a non-filamentous region of the component, wherein the optical element is disposed on the textured surface on the non-filamentous region.

Clause 66. The article of any of the preceding clauses, wherein the textured surface is on a surface of the optical element.

Clause 67. The article of any of the preceding clauses, further comprising a textured structure having a textured surface, optionally wherein the textured structure comprises a textured layer on a region of the first thermoplastic material, optionally wherein the textured structure comprises a textured layer within the optical element, optionally wherein at least a portion of the plurality of profile features extend above the flat areas of the textured structure, optionally, wherein the dimensions of the profile features, a shape of the profile features, a spacing among the plurality of the profile features, in combination with the optical element create the structural color, optionally wherein the profile features are in random positions relative to one another over an area of the textured surface having a surface area of at least 5 square millimeters, optionally wherein the spacing among the profile features is set to reduce distortion effects of the profile features from interfering with one another in regard to the structural color, optionally wherein the profile features and the flat areas result in at least one layer of the optical element having an undulating topography, wherein there is a planar region between neighboring depressions and/or elevations that is planar with the flat planar areas of the textured surface, wherein the planar region has dimensions relative to the profile features to impart the structural color.

Clause 69. The article of any of the preceding clauses, wherein a primer layer having a percent transmittance of about 40 percent or less is disposed on the textured surface.

Clause 70. The article of any of the preceding clauses, wherein the optical element is disposed on the first thermoplastic material of the side of the article, with the primer layer, the textured surface, or both, positioned between the optical element and the first thermoplastic material.

Clause 71. The article of any of the preceding clauses, wherein the primer layer comprises a textured surface, and the textured surface of the primer layer, the primer layer, and the optical layer imparts the structural color.

Clause 72. The article of any of the preceding clauses, wherein the primer layer is formed from digital printing, offset printing, pad printing, screen printing, flexographic printing, or heat transfer printing.

Clause 73. The article of any of the preceding clauses, wherein the primer layer comprises a paint or ink or a reground, and at least partially degraded polymer.

Clause 74. The article of any of the preceding clauses, wherein the primer layer is an oxide layer, optionally the oxide layer comprises metal oxide or a metal oxynitride, wherein optionally the metal oxide or metal oxynitride is doped.

Clause 75. The article of any of the preceding clauses, wherein the primer layer is a coating, wherein the coating is a crosslinked coating including a matrix of crosslinked polymers, optionally wherein the coating comprises a plurality of solid pigment particles entrapped in the matrix of crosslinked polymers, wherein optionally the matrix of crosslinked polymers includes crosslinked elastomeric polymers, wherein optionally the crosslinked elastomeric polymers include crosslinked polyurethane homopolymers or copolymers or both, and wherein the crosslinked polyurethane copolymers include crosslinked polyester polyurethanes.

Clause 76. The article of any of the preceding clauses, wherein the coating further comprises a dye, optionally the dye is present, the dye is an acid dye, and optionally the coating further comprises a quaternary ammonium compound.

Clause 77. The article of any of the preceding clauses, wherein the matrix of crosslinked polymers of the coating include polyurethane polymers, optionally thermoplastic polyurethane polymers, optionally elastomeric polyurethane polymers, optionally polyester polyurethane copolymers, and optionally the polyurethane polymers consist essentially of polyester polyurethane copolymers.

Clause 78. The article of any preceding clauses, wherein the component comprises a textile, wherein the optical element is affixed to the textile.

Clause 79. The article of any preceding clauses, wherein the textile is a woven, braided, crocheted, knit nonwoven, or synthetic leather.

Clause 80. The article of any preceding clauses, wherein the component is a barrier membrane, wherein the optical element is affixed to the barrier membrane.

Clause 81. The article of any one of the preceding clauses, wherein the first side of the component includes a film, and at least an outer layer of the film includes the first thermoplastic material.

Clause 82. The article of any one of the preceding clauses, wherein the film is a multi-layer film.

Clause 83. The article of any one of the preceding clauses, wherein the first side of the component includes a foam, and at least an outer layer of the foam includes the first thermoplastic material.

Clause 84. The article of any one of the preceding clauses, wherein the first side of the component includes a component formed of solid resin, and at least an outer layer of the component includes the first thermoplastic material.

Clause 85. The article of any one of the preceding clauses, wherein the component formed of solid resin is a molded component.

Clause 86. The article of any one of the preceding clauses, wherein the first side of the component includes an additive manufactured component, and at least an outer layer of the component includes the first thermoplastic material.

Clause 87. The article of any one of the preceding clauses, wherein the first side of the component includes an externally-facing side of a bladder or an internally-facing side of a bladder, and at least an outer layer of the bladder on the externally-facing side or on the internally-facing side includes the first thermoplastic material.

Clause 88. The article of any one of the preceding clauses, wherein the bladder includes the textured surface on the externally-facing side or on the internally-facing side, and a first side of the optical element or a second side of the optical element is disposed on the textured surface.

Clause 89. The article of any one of the preceding clauses, wherein the second side of the optical element is disposed on the internally-facing side of the bladder.

Clause 90. The article of any one of the preceding clauses, wherein the textured surface is disposed on the externally-facing side of the bladder.

Clause 91. The article of any one of the preceding clauses, wherein the first side of the optical element is disposed on the internally-facing side of the bladder, with the primer layer, the textured surface, or both, positioned on the second side of the optical element.

Clause 92. The article of any one of the preceding clauses, wherein the first side of the optical element is disposed on the externally-facing side of the bladder, with the primer layer, the textured surface, or both, positioned between the first side of the optical element and the externally-facing side of the bladder.

Clause 93. The article of any one of the preceding clauses, wherein the article is footwear.

Clause 94. The article of any of the preceding clauses, wherein the component is a component of footwear, and the optical element is affixed to an externally-facing surface of the article of footwear.

Clause 95. The article of any of the preceding clauses, wherein the component is an upper of an article of footwear.

Clause 96. The article of any of the preceding clauses, wherein the component is a sole of an article of footwear.

Clause 97. The article of any of the preceding clauses, wherein the component is a cushioning element of a sole of an article of footwear.

Clause 98. The article of any of the preceding clauses, wherein the component is a bladder of a sole of an article of footwear.

Clause 99. The article of any of the preceding clauses, wherein the article is apparel or a component of apparel, wherein the optical element is affixed to the apparel or a component of apparel.

Clause 100. The article of any of the preceding clauses, wherein the article is sports equipment or a component of sports equipment, wherein the optical element is affixed to the sports equipment or a component of sports equipment.

Clause 101. The article of any of the preceding clauses, wherein the resultant optical element, as affixed to the component, when measured according to the CIE 1976 color space under a given illumination condition at three observation angles between −15 degrees and +60 degrees, has a first color measurement at a first angle of observation having coordinates $L_1^*$ and $a_1^*$ and $b_1^*$, and a second color measurement at a second angle of observation having coordinates $L_2^*$ and $a_2^*$ and $b_2^*$, and a third color measurement at a third angle of observation having coordinates $L_3^*$ and $a_3^*$ and $b_3^*$, wherein the $L_1^*$, $L_2^*$, and $L_3^*$ values may be the same or different, wherein the $a_1^*$, $a_2^*$, and $a_3^*$ coordinate values may be the same or different, wherein the $b_1^*$, $b_2^*$, and $b_3^*$ coordinate values may be the same or different, and wherein the range of the combined $a_1^*$, $a_2^*$ and $a_3^*$ values is less than about 40% of the overall scale of possible a* values, optionally is less than about 30% of the overall scale of possible a* values, optionally is less than about 20% of the overall scale of possible a* values, or optionally is less than about 10% of the overall scale of possible a* values.

Clause 73. The article of any of the preceding clauses, wherein the resultant optical element, as affixed to the component, when measured according to the CIE 1976 color space under a given illumination condition at three observation angles between −15 degrees and +60 degrees, has a first color measurement at a first angle of observation having coordinates $L_1^*$ and $a_1^*$ and $b_1^*$, and a second color measurement at a second angle of observation having coordinates $L_2^*$ and $a_2^*$ and $b_2^*$, and a third color measurement at a third angle of observation having coordinates $L_3^*$ and $a_3^*$ and $b_3^*$, wherein the $L_1^*$, $L_2^*$, and $L_3^*$ values may be the same or different, wherein the $a_1^*$, $a_2^*$, and $a_3^*$ coordinate values may be the same or different, wherein the $b_1^*$, $b_2^*$, and $b_3^*$ coordinate values may be the same or different, and wherein the range of the combined $b_1^*$, $b_2^*$ and $b_3^*$ values is less than about 40% of the overall scale of possible b* values, optionally is less than about 30% of the overall scale of possible b* values, optionally is less than about 20% of the overall scale of possible b* values, or optionally is 10% of the overall scale of possible b* values.

Clause 102. The article of any of the preceding clauses, wherein the resultant optical element, as affixed to the component, when measured according to the CIE 1976 color space under a given illumination condition at two observation angles between −15 degrees and +60 degrees, has a first color measurement at a first angle of observation having coordinates $L_1^*$ and $a_1^*$ and $b_1^*$, and a second color measurement at a second angle of observation having coordinates $L_2^*$ and $a_2^*$ and $b_2^*$, wherein the $L_1^*$ and $L_2^*$ values may be the same or different, wherein the $a_1^*$ and $a_2^*$ coordinate values may be the same or different, wherein the $b_1^*$ and $b_2^*$ coordinate values may be the same or different, and wherein the $\Delta E^*_{ab}$ between the first color measurement and the second color measurement is less than or equal to about 100, where $\Delta E^*_{ab}=[(L_1^*-L_2^*)^2+(a_1^*-a_2^*)^2+(b_1^*-b_2^*)^2]^{1/2}$, optionally is less than or equal to about 80, or optionally is less than or equal to about 60.

Clause 103. The method or article of any of the preceding clauses, wherein the resultant optical element, as affixed to the component, when measured according to the CIELCH color space under a given illumination condition at three observation angles between −15 degrees and +60 degrees, has a first color measurement at a first angle of observation having coordinates $L_1^*$ and $C_1^*$ and $h_1°$, and a second color measurement at a second angle of observation having coordinates $L_2^*$ and $C_2^*$ and $h_2°$, and a third color measurement at a third angle of observation having coordinates $L_3^*$ and $C_3^*$ and $h_3°$, wherein the $L_1^*$, $L_2^*$, and $L_3^*$ values may be the same or different, wherein the $C_{1*}$, $C_2^*$, and $C_3^*$ coordinate values may be the same or different, wherein the $h_1°$, $h_2°$ and $h_3°$ coordinate values may be the same or different, and wherein the range of the combined $h_1°$, $h_2°$ and $h_3°$ values is less than about 60 degrees, optionally is less than about 50 degrees, optionally is less than about 40 degrees, optionally is less than about 30 degrees, or optionally is less than about 20 degrees.

Clause 104. The article of any preceding clause, wherein the structural color is visible to a viewer having 20/20 visual acuity and normal color vision from a distance of about 1 meter from the article.

Clause 105 The article of any preceding clause, wherein the structural color has a single hue.

Clause 106. The article of any preceding clause, wherein the structural color includes two or more hues.

Clause 107. The article of any preceding clause, wherein the structural color is iridescent.

Clause 108. The article of any preceding clause, wherein the structural color has limited iridescence.

Clause 109. The article of the preceding clause, wherein the structural color has limited iridescence such that, when each color visible at each possible angle of observation is assigned to a single hue selected from the group consisting of the primary, secondary and tertiary colors on the red yellow blue (RYB) color wheel, all of the assigned hues fall into a single hue group, wherein the single hue group is one of a) green-yellow, yellow, and yellow-orange; b) yellow, yellow-orange and orange; c) yellow-orange, orange, and orange-red; d) orange-red, and red-purple; e) red, red-purple, and purple; f) red-purple, purple, and purple-blue; g) purple, purple-blue, and blue; h) purple-blue, blue, and blue-green; i) blue, blue-green and green; and j) blue-green, green, and green-yellow.

Clause 110. The article of the preceding clause, wherein the structural color having limited iridescence is limited to two or three of the hues green-yellow, yellow, yellow-orange; or the hues purple-blue, blue, and blue-green; or the hues orange-red, red, and red-purple; or the hues blue-green, green, and green-yellow; or the hues yellow-orange, orange, and orange-red; or the hues red-purple, purple, and purple-blue.

Clause 111. The article of any preceding clause, wherein the primer layer consists essentially of a metal oxide, optionally titanium dioxide or silicon dioxide, and optionally consists essentially of titanium dioxide.

Clause 112. The article of any preceding clause, wherein the primer layer consists essentially of a doped metal oxide or a doped metal oxynitride or both.

Clause 113. The article of any preceding clause, wherein the primer layer has a thickness of about 1 to about 200 micrometers, or optionally of about 10 to about 100 micrometers, or optionally of about 10 to about 80 micrometers.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1 percent to about 5 percent" should be interpreted to include not only the explicitly recited concentration of about 0.1 weight percent to about 5 weight percent but also include individual concentrations (e.g., 1 percent, 2 percent, 3 percent, and 4 percent) and the sub-ranges (e.g., 0.5 percent, 1.1 percent, 2.2 percent, 3.3 percent, and 4.4 percent) within the indicated range. The term "about" can include traditional rounding according to significant figures of the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

What is claimed is:

1. A method of making a component comprising:
providing a transfer medium having a first surface that has a textured surface and a second surface; and
disposing an optical element onto the first surface of the transfer medium, wherein the optical element has a first side and a second side, wherein the first side of the optical element is disposed on the first surface of the transfer medium, resulting in a textured surface on the first side of the optical element.

2. The method of claim 1, wherein the first surface of the transfer medium includes a release material comprising polyolefins, silicones, polyurethanes, or a combination thereof; wherein disposing the optical element on the first surface of the transfer medium results in the optical element being releasably coupled with the transfer medium.

3. The method of claim 1, wherein disposing the optical element includes forming or depositing the optical element on the first surface of the transfer medium.

4. The method of claim 1, wherein disposing the optical element onto the first surface of the transfer medium includes depositing the optical element using a technique comprising: physical vapor deposition, electron beam deposition, atomic layer deposition, molecular beam epitaxy, cathodic arc deposition, pulsed laser deposition, sputtering, chemical vapor deposition, wet chemistry techniques, or combinations thereof.

5. The method of claim 1, further comprising disposing a textured surface on the transfer medium, or on the optical element, or both.

6. The method of claim 1, further comprising forming a textured surface on the first side or the second side of the optical element.

7. The method of claim 1, further comprising disposing a primer layer having less than 40 percent transmittance on the transfer medium or on the optical element.

8. The method of claim 1, further comprising:
providing an optical element transfer structure having a first side and a second side, wherein the first side of the optical element transfer structure includes the transfer medium, and the second side of the optical element transfer structure includes the optical element;
contacting at least a portion of the second side of the optical element transfer structure with a first surface of a component of an article;
disposing at least a portion of the optical element onto the first surface of the component; and
removing the transfer medium from the optical element so that the portion of the optical element remains disposed on the component;
wherein the optical element, as disposed to the component, imparts a structural color.

9. The method of claim 8, wherein disposing at least a portion of the optical element to the first surface of the component comprises:
increasing a temperature of the second side of the optical element transfer structure;
applying pressure to the second side of the optical element transfer structure; and
decreasing the temperature of the second side of the optical element transfer structure.

10. The method of claim 9, wherein, during the disposing, increasing the temperature is conducted prior to or concurrently with the contacting and the applying pressure, and prior to the decreasing the temperature, and the decreasing the temperature is conducted prior to the removing.

11. The method of claim 9, wherein increasing the temperature includes increasing the temperature of the second side of the optical element transfer structure to a temperature above a softening or melting temperature of a release material of the transfer medium.

12. The method of claim 8, wherein the first surface of the component comprises a first thermoplastic material, and the disposing at least the portion of the optical element to the first surface of the component comprises disposing at least the portion of the optical element to the thermoplastic material.

13. The method of claim 12, further comprising:
increasing a temperature of the at least a portion of the first surface of the component to a first temperature at or above one of a creep relaxation temperature, a heat deflection temperature, a Vicat softening temperature, or a melting temperature of the first thermoplastic material; and
disposing the optical element to the first thermoplastic material while the temperature of the first surface is at or above the first temperature.

14. The method of claim 12, further comprising:
increasing a temperature of the at least a portion of the first surface of the component to a first temperature at or above one of a creep relaxation temperature, a heat deflection temperature, a Vicat softening temperature, or a melting temperature of the first thermoplastic material; and
lowering the temperature of the first surface of the component to a second temperature that is below one of the creep relaxation temperature, the heat deflection temperature, the Vicat softening temperature, or the melting temperature of the first thermoplastic material to partially re-solidify the first thermoplastic material of the at least a portion of the first surface, and then, while the first surface is at or below the second temperature, disposing the optical element to the at least a portion of the first surface of the component.

15. The method of claim 8, wherein the first surface of the component has a textured surface, and disposing the at least a portion of the optical element onto the first surface comprises disposing the portion of the optical element onto the textured surface of the component.

16. The method of claim 8, wherein after removing the transfer medium from the optical element, the first side of the optical element retains the textured surface.

17. The method of claim 8, further comprising disposing a primer layer between the optical element and the first surface of the component.

18. The method of claim 12, wherein the first surface of the component includes a first constituent, wherein the first constituent comprises the first thermoplastic material, wherein the first constituent is selected from a group consisting of a first fiber or filament, a first yarn, a film, a textile, or a combination thereof, and wherein disposing includes disposing the optical element onto the first constituent.

19. The method of claim 18, wherein the first surface of the component further includes a second constituent, wherein the second constituent is selected from a group consisting of a second fiber or filament, a second yarn, a film, a textile, or a combination thereof, wherein the optical element is not disposed onto the second constituent during the disposing step.

20. The method of claim 19, further comprising increasing a temperature of the at least a portion of the first surface of the component to a first temperature at or above one of a creep relaxation temperature, a heat deflection temperature, a Vicat softening temperature, or a melting temperature of the first thermoplastic material; and disposing the optical element to the first thermoplastic material while the temperature of the first surface is at or above the first temperature;

wherein the second constituent comprises a polymeric material having a creep relaxation temperature, a heat deflection temperature, a Vicat softening temperature, or a melting temperature that is at least 20 degrees C. above the creep relaxation temperature, the heat deflection temperature, the Vicat softening temperature, or the melting temperature of the first thermoplastic material; and wherein increasing the temperature of the first surface of the component to a first temperature does not result in softening or melting of the second constituent.

* * * * *